(12) United States Patent
Sessler et al.

(10) Patent No.: US 6,207,660 B1
(45) Date of Patent: Mar. 27, 2001

(54) TEXAPHYRIN CONJUGATES AND USES THEREOF

(76) Inventors: Jonathan L. Sessler; Darren Magda; Tarak Mody; Pavel Anzenbacher, Jr.; Joan Carvalho, all of 995 E. Arques Ave., Sunnyvale, CA (US) 94086-4521

( * ) Notice: Subject to any disclaimer, the term of this patent is extended or adjusted under 35 U.S.C. 154(b) by 0 days.

(21) Appl. No.: 09/325,890

(22) Filed: Jun. 4, 1999

Related U.S. Application Data

(60) Provisional application No. 60/088,214, filed on Jun. 5, 1998.

(51) Int. Cl.$^7$ .................. C07D 487/22; A61K 31/335
(52) U.S. Cl. .................. 514/185; 514/2; 514/410; 556/136; 540/145; 540/465; 540/472
(58) Field of Search .................. 514/185; 540/145, 540/472; 556/136

(56) References Cited

U.S. PATENT DOCUMENTS

| | | | |
|---|---|---|---|
| 5,318,962 | * 6/1994 | Khokhar et al. .................. 514/184 |
| 5,322,681 | * 6/1994 | Klaveness .................. 424/9 |
| 5,565,552 | * 10/1996 | Magda et al. .................. 534/11 |
| 5,587,371 | * 12/1996 | Sessler et al. .................. 534/11 |
| 5,595,726 | * 1/1997 | Magda et al. .................. 424/9.61 |
| 5,622,946 | * 4/1997 | Sessler et al. .................. 514/185 |
| 5,888,997 | * 3/1999 | Sessler et al. .................. 514/185 |

FOREIGN PATENT DOCUMENTS

| | | |
|---|---|---|
| 91 18007 | * 11/1991 | (WO). |
| 94 09003 | * 4/1994 | (WO). |
| 97 19938 | * 6/1997 | (WO). |
| 947 44026 | * 11/1997 | (WO). |
| 98 52609 | * 11/1998 | (WO). |
| 99 43317 | * 9/1999 | (WO). |

OTHER PUBLICATIONS

Starling et al., Cancer Chemotherapy, Report, Part 1, vol. 58 No. 5 Sep/Oct. 1974.*

* cited by examiner

*Primary Examiner*—Mukund J. Shah
*Assistant Examiner*—Pavanaram R Sripada
(74) *Attorney, Agent, or Firm*—David A. Lowin; Brian Lewis

(57) ABSTRACT

Texaphyrin/chemotherapeutic drug conjugates, optionally including a platinum(II) or platinum(IV) metal chelating site and/or complex, are useful for treating atheroma, tumors and other neoplastic tissue, neovascular-related diseases, as well as other conditions that are typically responsive to chemotherapy, radiation sensitization and photodynamic therapy.

18 Claims, No Drawings

TEXAPHYRIN CONJUGATES AND USES THEREOF

CROSS-REFERENCE TO RELATED APPLICATIONS

This application is a continuation-in-part of U.S. Provisional application Ser. No. 60/088,214, filed Jun. 5, 1998, incorporated herein by reference.

FIELD OF THE INVENTION

The present invention relates to texaphyrin conjugates, particularly to chemotherapeutic agents, and specifically to a series of texaphyrin-chemotherapeutic agent conjugates. The invention is also directed to formulations and methods for treating atheroma, tumors and other neoplastic tissue, neovascular-related diseases, as well as other conditions that are typically responsive to chemotherapy, radiation sensitization and photodynamic therapy.

BACKGROUND OF THE INVENTION

The texaphyrins are aromatic pentadentate macrocyclic "expanded porphyrins" that have been found to be useful as MRI contrast agents and in photodynamic therapy (PDT). Texaphyrin is considered as being an aromatic oenzannulene containing both $18\pi$- and $22\pi$-electron delocalization pathways. See, e.g., Sessler, J. L. et al., *Accounts of Chemical Research*, 1994, 27:43. It has been determined that the sites of localization of the texaphyrins in vivo include neoplastic tissue and atheromatous plaque. This selective biolocalization underlies many of the pharmaceutical applications of texaphyrins, i.e., in the diagnosis and treatment of cancers and cardiovascular abnormalities. It has also been shown that texaphyrins can act as a radiation sensitizer in the radiation treatment of cancers and as a chemosensitizer to increase the activity of certain chemotherapy drugs.

Conjugates of texaphyrins with "site-directing groups" such as oligonucleotides and estrogen have been prepared. These site-directing groups are chemical entities that can recognize, through non-covalent interactions, a specific receptor molecule. Covalent attachment to such a site-directing group would be expected to direct the texaphyrin complex to the location of the specific receptor molecule recognized.

Texaphyrins, methods of preparation, and uses have been described in, for example, U.S. Pat. Nos. 4,935,498; 5,252,720; 5,457,183; 5,559,207; 5,565,552; 5,567,687; 5,587,371; 5,594,136; and 5,714,328; and International PCT Publication WO 97/26915; all of which are incorporated herein by reference.

Many of the most prevalent forms of human cancer resist effective chemotherapeutic intervention. Some tumor populations, especially adrenal, colon, jejunal, kidney and liver carcinomas, appear to have drug-resistant cells at the outset of treatment (Barrows, L. R., in *Remington: The Science and Practice of Pharmacy*, Mack Pub. Co., Easton, Pa., 1995, p. 1249). In other cases, resistance appears to be acquired in much the same way as microbial resistance: a resistance-conferring genetic change occurs during treatment; the resistant daughter cells then proliferate in the environment of the drug. Whatever the cause, resistance often terminates the usefulness of an antineoplastic drug.

Cisplatin ("cis-Pt"; diammine(dichloro)platinum(II)) was first synthesized by Peyrone in 1844; however, the tumor-inhibiting properties of the compound were not recognized until 1969 by Rosenberg (Rosenberg, B., et al., *Nature*, 1969, 222:385–386). Today, cisplatin has become one of the most frequently used anticancer drugs. It is prescribed for the treatment of testicular and ovarian cancer and has recently been shown to be effective against cervical, bladder, and head/neck tumors. The generally accepted mechanism for its antitumor activity involves intrastrand coordination of $[Pt(NH_3)_2(H_2O)_nCl_{2-n}]$ (formed after intracellular hydrolysis of cis-Pt) to cellular DNA, preferentially at the $N^7$ atoms of two adjacent guanine bases, thus blocking DNA replication.

Although cisplatin is a widely used drug, there are several drawbacks associated with its treatment regime and activity. Primarily, the platinum complex is poorly soluble in saline, and patients can experience severe toxic side effects to treatment, including nausea, hearing loss, vomiting, loss of sensation in hands, and renal toxicity. Cisplatin acts unspecifically and damages all rapidly growing body tissues as well as the tumor. Additionally, cisplatin can be used for only a narrow range of tumors and some tumor cell lines may develop resistance to the platinum drug.

Efforts to find better cytotoxic agents have involved chemically linking a cis-Pt center, or an analogous platinum coordination complex, to a biocompatible carrier that will improve its ability to target certain organs, tissues, or tumor cells. Specifically, coordination inter alia to amino phosphonic acids (Bloemink, M. J. et al. *Inorg. Chem.*, 1994, 33:1127–1132), ferrocene (Rosenfeld, A. et al. *Inorg. Chim. Acta*, 1992, 201:219–221), and porphyrins (Brunner, H. et al. *Chem. Ber.*, 1995, 128:173–181; *Chem. Ber.*, 1994, 127:2141–2149) has been tried, but with limited success. Cis-Pt has also been linked to agents that target cellular DNA, namely intercalating acridine chromophores (Lee, H. H. et al. *J. Med. Chem.*, 1992, 35:2983–2987; Wickham, G. et al. *In Platinum and Other Metal Coordination Complexes in Cancer Chemotherapy*, S. B. Howell, Ed., Plenum Press, N.Y., 1991, pp. 51–60; Mikata, Y. et al. *Bioorg. Med. Chem. Lett.*, 1997, 7:1083–1086; Bowler, B. E. et al. *J. Am. Chem. Soc.*, 1989, 111:1299–1306). Alternatively, cisplatin complexes (containing co-ligands that may offer an additive or synergistic effect to disease treatment have also been synthesized. These systems may offer additional chemotherapeutic capabilities (Hollis, L. S. et al. *J. Med. Chem.*, 1990, 33:105–111) or may enhance other types of treatment. Nitroimidazoles, which are radiosensitizers, have been complexed with cis-Pt-type complexes in order to enable radiation therapy to be pursued in conjunction with chemotherapy (Farrell, N., and Skov, K. A. *J. Chem. Soc. Chem. Commun.*, 1987, 1043–1044). Complexation with porphyrins has also been considered in this context (Brunner, H. et al., supra).

Doxorubicin (adriamycin) is another widely used drug in the battle against cancer. It is an anthracycline antibiotic that binds to DNA and inhibits nucleic acid synthesis, inhibits topoisomerase II and produces oxygen radicals. Doxorubicin has the widest antineoplastic spectrum and usefulness of the antineoplastic drugs (Barrows, L. R., in *Remington: The Science and Practice of Pharmacy*, Mack Publ. Co., Easton, Pa., 1995, p. 1249). As with other chemotherapeutic drugs, the anthracyclines cause serious, including toxic, side effects in patients, including bone marrow suppression and mucositis, which are dose limiting; hair loss; extravasation, which leads to severe local reaction; cumulative cardiomyopathy that can lead to congestive heart failure; and cardiac toxicity.

Taxol (Paclitaxel), a complex diterpenoid isolated in small yields from the bark of the western yew *Taxus brevifolia*, and its semisynthetic derivative docetaxel (Taxotere, Rhone-Poulenc) constitute one of the most potent drugs in cancer chemotherapy. Paclitaxel has been approved by FDA for treatment of ovarian and breast cancer and is also showing promise in the treatment of lung, skin, and head/neck cancers.

Unfortunately, the clinical utility of taxoid drugs (i.e., Paclitaxel, Docetaxel) is severely constrained by their cost, limited bioavailability (a direct reflection of low iaqueous solubility), and the development of multiresistant cells. To date, considerable effort has indeed been devoted to the problem of improving the water solubility of taxol using such classic strategies as prodrug masking and conjugate construction. However, it is fair to say that the problem is far from solved. Indeed, there are several significant challenges related to the design of successful taxol prodrugs and conjugates. First, the product produced, whether a prodrug or a conjugate, should be at least partially water soluble (to facilitate administration). However, it needs to retain sufficient lipophilicity such that is not cleared through the kidneys too quickly. Second, and perhaps more seriously, it must retain the basic biological character of taxol, notably the ability to bind to the surprisingly selective receptor on microtubules.

SUMMARY OF THE INVENTION

One aspect of the present invention concerns texaphyrin-chemotherapeutic agent conjugates and derivatives thereof (including pharmaceutically acceptable salts, esters and apical ligands thereof) represented by Formulae (A) and (B):

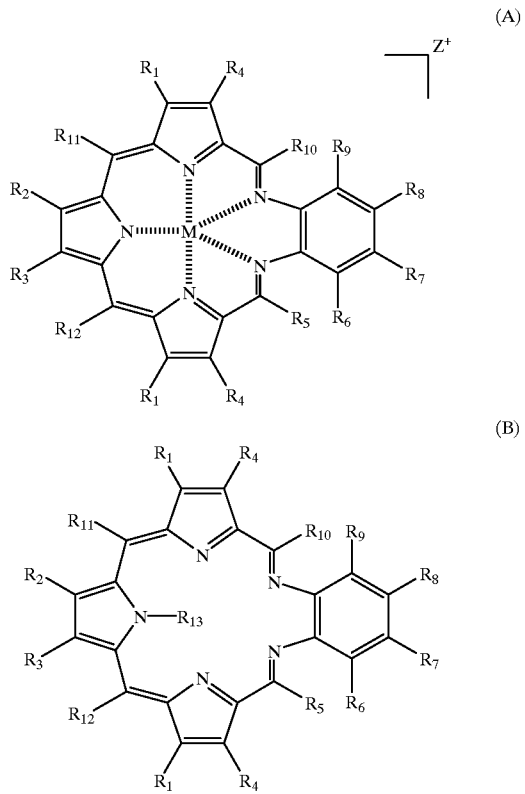

wherein,

Z is zero or an integer less than or equal to 5;

M is hydrogen, a divalent metal cation or a trivalent metal cation;

$R_1$–$R_4$ and $R_6$–$R_9$ are independently hydrogen, halide other than iodide, hydroxyl, alkyl, alkenyl, aryl, haloalkyl other than iodoalkyl, nitro, formyl, acyl, hydroxyalkyl, alkoxy, hydroxyalkoxy, saccharide, aminoalkyl, aminoalkoxy, carboxy, carboxyalkyl, carboxyamide, carboxyamidealkyl, a catalytic group, a couple to a catalytic group, a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV);

$R_5$ and $R_{10}$–$R_{12}$ are independently hydrogen, alkyl, alkenyl, aryl, halide other than iodide, hydroxyalkyl, alkoxy, hydroxyalkoxy, aminoalkyl, aminoalkoxy, carboxyalkyl or carboxyamidealkyl, with the proviso that:

where $R_5$ is sterically larger than hydrogen or methyl, $R_6$ is hydrogen, methyl, methoxy or halide other than iodide, where $R_6$ is sterically larger than hydrogen or methyl, $R_5$ is hydrogen, methyl, methoxy or halide other than iodide, where $R_9$ is sterically larger than hydrogen or methyl, $R_{10}$ is hydrogen, methyl, methoxy or halide other than iodide, and where $R_{10}$ is sterically larger than hydrogen or methyl, $R_9$ is hydrogen, methyl, methoxy or halide other than iodide;

$R_{13}$ (i.e., in the compounds of Formula B) is selected from alkyl, alkenyl, alkoxy or hydroxyalkyl having up to about three carbon atoms and having rotational flexibility around a first-bound carbon atom, with the proviso that at least one of $R_1$–$R_4$ or $R_6$–$R_9$ is a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum (IV).

Another embodiment of the invention entails texaphyrin-chemotherapeutic agent conjugates where the platinum(II) or platinum(IV) metal chelating site is selected from the group consisting of amines, diamines, carboxylates, dicarboxylates, and amino acids., including Formulae (I) through (IV):

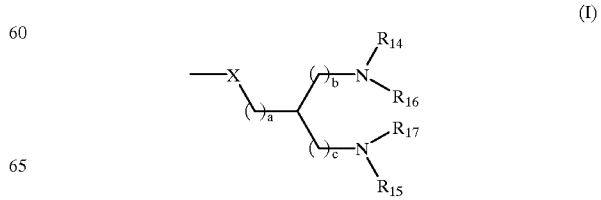

-continued

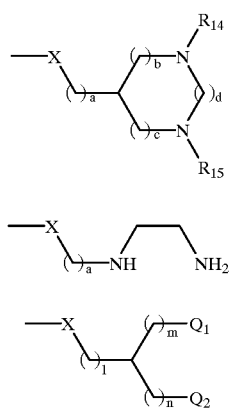

where:
- X is a covalent bond or is a couple selected from —$(CH_2)_{nn}$— (where nn=1–15), —O—, —NH—, —N($R_{18}$)—, —C(O)—N($R_{18}$)—, —N($R_{18}$)—C(O)—, —O—C(O)—, —C(O)—O—, —O—C(O)—O—, —O—P(O)(OH)—O—, —O—C(O)—N($R_{18}$)—, —N($R_{18}$)—O—C(O)—, —N($R_{18}$)—C(O)—N($R_{19}$)—, —S—, —S(O)—, and —O—S(O)—O—;
- $Q_1$ and $Q_2$ are independently selected from —H, —C(O)—O$^-$, —O—C(O)—O$^-$, —N($R_{20}$)—C(O)—O$^-$, —C(O)—N($R_{21}$)$_2$—, —N($R_{22}$)$_2$—, —P(O)(OH)—O$^-$, —C(S)—S—, and —N—C(S)—N($R_{23}$)$_2$—;
- $R_{14}$–$R_{17}$ are independently hydrogen, alkyl, aryl, alkylaryl, alkoxyalkyl, substituted or unsubstituted residues, or are a protective masking group;
- $R_{18}$–$R_{23}$ are independently hydrogen, alkyl, aryl, alkylaryl, alkoxyalkyl, substituted or unsubstituted residues;
- a, b, and c are independently zero or an integer from 1 to 8;
- d is an integer from 1 to 8; and
- l, m, and n are independently zero or an integer from 1 to 8.

In another aspect, the invention relates to a pharmaceutical composition containing a therpeutically effective amount of a compound of Formula A or B admixed with at least one pharmaceutically acceptable excipient.

The chemotherapeutic agent employed in the conjugates of the invention are selected from a taxoid, a nucleotide, an antibiotic, or a platinum coordination complex, preferably from bleomycin, doxorubicin, taxol, taxotere, etoposide, 4-OH cyclophosphamide, 5-fluorouracil, cisplatin, or platinum coordination complexes analogous to cisplatin.

In still another aspect, the invention relates to a method of treating atheroma, tumors and other neoplastic tissue, neovascular-related diseases, as well as other conditions that are typically responsive to chemotherapy, radiation sensitization and photodynamic therapy in a mammal by administering to a mammal in need of such treatment a therapeutically effective amount of a compound of Formula A or B. The neoplasm can be leukemia, lymphoma, carcinoma, or sarcoma, for example. In addition to the advantages provided by selective biolocalization of the texaphyrin, since certain texaphyrins act themselves as chemosensitizers the close proximity of the texaphyrin conjugate to the chemotherapeutic drug via conjugation should greatly increase the anticancer activity of the drug.

The present invention is directed to the use of texaphyrins as carrier molecules to direct other agents, such as chemotherapeutic drugs, to sites of selective texaphyrin accumulation. More specifically, the texaphyrin will selectively deliver an agent, such as an anticancer drug, to which the texaphyrin is conjugated to tumors and other neoplastic tissue, providing enhanced activity and/or decreased side effects of the drug.

In another embodiment of the invention, the host is administered ionizing radiation in proximity to the tumor or neoplastic tissue after a texaphyrin-chemotherapeutic agent conjugate has been given. In this method of the invention, the texaphyrin is chosen from those exhibiting radiation-sensitizing characteristics. Texaphyrins have been demonstrated to have radiation sensitization properties; they enhance cytotoxicity from ionizing radiation in the vicinity of the texaphyrin as compared to control experiments. Ionizing radiation includes, but is not limited to, x-rays, internal and external gamma-emitting radioisotopes, and ionizing particles.

Treatment with a chemotherapeutic agent may be combined with photodynamic therapy applications, since certain texaphyrins are photosensitive molecules and have absorption in the physiologically important range of 700–900 nm. The method is that of treating a tumor or other neoplastic tissue by administering a photosensitive texaphyrin-chemotherapeutic agent conjugate to a patient, and photoirradiating the patient in the vicinity of the tumor or neoplastic tissue. In this combined treatment, the texaphyrin may be metal-free or in a complex with a metal. If metallated, the metal is a diamagnetic metal cation, and preferably the diamagnetic metal cation may be selected from Lu(III), La(III), In(III), Y(III), Zn(II) and Cd(II). More preferably, the metal cation is Lu(III).

The present invention further includes conjugates of texaphyrins and chemotherapeutic drugs. The texaphyrin acts as a drug delivery agent and a carrier molecule that helps target the chemotherapeutic agents to sites of selective texaphyrin accumulation; that is, to tumors and other neoplastic tissue. This provides for increased accumulation of the anticancer drug in the areas of the body where its activity is the most beneficial, while providing decreased accumulation in, and thus decreased damage to healthy cells.

The invention is further directed to texaphyrin compounds having a metal chelating site capable, in its "free" or active form, of coordinating platinum(II) or platinum(IV), including Pt-containing chemotherapeutic agents. The chelating site may be an amine, a diamine, a carboxylate, a dicarboxylate, or an amino acid, for example, in free or masked form.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

"Alkyl" means alkyl groups, straight, branched or as cyclic isomers, with generally one to fifty, preferably one to thirty, more preferably one to ten, carbon atoms. Presently preferred are methyl, ethyl, and propyl.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds. Ethenyl and propenyl are presently preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Alkoxy" means alkyl groups as herein described with oxygen atoms, including ether or ester linkages. The number of repeating alkoxys within a substituent may be up to 200, preferably from 1 to 20, more preferably from 1 to 7, and most preferably is 2–5. A presently preferred alkoxy is $O(CH_2CH_2O)_xCH_3$, where x=1–100, preferably 1–10, and more preferably, 2–5.

"Hydroxyalkoxy" means alkyl groups as described herein having ether or ester linkages, as well as hydroxyl groups, carbonyl groups, substituted hydroxyl groups, substituted carboxyl groups or the like, such as polyethers including polyethylene glycols such as $O(CH_2CH_2O)_xH$, where x=1–100, preferably 1–10, and more preferably, 2–5.

"Substituted hydroxyl", "carbonyl" and "substituted carboxyl" groups, mean groups respectively of the formulae —O—$R^a$, —C(O)—$R^a$ and —C(O)—O—$R^a$, where $R^a$ is selected from protecting groups such as tosylate, mesylate, MOM and MEM, alkyl, alkoxy, hydroxyalkyl, hydroxyalkoxy, carboxy, carbonyl, saccharide, —NR'R" where R' and R" can be hydrogen, alkyl, saccharide or like functional groups as described herein.

"Carboxyl" groups include carboxylic acids of the alkyl groups described herein as well as aryl carboxylic acids such as benzoic acid.

"Carboxyalkyl" means alkylene groups having hydroxyl groups, carboxyl or amide-substituted ethers, ester linkages, tertiary amide linkages, or the like.

"Carboxyamides" include primary carboxyamides ($CONH_2$), and secondary (CONHR') and tertiary (CONR'R") carboxyamides where each of R' and R" is a functional group as described herein.

"Carboxyamidealkyl" means a carboxyamide attached to an alkylene group.

Representatives of useful amines include a primary, secondary or tertiary amine of an alkyl as described hereinabove.

"Aryl" may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, unsubstituted or substituted with one or more nitro, carboxy, sulfonic acid, hydroxy, alkoxy, or halide substituents.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and metallotexaphyrin complexes.

A "conjugate" group having chemotherapeutic activity or catalytic activity may be covalently coupled to a texaphyrin directly on the macrocycle ring or through various couples. A "couple" may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds. The catalytic groups, chemotherapeutic agents, and platinum(II) or platinum(IV) metal chelating sites are attached either directly to the texaphyrin complex or to the texaphyrin complex via a linker or couple of variable length, or are attached to the chemotherapeutic agent molecule portion of a texaphyrin complex-conjugate either with or without a linker or couple of variable length. In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond. The couple may be either a permanent or a semipermanent linkage. A semipermanent couple allows separation of the texaphyrin and the chemotherapeutic agent once the conjugate has reached the treatment site. For example, the couple may be a labile linkage, such as a disulfide or an ester, (e.g., a nucleotide) which provides a stable texaphyrin-agent conjugate in the bloodstream but allows separation of the texaphyrin and the agent upon the conjugate's entering the more reducing environment of the cell (e.g., via phosphodiesterase activity).

The term "sterically larger" means, to the extent that a selected substituent would sterically hinder an adjacent substituent, the adjacent substituent must be of a compatible size and nature.

The term "treatment" or "treating" means any treatment of a disease in a mammal, which will depend on the particular texaphyrin-chemotherapeutic agent conjugate, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

"Optional" or "optionally" means that the subsequently described event or circumstance may or may not occur, and that the description includes instances where said event or circumstance occurs and instances in which it does not.

Compositions of the Present Invention

The present invention is directed to texaphyrin-chemotherapeutic agent conjugates useful in the treatment of atheroma, tumors and other neoplastic tissue, neovascular-related diseases, as well as other conditions that are typically responsive to chemotherapy, radiation sensitization and photodynamic therapy. The texaphyrins preferentially accumulate in atheroma, macrophages, tumors, other neoplasms and neovasculature; they exhibit little or no accumulation in healthy tissues. Thus, in the conjugates of this invention, the texaphyrin can act as a drug delivery agent or carrier molecule, transporting a conjugated chemotherapeutic agent to sites where the agent is most useful while reducing the extent to which the agent accumulates in healthy cells, with a consequent enhancement of the activity of the agents while decreasing their adverse side effects. For example, it is contemplated that, due to the preferential accumulation in neoplastic tissue, lower doses of an anticancer agent would be necessary to effect good anticancer activity. The chemotherapeutic agent cisplatin has a very serious side effect, renal toxicity. Because texaphyrins clear the body primarily through the hepatic route; a texaphyrin-cisplatin conjugate would be expected to clear primarily through the liver, thereby diminishing complexed cisplatin's potential for renal toxicity. With respect to doxorubicin, texaphyrin-doxorubicin conjugates would be expected to eliminate or greatly decrease the current cardiomyopathy and cardiotoxicity associated with doxorubicin. While texaphyrins do accumulate in atheromatous plaque, they do not accumulate to any significant extent in the normal heart tissue and would be expected to diminish the complexed doxorubicin's potential for cardiomyopathy and cardiotoxicity.

Generally, water-soluble texaphyrins retaining lipophilicity are preferred for the applications described herein. "Water-soluble" means soluble in aqueous fluids to about 1 mM or better. "Retaining lipophilicity" means having greater affinity for lipid-rich tissues or materials than surrounding nonlipid-rich tissues. "Lipid-rich" means having a greater amount of triglyceride, cholesterol, fatty acids or the like.

The texaphyrins offer a significant advance over porphyrin-based systems because (i) they form stable 1:1 complexes with trivalent lanthanide ions, particularly Gd(III) and Lu(III), and can thus be used for delivery of a chemotherapeutic agent in conjunction with radiation sensitization (in the case of paramagnetic metal ions) or photodynamic therapy (with diamagnetic metal ions); (ii) they possess a lower inherent toxicity; and (iii) they are readily derivatized on the tripyrrolic (T) and/or benzene (B) portions of the macrocycle, with, for example, water-solubilizing groups such as hydroxypropyl, poly(ethylene glycol), saccharides, oligopeptides and oligonucleotides, etc.

The texaphyrin-chemotherapeutic agent conjugates and derivatives of the present invention are the compounds (including pharmaceutically acceptable salts, esters and apical ligands thereof) represented by Formulae A and C:

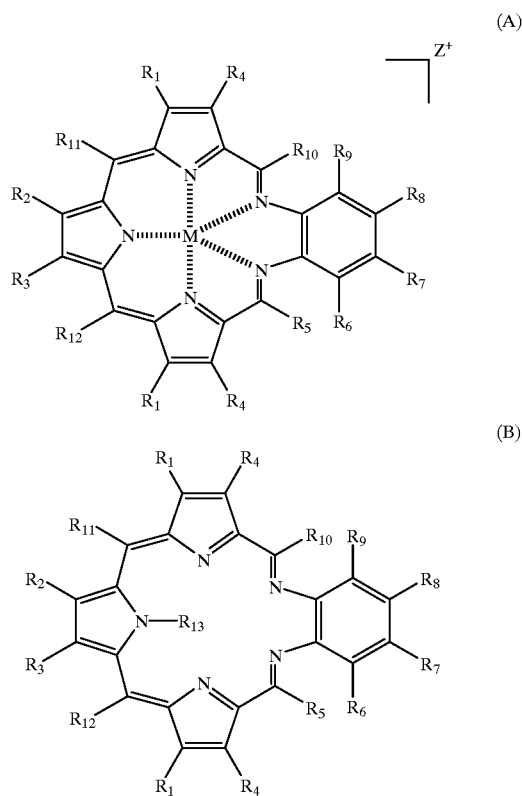

wherein,

Z is zero or an integer less than or equal to 5;

M is hydrogen, a divalent metal cation or a trivalent metal cation;

$R_1$–$R_4$ and $R_6$–$R_9$ are independently hydrogen, halide other than iodide, hydroxyl, alkyl, alkenyl, aryl, haloalkyl other than iodoalkyl, nitro, formyl, acyl, hydroxyalkyl, alkoxy, hydroxyalkoxy, saccharide, aminoalkyl, aminoalkoxy, carboxy, carboxyalkyl, carboxyamide, carboxyamidealkyl, a catalytic group, a couple to a catalytic group, a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV);

$R_5$ and $R_{10}$–$R_{12}$ are independently hydrogen, alkyl, alkenyl, aryl, halide other than iodide, hydroxyalkyl, alkoxy, hydroxyalkoxy, aminoalkyl, aminoalkoxy, carboxyalkyl or carboxyamidealkyl, with the proviso that:

where $R_5$ is sterically larger than hydrogen or methyl, $R_6$ is hydrogen, methyl, methoxy or halide other than iodide, where R$_6$ is sterically larger than hydrogen or methyl, R$_5$ is hydrogen, methyl, methoxy or halide other than iodide, where R$_9$ is sterically larger than hydrogen or methyl, R$_{10}$ is hydrogen, methyl, methoxy or halide other than iodide, and where R$_{10}$ is sterically larger than hydrogen or methyl, R$_9$ is hydrogen, methyl, methoxy or halide other than iodide;

R$_{13}$ (i.e., in the compounds of Formula B) is selected from alkyl, alkenyl, alkoxy or hydroxyalkyl having up to about three carbon atoms and having rotational flexibility around a first-bound carbon atom, with the proviso that at least one of R$_1$–R$_4$ or R$_6$–R$_9$ is a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum (IV).

In the compounds of the present invention, Z will typically be zero or an integer less than or equal to 5. In the context of the basic texaphyrin macrocycle with a divalent or trivalent metal cation, Z is 1 or 2; however, one skilled in the art in light of the present disclosure would realize that the value of Z would also be altered clue to charges present on substituents R$_1$–R$_{12}$. The complexes described in the present invention may have one or more additional ligands providing charge neutralization and/or coordinative saturation to the metal ion. Such ligands include, but are not limited to, chloride, nitrate, acetate, phosphate, gluconate, glucose-6-phosphate, and hydroxide.

M is preferably a divalent or a trivalent metal cation. The divalent metal cation may be selected from, but is not limited to, the group consisting of Ca(II), Eu(II), Mn(II), Co(II), Ni(II), Zn(II), Cd(II), Hg(II), Fe(II), Sm(II) and UO$_2$(II). The trivalent metal cation may be selected from, but is not limited to, the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

The pyrrole nitrogen substituent (R$_{13}$) of the texaphyrins of Formula B may be an alkyl, alkenyl, hydroxyalkyl, or alkoxy group having up to about 3 carbon atoms; with the provision that the substituent has rotational flexibility after the first-bound carbon to allow the rest of the group to be positioned outside the plane of the texaphyrin. Thus, a preferred alkenyl is —CH$_2$—CH=CH$_2$. The pyrrole nitrogen substituent is most preferably a methyl group.

The platinum(II) or platinum(IV) metal chelating site can be an amine, a diamine, a carboxylate, a dicarboxylate, or an amino acid, for example. The chelating site can be in free (active) or masked form. By "masked" is meant that the functional portion of the chelating site is protected, oxidized, reduced, or derivatized prior to reaction with platinum; it is de-protected (converted to active form) for reaction to form the platinum chelate. Where a chemotherapeutic agent contains platinum(II) or platinum(IV), the metal chelating (or coordinating) site of the texaphyrin acts as the couple for linking the texaphyrin and the chemotherapeutic agent to give the texaphyrin-chemotherapeutic agent conjugate. Agents containing platinum(II) or platinum(IV) include cis-platin and analogous platinum amine complexes. Examples of such platinum metal chelating sites are represented by Formulae I–IV:

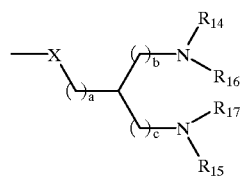
(I)

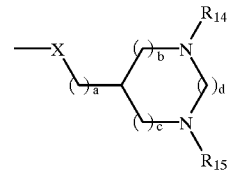
(II)

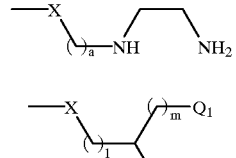
(III)

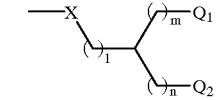
(IV)

where:

X is a covalent bond or is a couple selected from an amide, amine, thiol, thioether, ether, or phosphate, including but not limited to —(CH$_2$)$_n$— (where n=1–15), —O—, —NH—, —N(R$_{18}$)—, —C(O)—N(R$_{18}$)—, —N(R$_{18}$)—C(O)—, —O—C(O)—, —C(O)—O—, —O—C(O)—O—, —O—P(O)(OH)—O—, —O—C(O)—N(R$_{18}$)—, —N(R$_{18}$)—O—C(O)—, —N(R$_{18}$)—C(O)—N(R$_{19}$)—, —S—, —S(O)—, —O—S(O)—O—, and the like;

Q$_1$ and Q$_2$ are independently selected from groups that can be used to coordinate the metal center, either in a covalent or coordinate fashion, and which include but are not limited to —H, —C(O)—O$^-$, —O—C(O)—O$^-$, —N(R$_{20}$)—C(O)—O$^-$, —C(O)—N(R$_{21}$)$_2$—, —N(R$_{22}$)$_2$—, —P(O)(OH)—O$^-$, —C(S)—S—, —N—C(S)—N(R$_{23}$)$_2$—, or any combination of these groups. In a preferred embodiment Q$_1$ and Q$_2$ are carboxylic acid anions;

R$_{14}$–R$_{17}$ are independently hydrogen, alkyl, aryl, alkylaryl, alkoxyalkyl, substituted or unsubstituted residues, or are a protective masking group that protects the functional portion of the chelating site (e.g., by oxidation, reduction or derivatization) and may be an amine, a diamine, a carboxylate, a dicarboxylate, or an amino acid, such as BOC, F-moc, trifluoroamide, esters and benzyl derivatives, and diols such as either, a diamine or a diacid precursor (via oxidation);

R$_{18}$–R$_{23}$ are independently hydrogen, alkyl, aryl, alkylaryl, alkoxyalkyl, substituted or unsubstituted residues;

a, b, and c are independently zero or an integer from 1 to 8, preferably 0 to 5, more preferably 1 to 3;

d is an integer from 1 to 8, preferably 1 to 5, more preferably 1 to 3; and l, m, and n are independently zero or an integer from 1 to 8, preferably 0 to 5, more preferably from 0 to 2.

The Pt metal chelating site is preferably at any of R$_1$–R$_4$, R$_7$ and/or R$_8$ of the texaphyrin macrocycle, more preferably at R$_1$, R$_7$ or R$_8$, most preferably at R$_7$ or R$_8$. Presently preferred embodiments of this aspect of the invention are represented by Formulae (V) to (VIII):

(V)
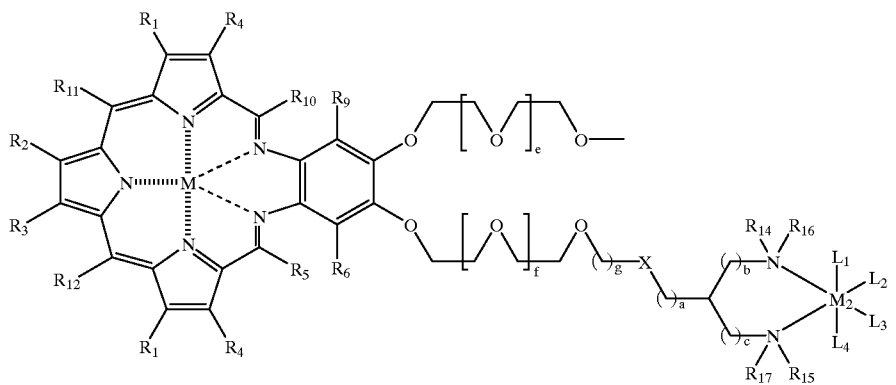
(VI)
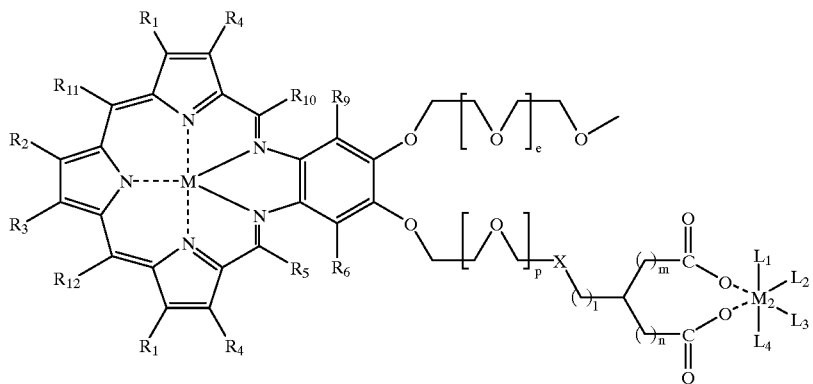
(VII)
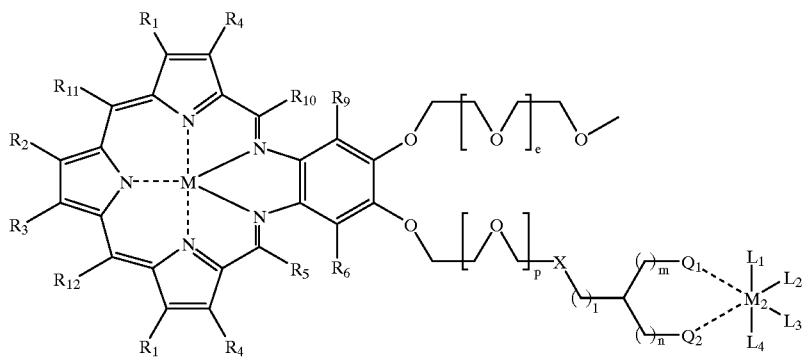
(VIII)
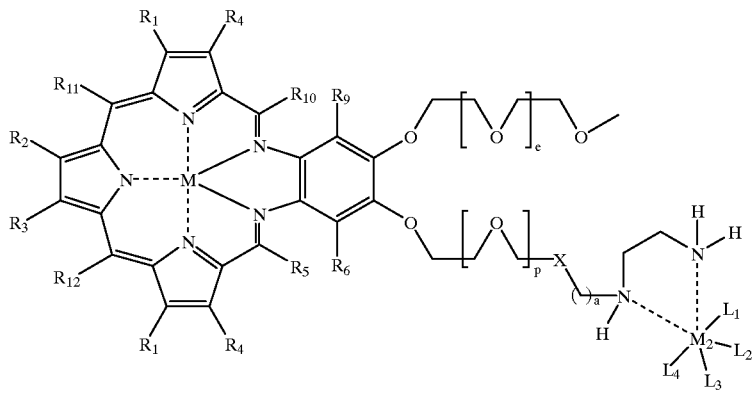

where:

e, f, and g are independently zero or an integer from 1 to 8, preferably 0 to 5, more preferably 1 to 3;

p is zero or an integer from 1 to 5, more preferably from 0 to 2; and $M_2$ is platinum(II) or platinum(IV), which may have from zero to 4 counterions (e.g., "$L_1$–$L_4$"), these counterions being neutral or anionic ligands including but not limited to aqua, ammonia, alkyl or aryl amine, pyridine, substituted pyridine, acetate, gluconate and other carboxylates or dicarboxylates, such as malonate, nitrate, chloride, phosphate, glucose-6-phosphate, and the like.

The chemotherapeutic agents employed in the conjugates of the present invention may, for example, be one of the following: an alkylating agent such as a nitrogen mustard, an ethyleneimine or a methylmelamine, an alkyl sulfonate, a nitrosourea, or a triazene; an antimetabolite such as a folic acid analog, a pyrimidine analog, or a purine analog; a natural product such as a vinca alkaloid, an epipodophyllotoxin, an antibiotic, an enzyme, taxane, or a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of alkylating agents, antimetabolites, natural products, miscellaneous agents, hormones and antagonists are provided below. The types of cancer for which these classes of chemotherapeutic agents are indicated are described in Calabresi, P., et al., "Chemotherapy of Neoplastic Diseases" Section XII, pp 1202–1263 in: *Goodman and Gilman's The Pharmacological Basis of Therapeutics*, Eighth edl, 1990 Pergamin Press, Inc.; and Barrows, L. R., "Antineoplastic and Immunoactive Drugs", Chapter 75, pp 1236–1262, in: *Remington: The Science and Practice of Pharmacy*, Mack Publishing Co. Easton, Pa., 1995; both references are incorporated by reference herein, in particular for treatment protocols.

Alkylating agents include: nitrogen mustards (e.g., Mechlorethamine ($HN_2$), Cyclophosphamide, Ifosfamide, Melphalan, Chlorambucil and Estramustine), etheleneimines and methylmelamines (e.g., Hexamethylmelamine and Thiotepa), alkyl sulfonates (e.g., Busulfan), nitroureas (e.g., Carmustine, Lomustine, Semustine and Streptozocin), and triazines (e.g., Dacarbazine, Procarbazine and Aziridine).

Antimetabolites include: folic acid analogs (e.g., Methotrexate and Trimetrexate), pyrimidine analogs (e.g., Fluorouracil, Floxuridine, Cytarabine and Azacitidine), and purine analogs and related inhibitors (e.g., Mercaptopurine, Thioguanine, Pentostatin and Fludarabine).

Natural products include: Vinca alkaloids (e.g., Vinblastine (VLB), Vincristine and Vindesine), epipodophillotoxins (e.g., Etoposide and Teniposide), antibiotics (e.g., Dactinomycin, Danorubicin, Doxorubicin, 4'-Deoxydoxorubicin, Bleomycin, Pilcamycin, Mitomycin, Neomycin and Gentamycin), enzymes (e.g., L-Asparaginase), taxanes and taxoids (e.g., Docetaxel and Paclitaxel), and biological response modifiers (e.g., Interferon Alpha, Tumor Necrosis Factor, Tumor-Infiltrating Lymphocytes).

Miscellaneous agents include: platinum coordination complexes (e.g., Cisplatin and Carboplatin), anthracenedione (e.g., Mitoxantrone), substituted ureas (e.g., hydroxyurea), methyl hydrazine deravitives (e.g., Procarbazine), and adrenocortical suppressants (e.g., Mitotane and Aminoglutethimide).

Hormones and antagonists include: adrenocorticosteroids (e.g., Predinsone), progestins (e.g., Hydroxy-progesterone caproate, Medroxy-progesterone acetate and Megestrol acetate), estrogens (e.g., Diethylstil-bestrol and Ethinyl estradiol), antiestrogen (e.g., Tamoxifen), androgens (e.g., Testosterone propionate and Fluoxymesterone), antiandrogens (e.g., Flutamide), and gonadotropin-releasing hormone analogs (e.g., Leuprolide and Goserelin).

Nomenclature

The compounds of Formula A are named and numbered as described below with reference to Formula A'.

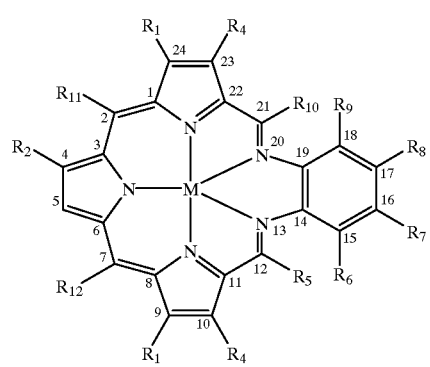

Formula A' according to which, by way of example, the compound of Formula 9 (prepared according to Reaction Scheme A and Example 1) is named cis-Dichloroplatinum(II) complex of gadolinium(III) complex of 4,5-diethyl-10,23-dimethyl-9,24-bis(3-hydroxypropyl)-16-[2-[2-[2-[2-[2-(2-methoxyethoxy)-ethoxy]ethyl]-[1,4-dizacyclohex-1,4-yl] ethoxy]ethoxy]ethoxy]-17-[2-[2-(2-methoxyethoxy) ethoxy]-ethoxy]-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene.

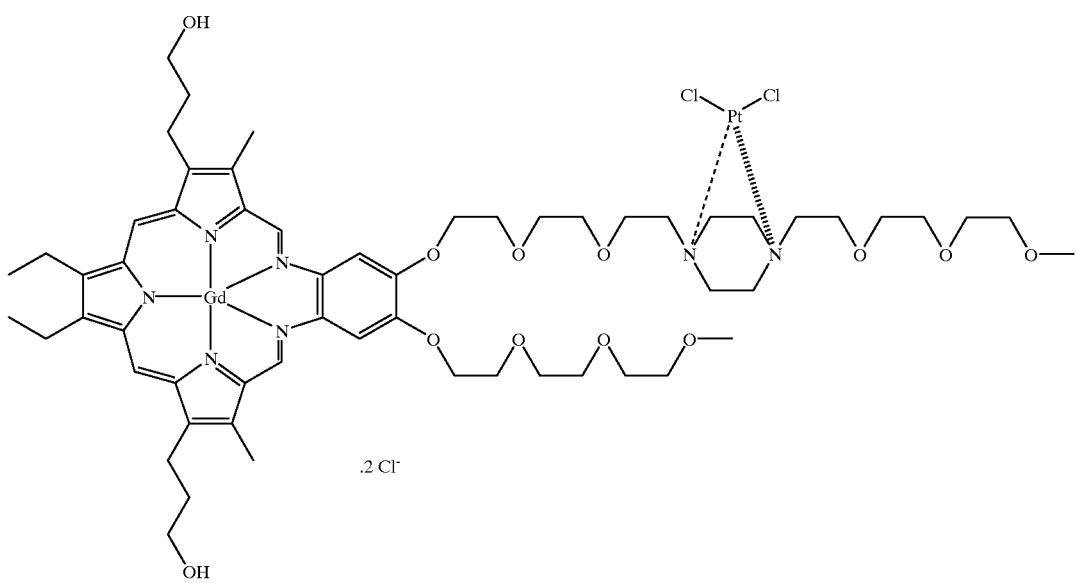

9

.2 Cl⁻

Alternatively, the cis-platinum-piperazine complex of Formula 9 can be incorporated in the chemical name as follows, gadolinium(III) complex of 4,5-diethyl-10,23-dimethyl-9,24-bis(3-hydroxypropyl)-16-[2-[2-[2-[2-[2-(2-methoxyethoxy)ethoxy]ethyl]-[1,4-[cis-dichloroplatinato(II)]diazacyclohex-1,4-yl]ethoxy]-ethoxy]ethoxy]-17-[2-[2-(2-methoxyethoxy)ethoxy]-ethoxy]-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene.

The compound of Formula 41 (prepared according to Reaction Scheme F and Example 6)

is named the cis-dichloroplatinum(II) complex of gadolinium(III) complex of 4,5-diethyl-17-(2-[2-(2-methoxyethoxy)ethoxy]ethoxy)-9,24-bis(3-hydroxypropyl)-16-(2-[2-(2-(2-aminoethyl-amino)ethoxy)ethoxy]ethoxy)-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene; alternatively, giving higher priority to the oxygen substituents at $R_8$, the numbering of the 16 and 17 positions can be reversed.

By way of example of other nomenclature (and numbering) systems, the following texaphyrin molecule (CAS Registry No. 156436-89-4):

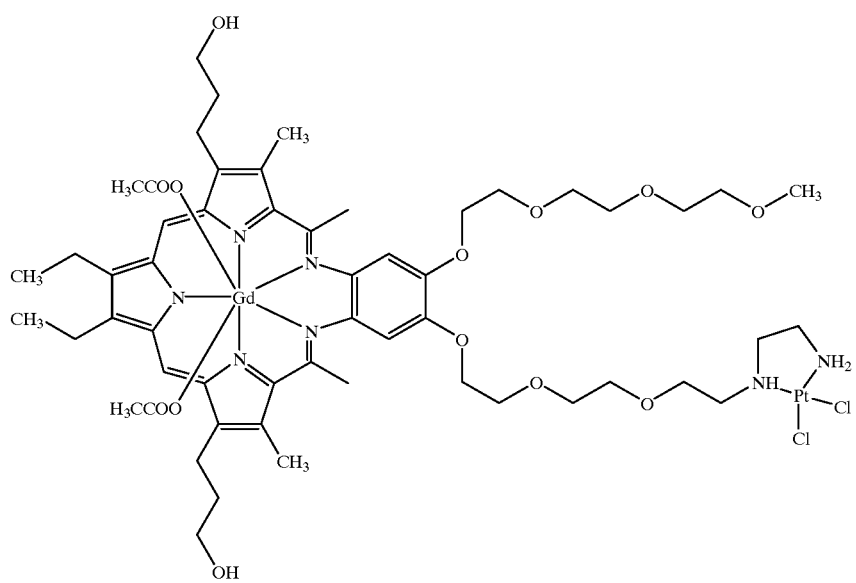

41

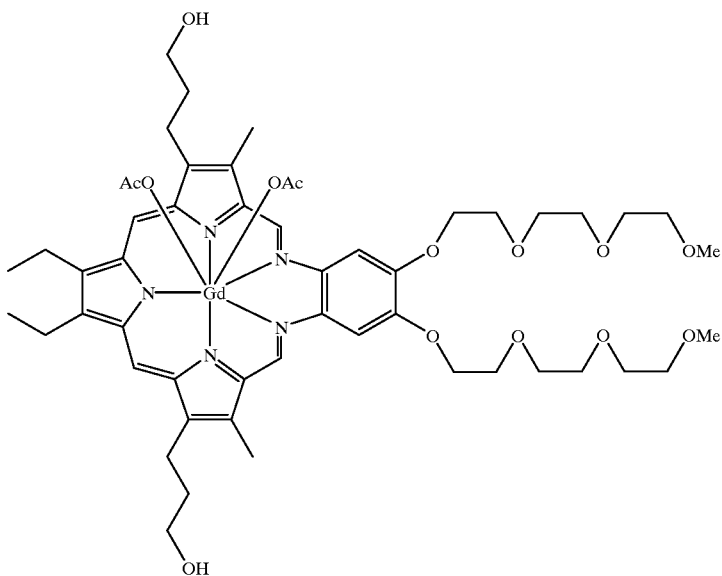

has the Chemical Abstracts name bis(acetato-O)[9,10-diethyl-20,21-bis[2-[2-(2-methoxyethoxy)ethoxy]ethoxy]-4,15-dimethyl-8,11-imino-6,3:13,16-dinitrilo-1,18-benzodiazacycloeicosine-5,14-dipropanolato-N1,N18,N23,N24,N25]gadolinium, and is also called by the trivial names Gadolinium Texaphyrin, Gd texaphyrin and Gd-Tex, has the internal designation PCI-0120 and the trademark XCYTRIN™.

Synthesis of the Compounds of Formula I

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. Other equivalent separation or isolation procedures can, of course, also be used.

Synthesis

Texaphyrin-chemotherapeutic agent conjugates, optionally including a platinum metal chelating site and Pt complexes may be prepared in one of the following ways:

a) "Post-synthetic modification": A suitably functionalized platinum binding site, in either free or masked form, on a platinum(II) or platinum(IV) compound is reacted with an active linking or coupling site on the skeleton of a texaphyrin, which has previously been prepared according to methods known in the art, to give a texaphyrin-platinum compound conjugate.

b) "Pre-synthetic modification": A suitably functionalized platinum binding site, in either free or masked form, on a platinum(II) or platinum(IV) compound is reacted with an active linking or coupling site on either a tripyrrane or a benzene texaphyrin precursor, after which the precursor is carried through the transformational steps needed to generate a texaphyrin, by methods known in the art, to give a texaphyrin-platinum compound conjugate.

Thus, the compounds of Formulae A and C can be prepared, initially by following the procedures described in the previously cited literature, particularly employing the syntheses described below with reference to Reaction Schemes A–H and L–R. The structures illustrated in Reaction Schemes A–H and L–R, while illustrated with specific substituents at $R_1$–$R_{12}$ may be substituted by others of the disclosed substituents stable under the reaction conditions described, as will be apparent to those skilled in the art.

Reaction Scheme A

The synthesis of a texaphyrin-cisplatin conjugate (cpd. 9) utilizing a platnum(II) metal chelating site and following the synthetic scheme shown below in Reaction scheme A, is further described in Example 1.

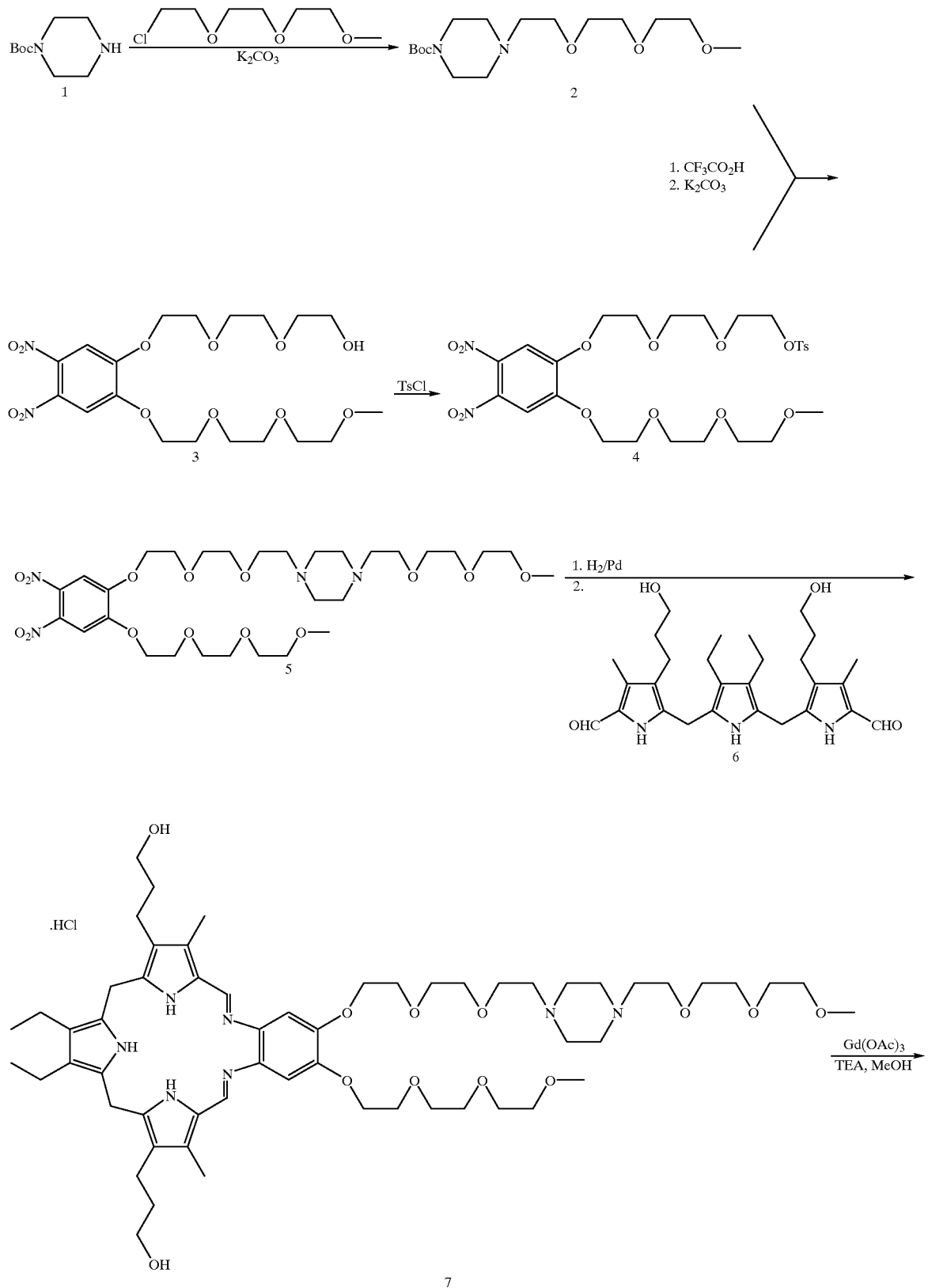

-continued

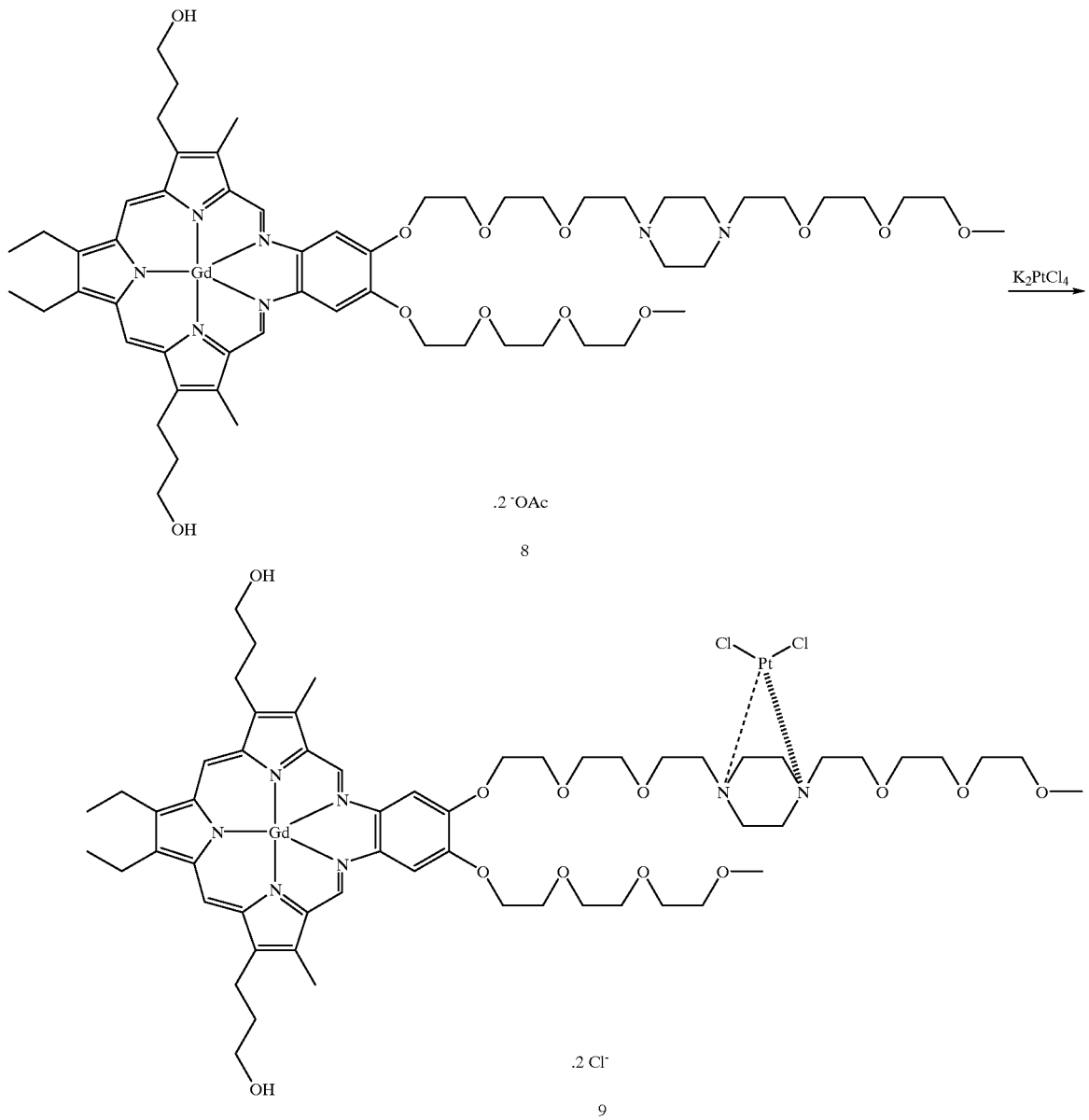

Formula 2

Two equivalents of potassium carbonate and one equivalent of 2-[2-(2-chloroethoxy)ethoxy]ethanol, and N-tert-butyloxycarbonyl-piperazine 1 (Krapcho, A. P., Kuell, C. S. Synth. Commun. 1990, 20, 2559) are suspended in a solvent such as acetonitrile, and the resulting mixture is heated at reflux for 12 hours under an inert, e.g., argon atmosphere. The reaction mixture is allowed to cool to ambient temperature and filtered, e.g., over Celite™ and purified.

Formula 4

Equivalent amounts of 1-methoxy optionallypolyethoxy-2-hydroxy optionally polyethoxy-4,5-dinitrobenzene such as 3 and 4-toluenesulfonyl chloride are dissolved in pyridine at 0° C. The resultant solution is stirred for 18 hours, whereupon solvent is evaporated at reduced pressure. The residue is partitioned between aqueous and organic layers. After separation, the organic layer is washed and dried, followed by removal of solvent.

Formula 5

A compound according to Formula 2 is dissolved in an acidified solvent. The resulting solution is stirred for 6 hours, whereupon solvents are evaporated under reduced pressure and the residue dried in vacuo 1.5 hours. A presumed 1-[2-[2-(2-methoxyethoxy)ethoxy]-ethyl]piperazine bis-trifluoroacetate intermediate is dissolved, e.g., in acetonitrile, and an alkali carbonate, e.g., potassium carbonate is added. The resulting suspension is stirred under an inert atmosphere until the evolution of gas ceases, whereupon a solution of Formula 4 in acetonitrile (30 ml) is slowly added. The reaction mixture is gently heated for 14 hours, then allowed to cool to ambient temperature, isolated and purified to give a piperazinyl dinitrobenzene compound according to Formula 5.

Formula 7

A compound according to Formula 5 is dissolved in an organic solvent, e.g., methanol. Under a strict nitrogen atmosphere a catalyst (e.g., 10% palladium on carbon) is added followed by concentrated hydrochloric acid. The flask is placed on a Parr hydrogenation apparatus at a maintained hydrogen pressure of 40 psi. After 2.5 h an additional amount of catalyst and acid is added to drive the reaction to completion. After a further time, when consumption of hydrogen ceases, the catalyst is removed by filtration and the filtrate is transferred to a vessel containing a tripyrrane such as Formula 6. The reaction is diluted by the addition of solvent (e.g., methanol) and then stirred at ambient temperature under a nitrogen atmosphere. After 18 h the solvent is removed by rotary evaporation under reduced pressure and the residue dried under high vacuum for 15 h to afford Formula 7.

Formula 8

A hydrochloride salt of Formula 7, a metal (e.g., gadolinium) acetate hydrate, triethylamine and methanol are combined and heated under reflux open to the atmosphere. After 6 h air is dispersed through the reaction for 30 minutes. After a further 2 h the reaction is cooled to ambient temperature, filtered, and solvents are removed by rotary evaporation under reduced pressure. After drying under high vacuum the residue is was suspended in a solvent, e.g., acetone, and stirred for 10 minutes at room temperature. Insoluble material is filtered, washed with acetone, and dried under high vacuum. After 15 h the residue is dissolved in methanol and deionized water, and acetic acid washed zeolite (e.g., SAY-54, LZY-54) followed by gentle agitation and removal of the zeolite. The zeolite treatment can be repeated. The resulting solution is was treated with a lower alkanol, e.g., n-butanol to prevent bumping during rotary evaporation, after which the residue is further dried, suspended in acetone and stirred for 10 minutes at ambient temperature. Insoluble material is filtered, washed and dried under high vacuum to afford Formula 8.

Formula 9

A large excess of potassium tetrachloroplatinate(II) is dissolved, e.g., in water in a septum-sealed microvial, heated under argon atmosphere to 45° C., and Formula 8 is added. The reaction mixture is stirred and the desired compound 9 (a compound of the invention pursuant to Formula A) precipitates, is isolated and purified.

Reaction Scheme B

The synthesis of a texaphyrin-cisplatin conjugate (Formula 16) from the corresponding di-amino-methylformate, following the synthetic scheme shown below in Reaction Scheme B, is further described in Example 2.

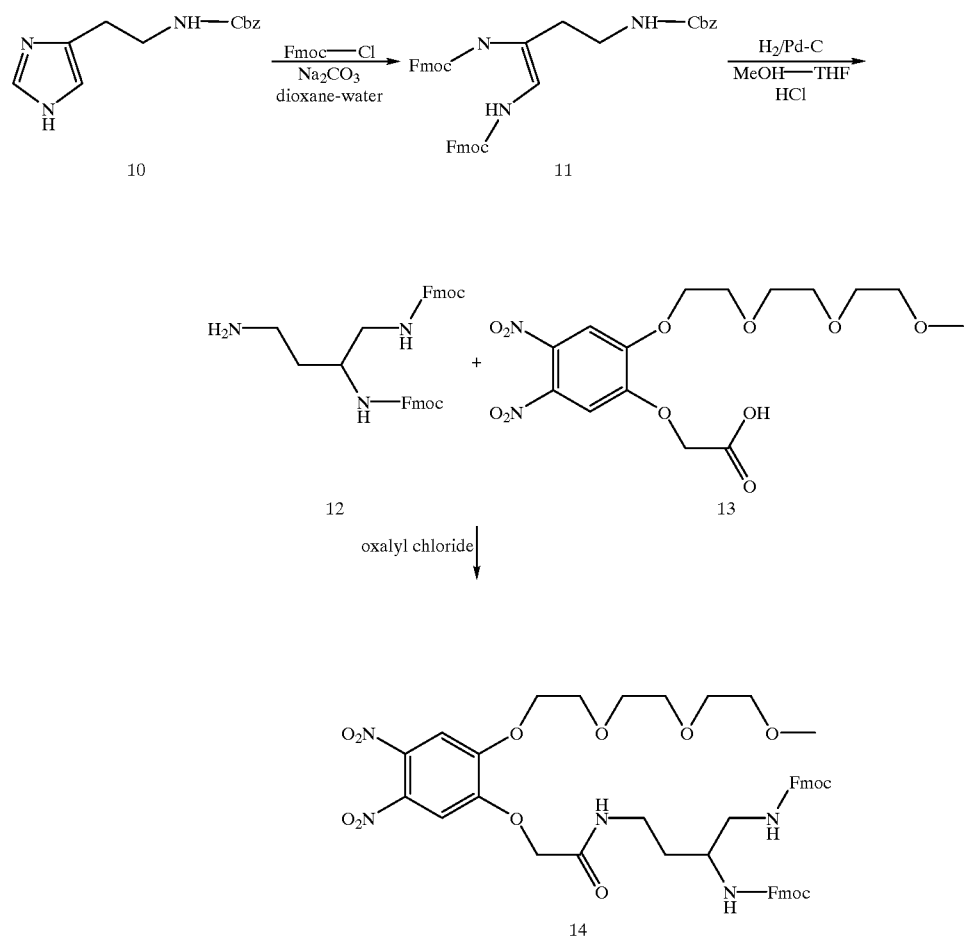

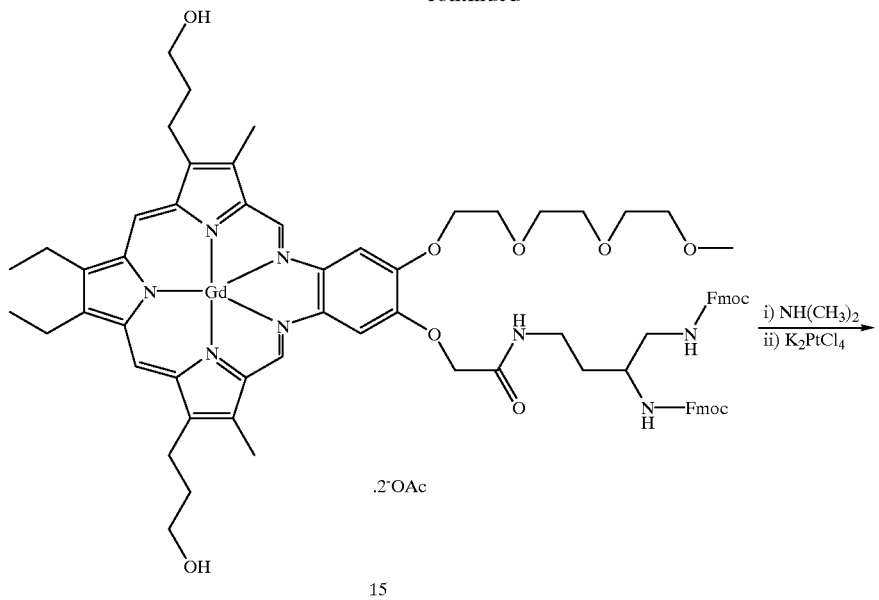

15

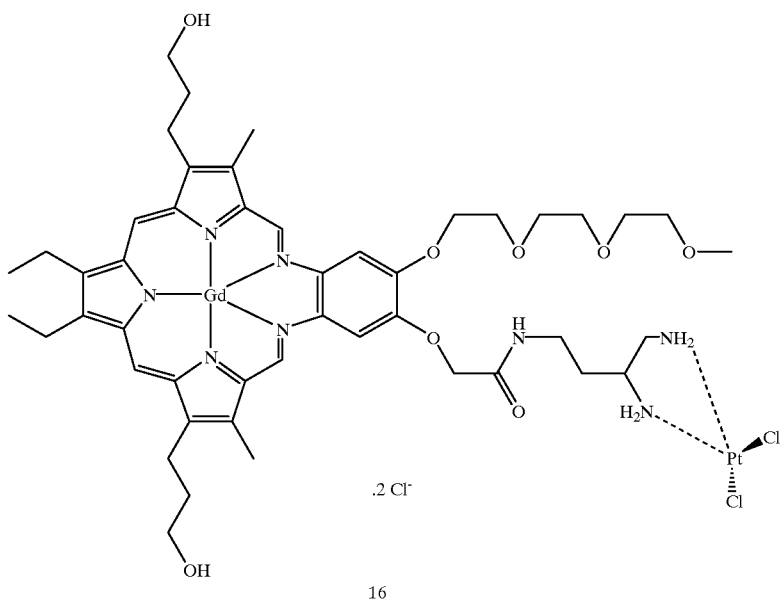

16

Formula 11.

A compound such as Formula 10, benzyloxycarbonyl-[2-(1H-imidazol-4-yl)ethyl]amine, prepared according to Altman et al. (Z. *Naturforsch. B*. 46:1473–1488 (1991)), is dissolved and a saturated solution of sodium carbonate is added, followed by heating, cooling and the addition of 9H-fluorene-9-yl-methyl chloroformate ("Fmoc-Cl").

Formula 12

A compound of Formula 11 is hydrogenated employing a catalyst, e.g., 10% Pd on carbon. In a dry vessel, 4,5-dinitrocatechol and K2CO3 are combined in absolute methanol under nitrogen atmosphere, and triethylene glycol monomethyl ether tosylate is added and the resulting suspension heated to reflux, isolated and purified. With this is combined a slight excess of ethyl-2-iodoacetate and potassium carbonate and acetonitrile, with heating to reflux, for 6.5 hours. The reaction mixture is partitioned and the organic phase washed, isolated, dried and purified to give the corresponding compound of Formula 12.

Formula 13

An aqueous solution of and alkali base, e.g., sodium hydroxide, is added to a solution of Formula 12 in e.g., tetrahydrofuran (THF), and stirred followed by evaporation of the THF. The resulting aqueous solution is washed, neutralized with aqueous acid, separated and the resulting oil is freeze-dried. The resulting solid was dissolved, washed, isolated and purified to give Formula 13.

Formula 14.

A compound of Formula 13 is suspended in a solvent together with N,N-dimethylformamide (0.1 mL), and oxalyl chloride in dichloromethane is slowly added with stirring under a slow stream of argon. When the evolution of gas ceases, the reaction vessel is covered by septum and stirred at room temperature for 6 h. The reaction mixture is then evaporated in vacuo and dried in high vacuum. The reaction vessel is then covered by septum and a mixture of benzene and dichloromethane is added through the septum, with slow stirring. After 0.5 h, the stirring is discontinued and the crude acid chloride is taken up via syringe and added through a septum to an ice/water cooled solution of approximately an equivalent amount of Formula 12, e.g., in a mixture of dichloromethane-pyridine. The reaction mixture is stirred, quenched e.g., with 0.1 M aqueous hydrochloric acid, diluted by chloroform and washed by ice-cold aqueous 0.5 M hydrochloric acid. The organic layer is washed, dried, and evaporated in vacuum, and purified to give 14.

Following the procedures of Reaction Scheme 1, a dinitrobenzene compound of Formula 14 is converted to the corresponding diaminobenzene, which is reacted with a tripyrrane of Formula 6 to give the corresponding $sp^3$ nonaromatic macrocycle. This macrocycle is then oxidized and metallated with gadolinium acetate hydrate to give the gadolinium(III) complex 15, which is then treated with dimethylamine in a tetrahydrofuran-methanol mixture with stirring overnight at 0° C. to remove the Fmoc protecting groups. The resulting Gd(III)-texaphyrin is reacted with potassium tetrachloroplatinate(II) to give the cis-dichloroplatinum(II) complex of Formula 16.

Reaction Scheme C

The synthesis of texaphyrin-cisplatin diamine conjugates (cpd.s 21 and 22), utilizing a dicarboxylate platinum(II) metal chelating site and following the synthetic scheme shown below in Reaction Scheme C, is further described in Example 3.

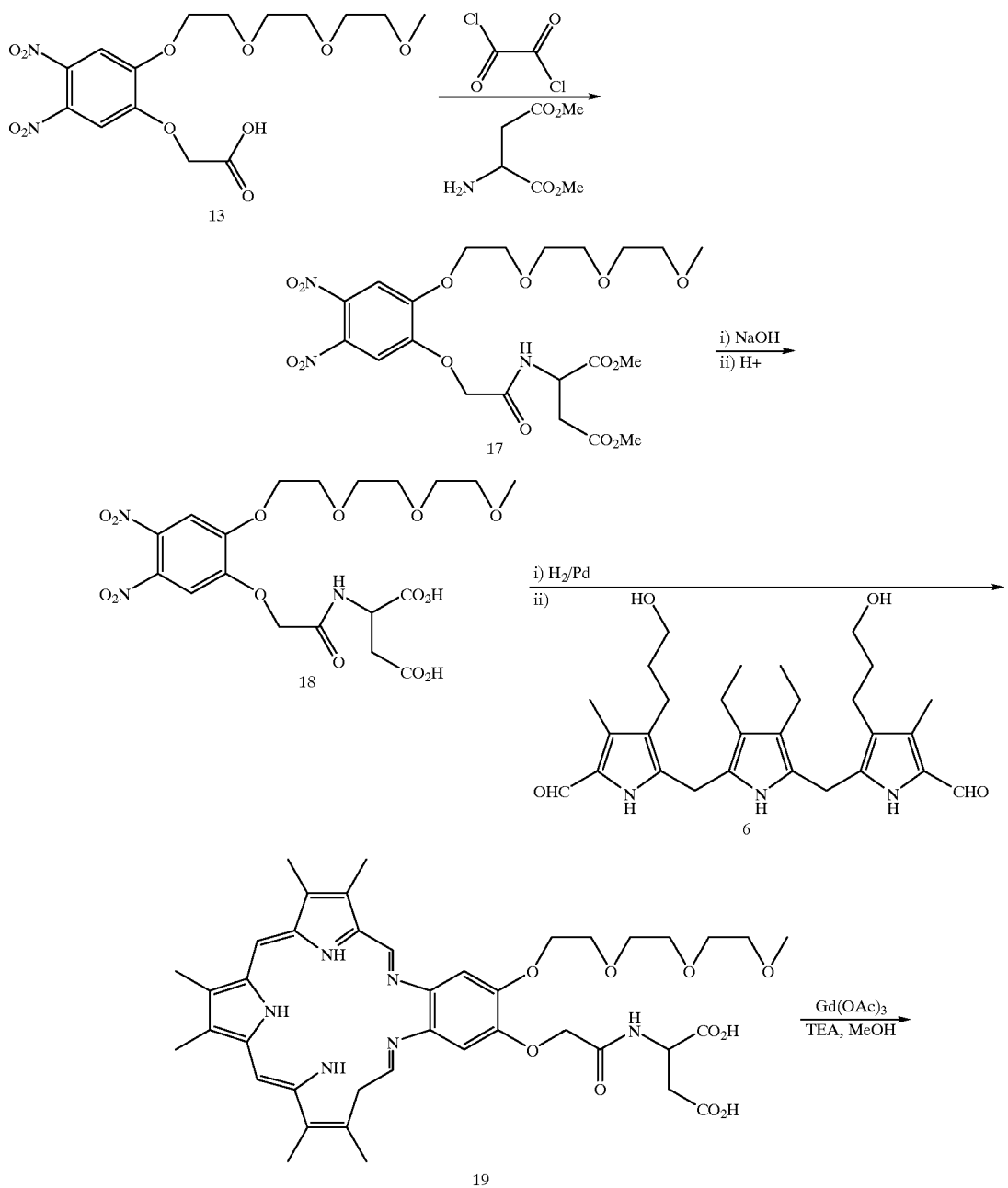

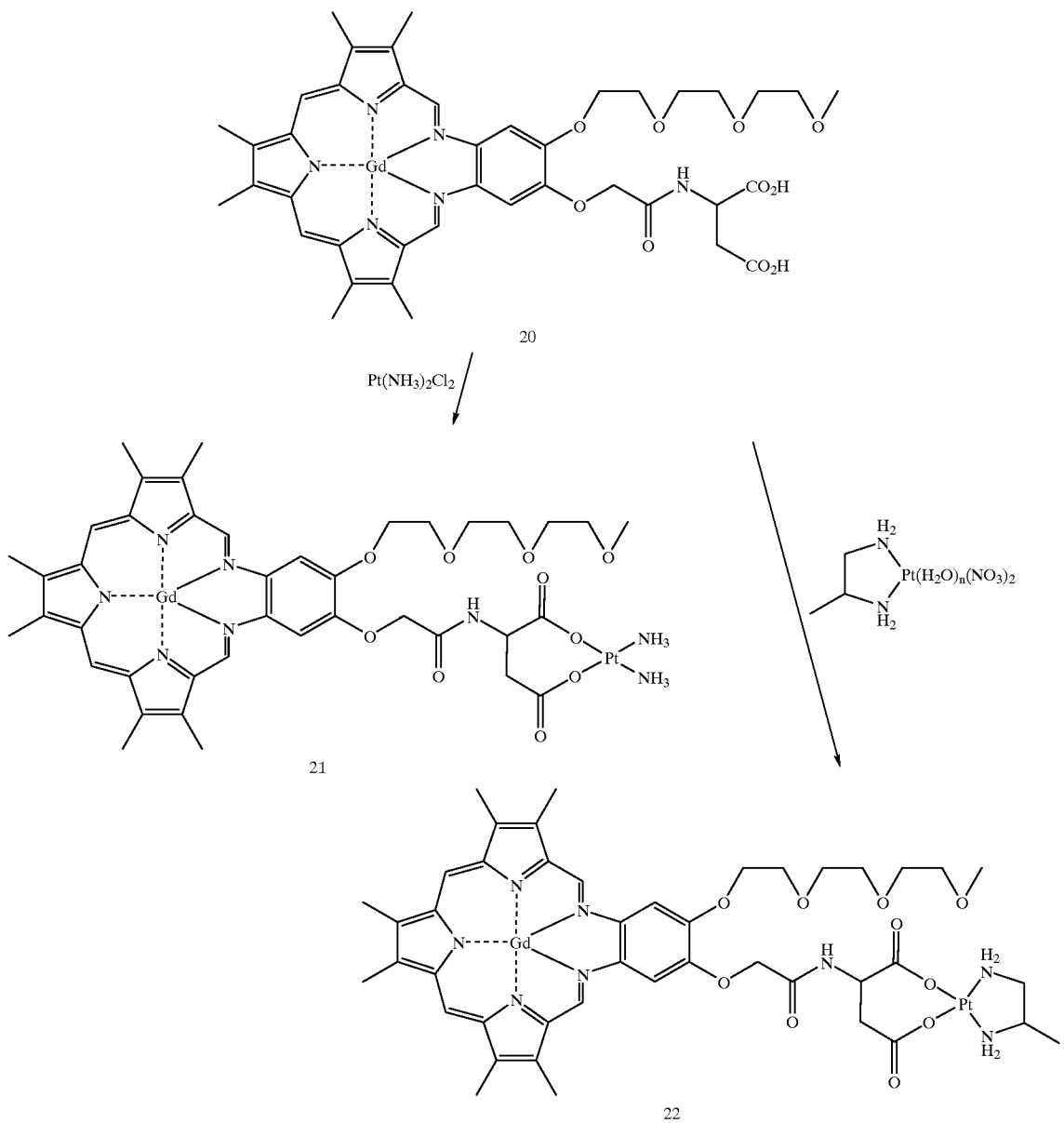

Formula 17.

Under argon, a compound of Formula 13 is suspended in a solvent, adding N,N-dimethylformamide slowly, followed by dropwise addition of a dichloromethane solution of oxalyl chloride. When the evolution of gas ceases, the reaction vessel is covered and stirred. The volatiles were then evaporated and the remaining solids dried. The reaction vessel is then covered and a mixture of benzene and dichloromethane added upon slow stirring. The crude acid chloride is taken up via syringe and added to a solution of dimethyl aspartate in dichloromethane-pyridine. The reaction mixture is stirred overnight and partitioned between chloroform and ice-cold 10% aqueous citric acid. The organic layer is washed, dried, evaporated and purified, to give a dimethyl ester of Formula, 17 that is subsequently dissolved in ethanol-tetrahydrofuran mixture and aqueous sodium hydroxide added. The reaction mixture is stirred at room temperature for 3 days. The solution is then acidified and the product of Formula 18 is extracted with dichloromethane, washed, dried and the solvent evaporated.

Following the procedures described with reference to Reaction Scheme A, the resulting dinitrobenzene compound 18 is converted to the corresponding diaminobenzene, which is reacted with tripyrrane 6 in isopropyl alcohol to give the $sp^3$ nonaromatic macrocycle, 19. This macrocycle is then oxidized and metallated with gadolinium acetate hydrate to give the corresponding Gd(III) complex, 20.

The di-acid gadolinium complex 20 is platinated by reaction of $Pt(NH_3)_2Cl_2$ in dimethyl sulfoxide (DMSO) to yield the cis-platin conjugate complex, 21. Alternatively, a diamine platinum complex, 22, is synthesized by adding an aqueous (or DMSO) solution of the gadolinium complex 20 to an aqueous solution of (1,2-diaminopropane)Pt(II)(NO$_3$)$_2$ (prepared from (1,2-diaminopropane)PtI$_2$ synthesized from K$_2$PtCl$_4$, (both preparations according to Rochon, F. D.; Kong, P. C. *Can. J. Chem.* 1986, 64, 1894).

Reaction Scheme D

The synthesis of texaphyrin-doxorubicin carboxamide-linked conjugates (cpds. 24), following the synthetic scheme shown below in Reaction Scheme D, is further described in Example 4.

Amide-linked Gd(III)Texaphyrin-Adriamycin Conjugate dicyclohexylcarbodiimide are dried under high vacuum for 18 h in with stirring. Crystalline adriamycin hydrochloride is rinsed into the reaction vessel using, e g., anhydrous dimethylformamide. The temperature of the reaction is increased to 30° C. Reaction completion is monitored, e.g., by HPLC analysis, and when the target peak reaches the desired maximum (e.g., 64%) the reaction is allowed to cool to room temperature and quenched by slow addition in to ether. A resulting precipitate is isolated and purified to give the desired compound.

Reaction Scheme E

The synthesis of a texaphyrin-distamycin conjugate (cpd. 30), at a carboxylic acid substituent, following the synthetic

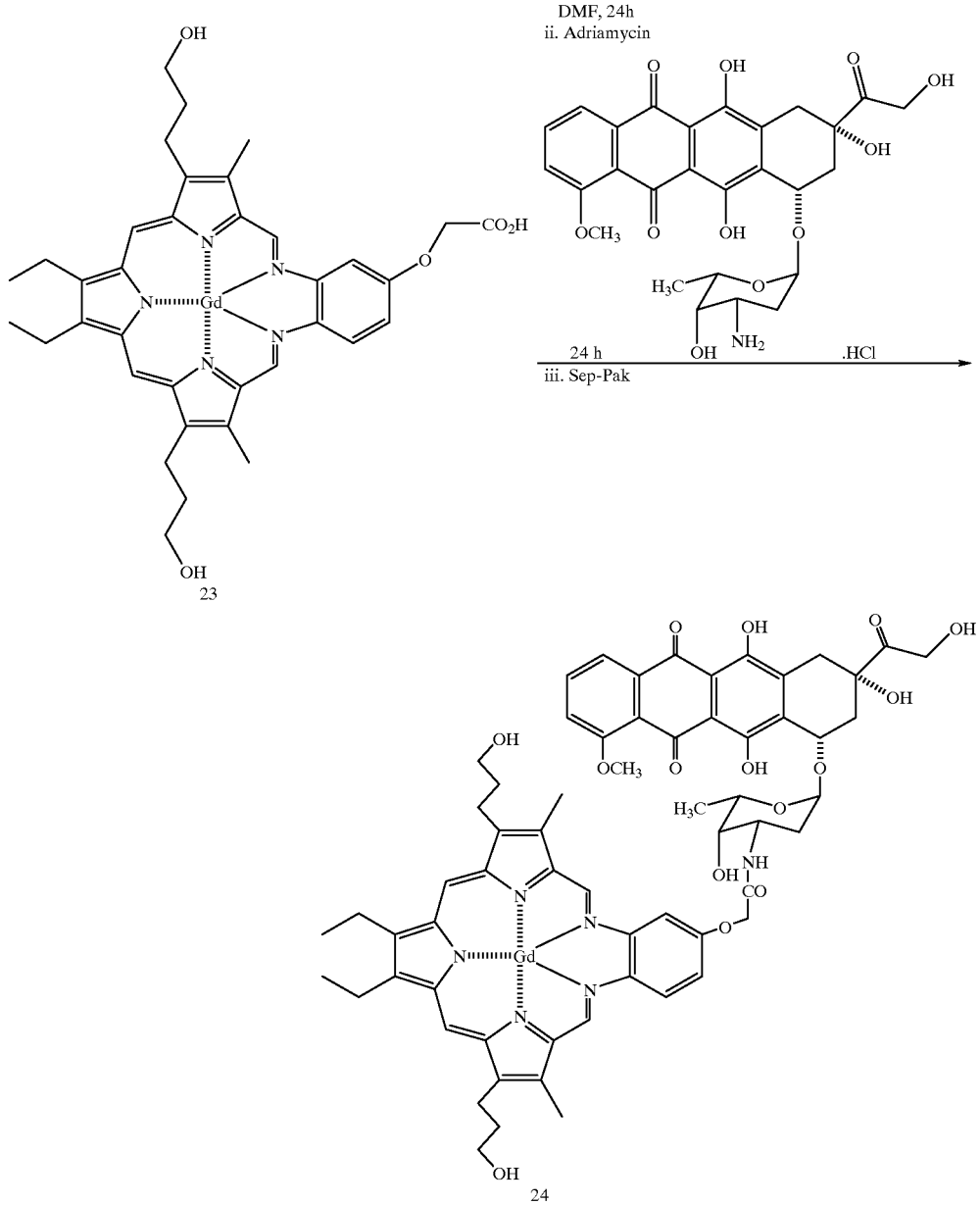

A carboxyalkoxy-texaphyrin complex such as Formula 23, N-hydroxysuccinimide, and 1,3- scheme shown below in Reaction Scheme E, is further described in Example 5.

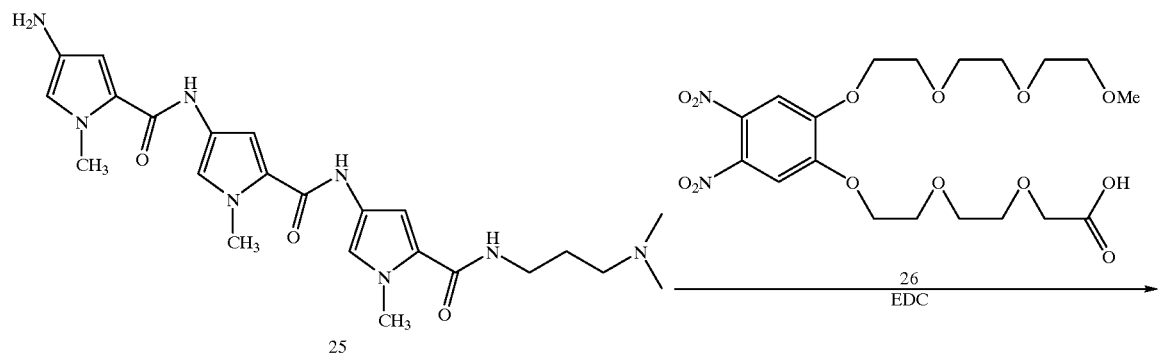
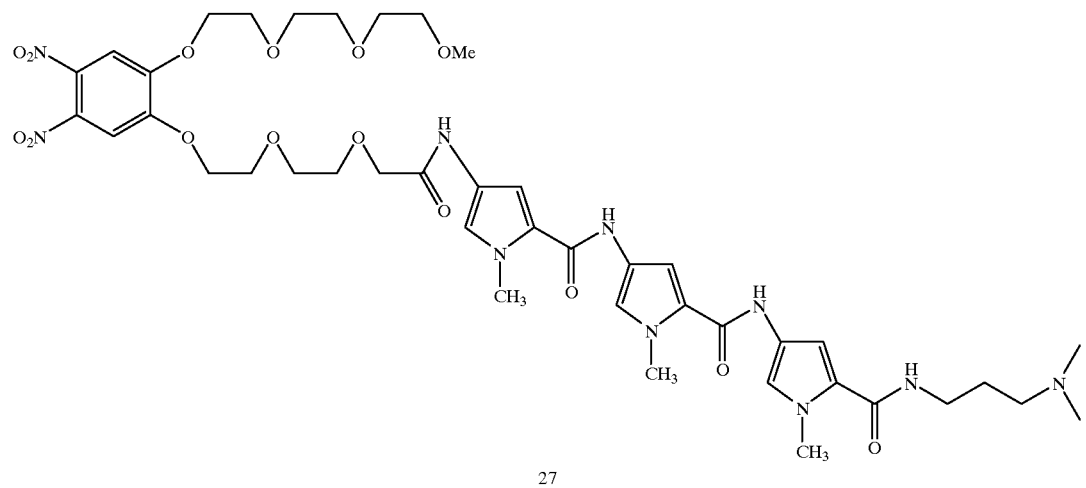
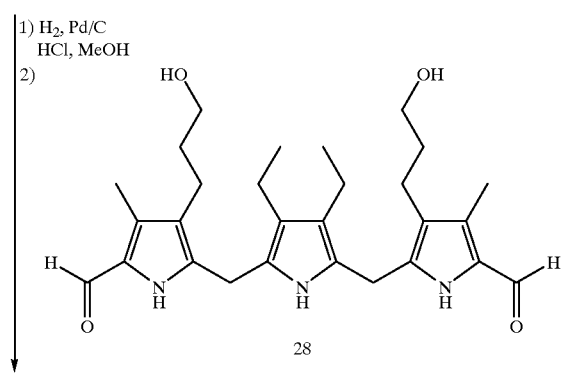

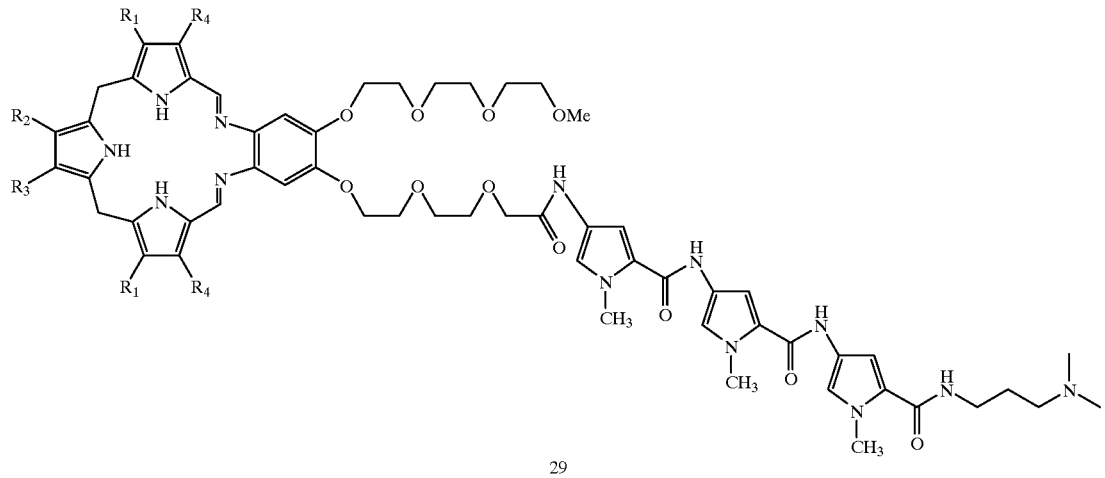

$R_1 = (CH_2)_3 OH$
$R_2 = R_3 = Ethyl$
$R_4 = Methyl$

29

Lu(OAc)XH$_2$O
Et$_3$N, MeOH, air

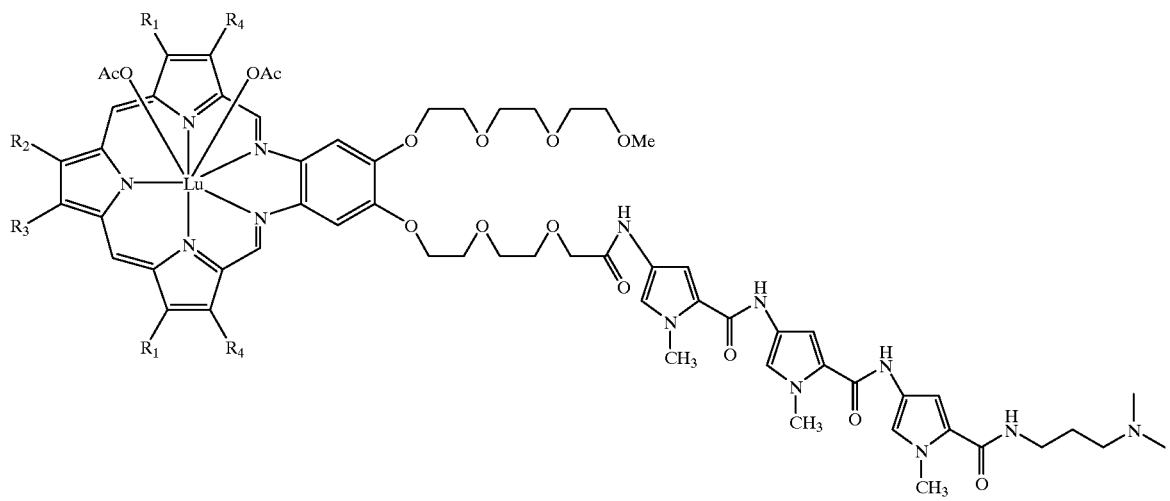

$R_1 = (CH_2)_3 OH$
$R_2 = R_3 = Ethyl$
$R_4 = Methyl$

30

Formula 27

Aminodistamycin 25 is obtained by a reduction of nitrodistamycin according to a procedure previously described (Taylor, J. S.; Schultz, P. G.; Dervan, P. B. *Tetrahedron* 1984, 40, 457–465). After reduction with Pd/C, the crude solution of 25 in anhydrous DMF is filtered. A di-nitro-polyethoxy functionalized monocarboxylate such as 26 is added, followed by dry pyridine. A solution of EDC in anhydrous DMF is then added, followed by HOBt. The resulting reaction mixture is stirred at room temperature under argon in the absence of light for about 12 hours. The solvents are then evaporated and the product purified to give Formula 27.

Formula 30

A hydrogenation catalyst (e.g., 10% palladium on carbon) is suspended in a lower alkanol solvent, to which a compound of Formula 27 is added with additional solvent and an acid. The mixture is hydrogenated at 50 psi until the reaction is complete (e.g., as shown by color change) colorless. The resulting diamine is filtered and used without further purification. To this, a compound of Formula 28 and a lower alkanol are added and the suspension is heated to 45–50° C. for 1.5 h. (Sessler, J. L., Mody, T. D., Hemmi, G. W., Lynch, V. *Inorg. Chem.* 1993, 32, 3175–3187; Young, S. W., Woodburn, K. W., Wright, M., Mody, T. D., Fan, Q., Sessler, J. L., Dow, W. C., Miller, R. A. *Photochem. Photobiol.* 1996, 63, 892–897). The reaction is monitored, e.g., by tlc (i.e., appearance of nonaromatic macrocycle 29) and UV/vis absorption (372 nm). The resulting solution is concentrated to dryness, and the resulting solid is dried. Formula 29 is used without further purification.

The macrocyclic ligand 29 is then oxidatively metallated using a metal acetate hydrate and triethylamine in air-saturated lower alkanol at reflux (~7 h). (Young et al., ibid.). After completion of the reaction (as judged by the optical spectrum of the reaction mixture and tlc), the solution is cooled to room temperature, filtered, and the solvent is removed under reduced pressure and dried in vacuo for 12 h. The resulting solid is suspended, e.g., in acetone, stirred for 20 min at room temperature, and then filtered to wash away any impurities (e.g., incomplete oxidation products and excess triethylamine). The crude complex is dissolved into a lower alkanol, and to the resulting solution is added water and acetic acid-washed zeolite (SAY-54, LZY-54). The resulting mixture is agitated or shaken for 2 h, then filtered to remove the zeolite. The zeolite cake is rinsed, e g., with MeOH and the rinse solution added to the filtrate. The filtrate is concentrated to dryness and purified to afford the corresponding texaphyrin conjugate of Formula 30.

Reaction Scheme F

The synthesis of a gadolinium(III) texaphyrin cis-diaminodichloroplatinum(II) conjugate, following the synthetic scheme shown below in Reaction Scheme F, is further described in Example 6.

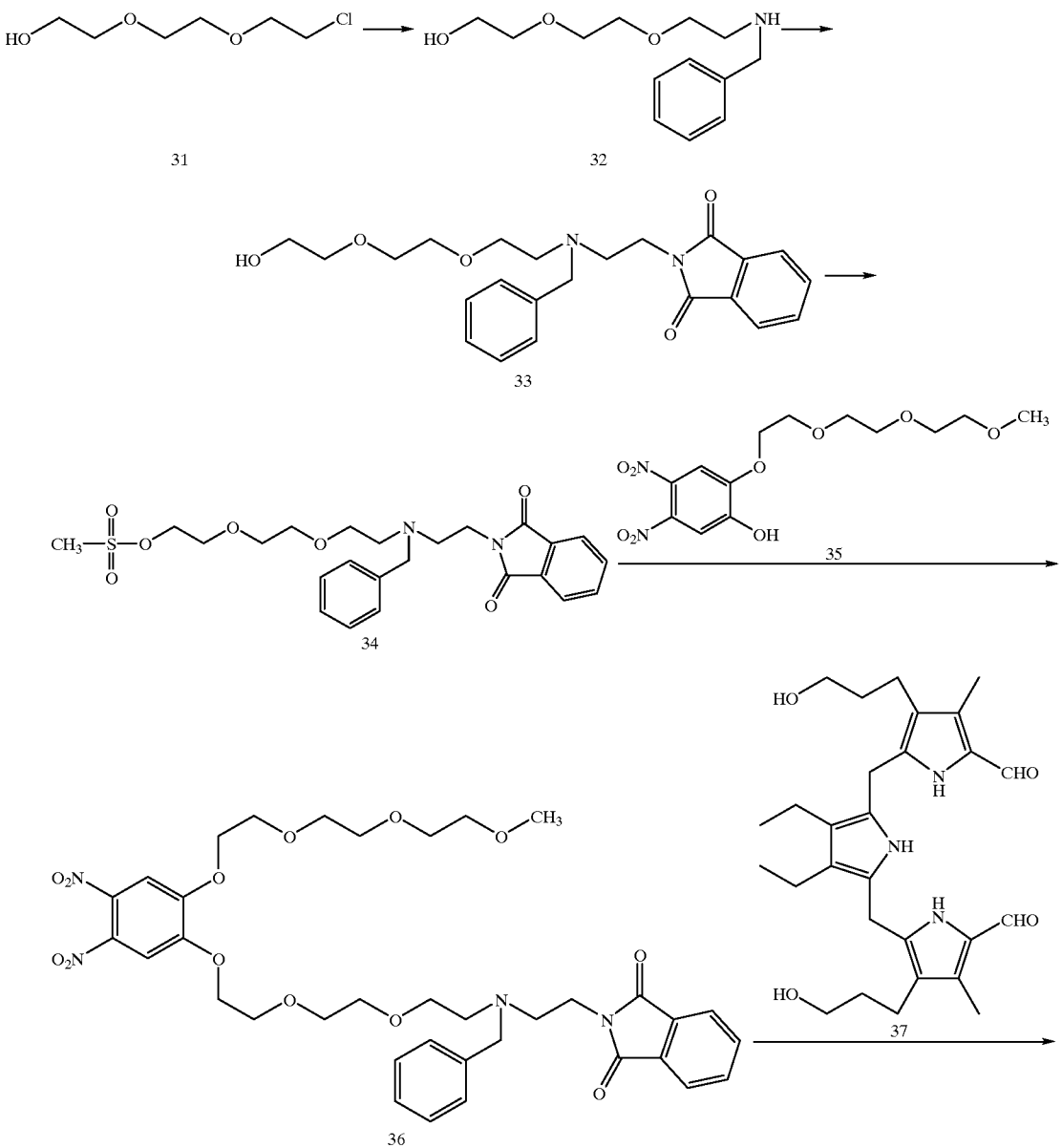

-continued
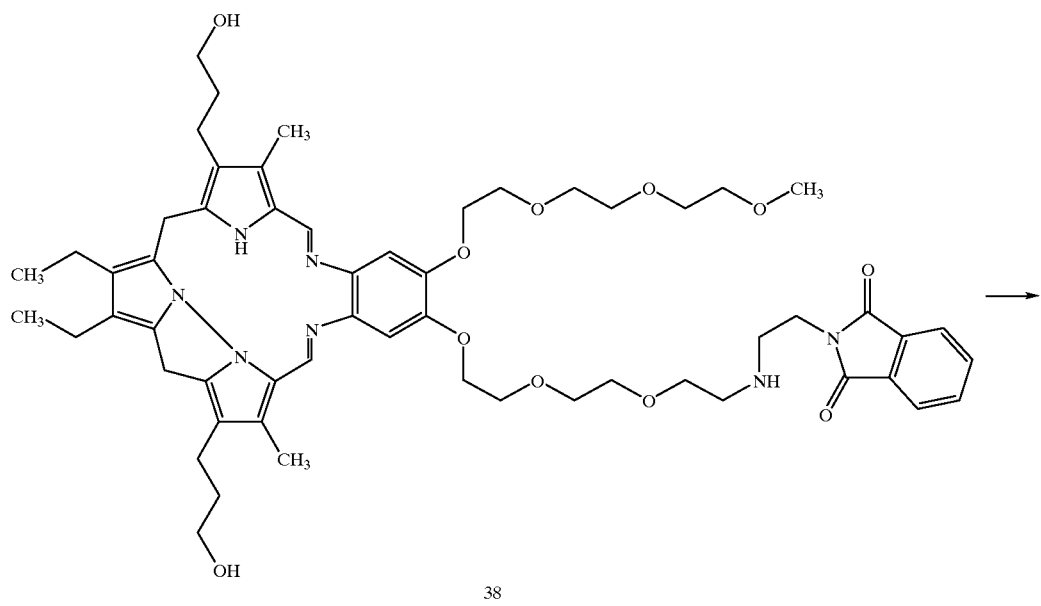
38
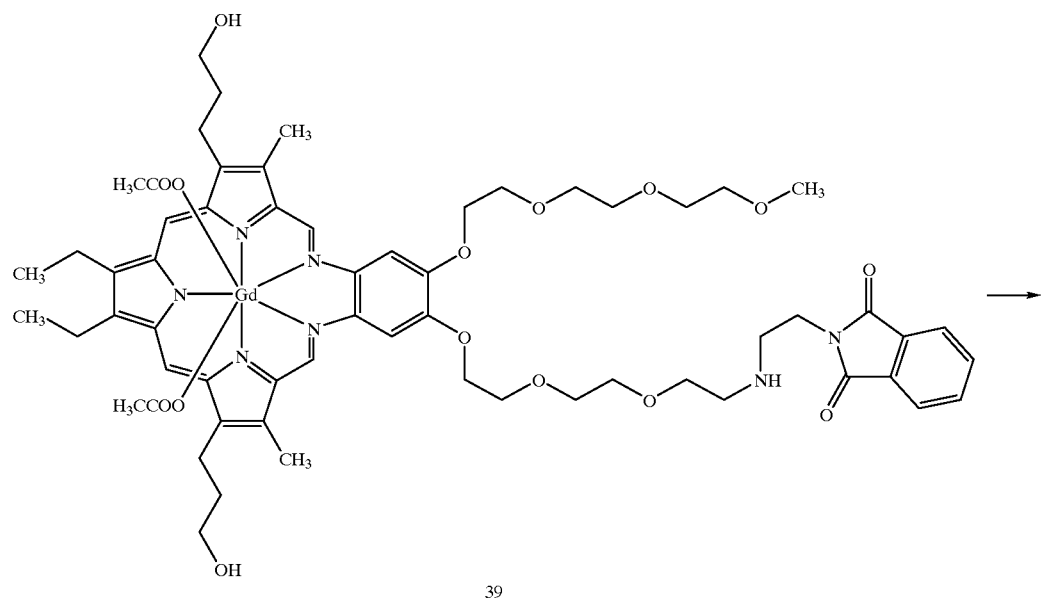
39

-continued

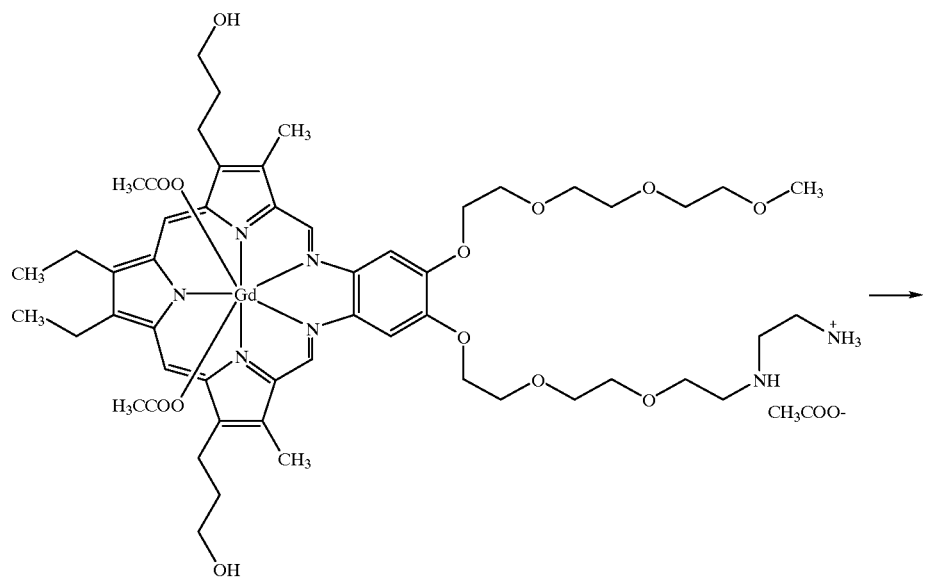

40

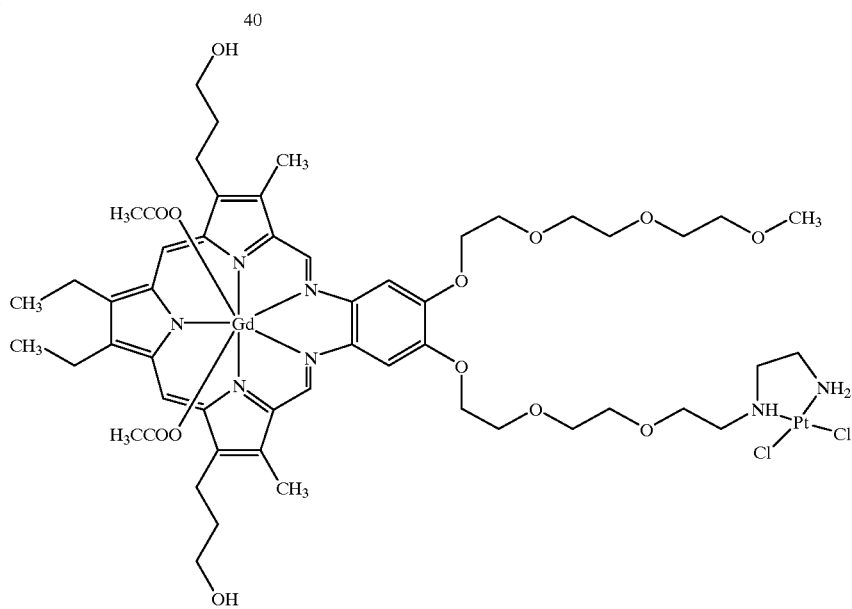

41

Formula 32

A haloalkoxyalkanol such as Formula 31 and benzylamine are dissolved, e.g., in absolute acetonitrile followed by the addition of potassium carbonate. The resulting suspension is heated at reflux with vigorous stirring under an argon atmosphere for 18 hours. The suspension is allowed to cool to room temperature, diluted, e.g., with acetonitrile and filtered. The solvent is removed under reduced pressure and the unreacted benzylamine distilled off under high vacuum. The resulting product is purified and dried to give the corresponding compound according to Formula 32.

Formula 33

A benzylaminoalkoxyalkanol such as Formula 32 is contacted with 2-bromoethyl-phthalimide under the conditions described above for Formula 32 to give the corresponding compound of Formula 33.

Formula 34

A benzylalkoxyalkylaminoalkylphthalimide such as Formula 33 is dissolved, e.g., in mixture of pyridine and dichloromethane, and cooled. Methanesulfonyl chloride is added and the resulting solution stirred at 0° C. for 16 h. (The progress of the reaction can be followed by TLC.) Saturated aqueous sodium bicarbonate is added, and after 30 min of stirring, the organic phase is washed, e.g., with hydrochloric acid and again with saturated aqueous sodium bicarbonate. The solution is dried, the solvent is removed under reduced pressure, and the resulting compound of Formula 34 is used in the next step without further purification.

Formula 36

An alkoxy-polyethoxy-dinitrophenol such as Formula 35 and a mesylate of Formula 34 are dissolved, e.g., in acetonitrile. Potassium carbonate is added and the resulting suspension heated at reflux with vigorous stirring under an argon atmosphere for 48 hours. The suspension is allowed to cool to room temperature, diluted, e.g., with acetonitrile and filtered. Solvent is removed under reduced pressure and the crude product purified. Remaining solvent is removed under reduced pressure, and the residue dried in vacuo to provide the corresponding compound of Formula 36.

Formula 38

A dinitro compound of Formula 36 is dissolved, e.g, in a lower alkanol, concentrated hydrochloric acid is added, and the resulting solution transferred to a Parr flask containing Peariman's catalyst under a strict nitrogen atmosphere. The flask is placed on a Parr hydrogenation apparatus and hydrogen pressure maintained at ca. 50 psi for 14 h. Catalyst from light. A resulting precipitate is filtered, washed, dried in vacuo, and concentrated under reduced pressure to provide the corresponding texaphyrin-cis-platinum complex of Formula 41.

Reaction Scheme G

The synthesis of a texaphyrin-bis-N-heterocyclic conjugate at unprotected hydroxy substituents, following the synthetic scheme shown below in Reaction Scheme G, is further described in Example 7.

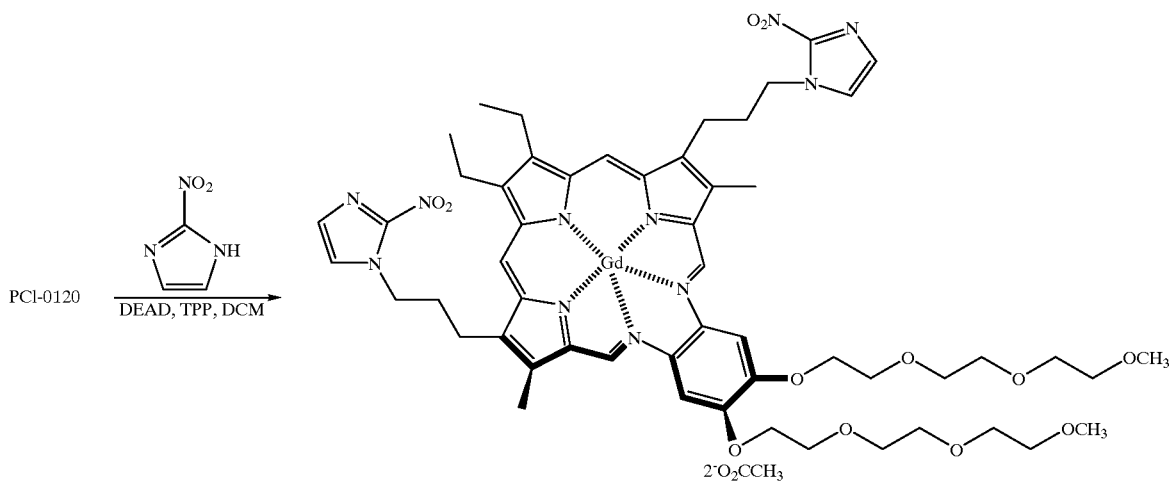

is removed by filtration under an inert atmosphere. The solution is transferred to a flask containing a suspension of a tripyrrane of Formula 37 in a lower alkanol, and stirred for 14 hours. Solvent is removed under reduced pressure and the residue dried in vacuo to provide the crude compound of Formula 38.

Formula 39

A hydrochloride salt of Formula 38, a metal (e.g., gadolinium) acetate hydrate, triethylamine and a lower alkanol are combined and heated at reflux open to the atmosphere. After 4 h the reaction is cooled to room temperature, solvents are removed under reduced pressure and the residue is dried in vacuo to afford the title metallated complex of Formula 39.

Formula 40

A metallated texaphyrin complex of Formula 39 is dissolved, e.g., in a lower alkanol and 40% aqueous methylamine and stirred at ambient temperature for 1 h. Solvents are removed under reduced pressure and the residue dried in vacuo for about 14 hours. The residue is dissolved in ammonium acetate buffer, pH 4.3 and the buffered solution of crude complex filtered, isolated and purified to give the corresponding complex of Formula 40 (having a Pt metal chelating site according to Formula III).

Formula 41

A lower alkanolic solution of a metallated texaphyrin complex having a Pt metal chelating site as illustrated in Formula 40 is added slowly to an aqueous solution of $K_2PtCl_4$. The reaction mixture is allowed to stand at room temperature for 14 hours (e.g., overnight) with protection A hydroxy-substitued, metallated texaphyrin (such as the compound identified as Gd-Tex or PCI-0120) and 2-nitroimidazole are dried together in vacuo. Dry dichloromethane is added under nitrogen atmosphere with stirring to form a solution, which is then cooled. Diethylazodicarboxylate is slowly added, and the solution stirred at 0° C. for 5 h. A lower alkanol is added, then removed under reduced pressure. Trichloromethane is added to form a solution, which is washed with 1M ammonium acetate buffer, pH 4.3 and water. Solvent is removed under reduced pressure, whereupon triethylamine is added to form a solution, which is slowly added into stirred $Et_2O$. The resulting precipitate is isolated and purified to provide the corresponding bis-N-heterocyclic conjugate.

Reaction Scheme H

The synthesis of a texaphyrin-bis-nucleotide conjugate at unprotected hydroxy substituents, following the synthetic scheme shown below in Reaction Scheme F, is further described in Example 8.

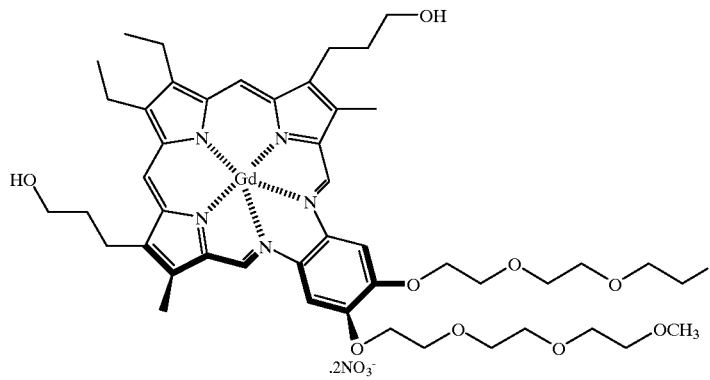
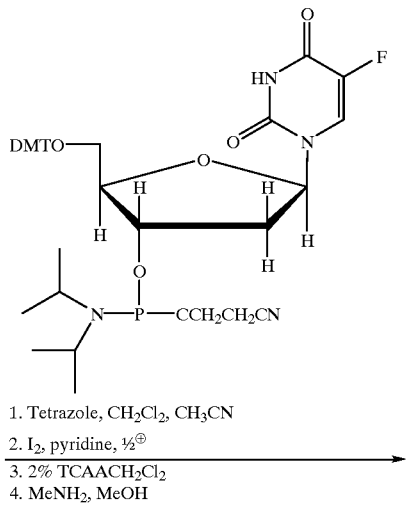
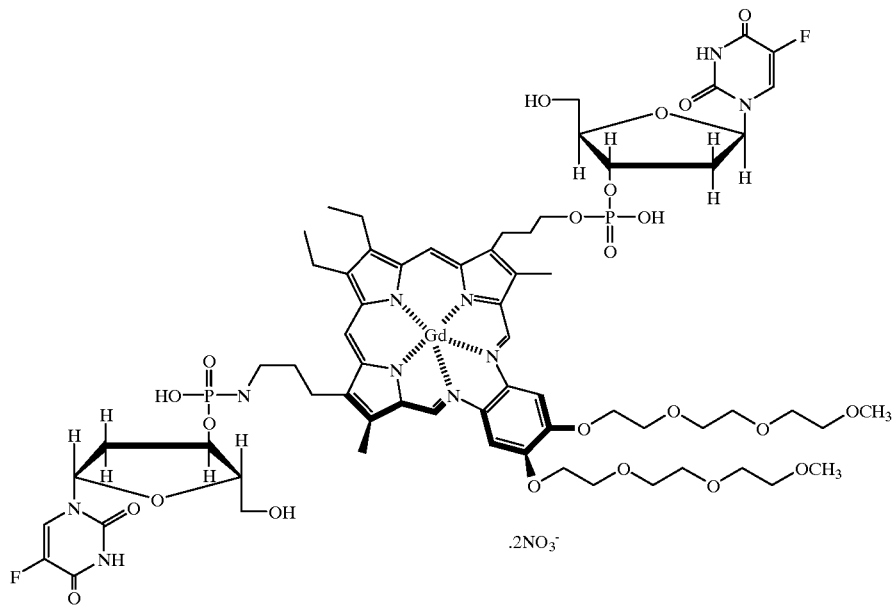

A hydroxy-substitued, metallated texaphyrin (such as the compound identified as Gd-Tex or PCI-0120) and an optionally-substituted nucleotide phosphoramidite (e.g., 5-fluoro-2'-deoxyuridine-3'-[bis-(diisopropylamino)-2-cyanoethyl]-phosphoramidite from Glen Research, Sterling, Va.) are dissolved in solvent. A solution of 1H-Tetrazole is added, and the solution allowed to stir. The resulting solution is washed with iodine solution, e.g., in THF/H2O/pyridine (7:2:1) and with water. Trichloroacetic acid (e.g., 3% solution in dichloromethane) is added, and the resulting solution washed with water. Solvent is removed under reduced pressure, and the residue is dissolved, e.g., in methanol/40% aqueous methylamine (1:1). The solvents are removed (e.g., methylamine is removed with a stream of dry nitrogen whereupon methanol and remaining traces of methylamine are removed under reduced pressure). A lower alkanol (e.g., methanol) and 1M ammonium acetate buffer, pH 4.3 is added to the resulting suspension to form a solution. The buffered solution of crude bis-nucleotide conjugate is isolated and purified. (NOTE: Reaction Schemes I, J and K have been omitted intentionally.)

Texaphyrin-Taxol Conjugates Reaction Schemes
L–R

3-N substitution of the Taxol Framework (Schemes L and M)

Scheme L
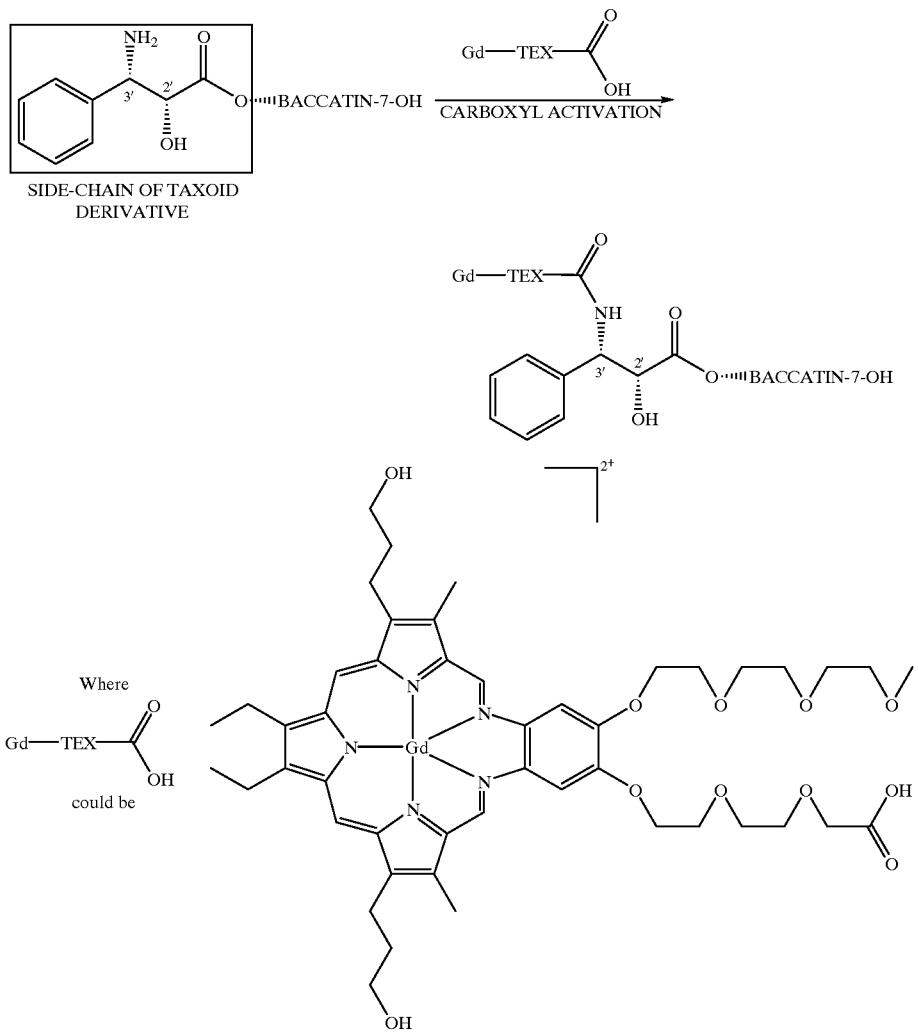
3'-Debenzoyl-taxol can be prepared relatively easily (on a taxol scale) according to the procedure of Didier et al. [Didier E., Fouque E., CommerAon A.: Tetrahedron Lett. 35, 3063 (1994)]. Once prepared, it can be acylated using a suitable activated texaphyrin carboxylic acid as shown above in Scheme L, e.g., following the procedures described in Example 5.
Scheme M
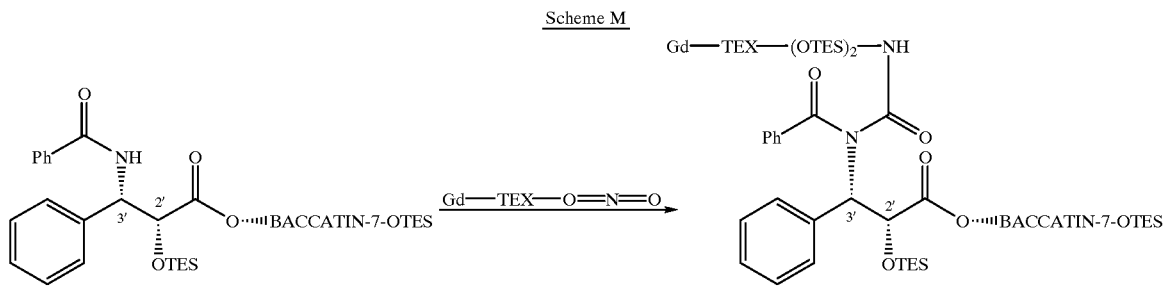

where and

Gd—TEX—O=N=O could be

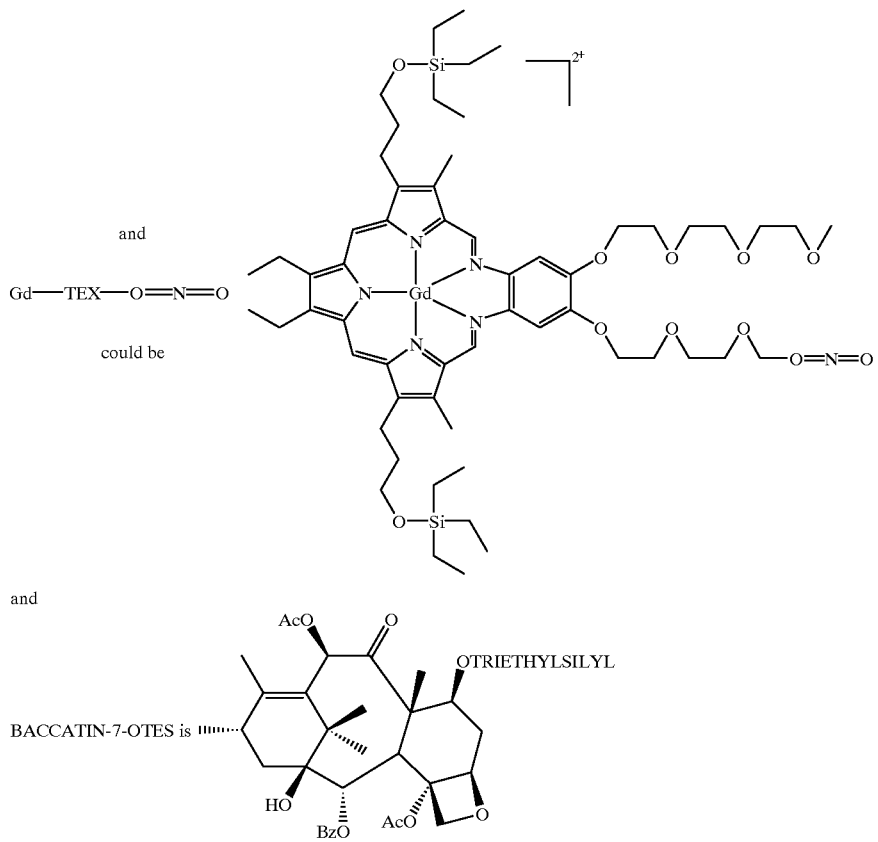

and

BACCATIN-7-OTES is

Scheme M relies on the use of a bis-triethylsilyl (TES) protected aminotexaphyrin. This texaphyrin could be transformed into the corresponding isocyanate by reaction with triphosgene in the presence of pyridine. The TES group, together with the Troc (2,2,2-trichloroethylcarbonyl) group, are widely used for 2'-OH and 7-OH protection in taxol chemistry [Nicolaou K. C., Dai W.-M., Guy R. K.: Angew. Chem. Int. Ed. Engl. 33, 15 (1994)]. The TES protecting group is usually removed using a water-THF-acetic acid mixture, conditions towards which a imetallotexaphyrin complex should be stable.

2'-Carbamate Conjugate (Scheme N)

The same putative protected texaphyrin isocyanate is coupled with a 7-TES-protected taxol to give a 2'-carbamate conjugate (as shown in generic terms in Scheme N).

Scheme N

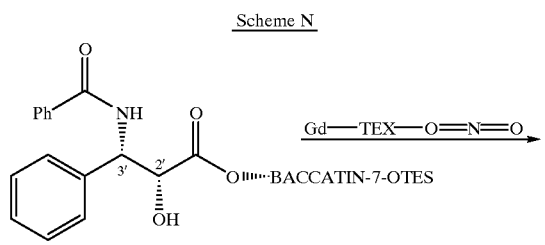

Gd—TEX—O=N=O →

-continued

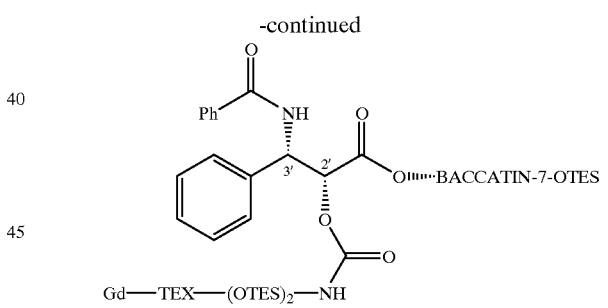

Gd—TEX—(OTES)$_2$—NH

Temporary/transient texaphyrin-taxol conjugates can be generated via ester Or carbonate linkages established through either 2'-OH or 7-OH substitution on the taxol skeleton. While a lesser reduction in biological activity might be expected as the result of 7-OH substitution, synthetic considerations lead to the 2'-OH modification being preferred. Further, in the case of certain taxol 2'-esters and 2'-carbonates, biological activity is retained. While not wishing to be bound by any particular theory, this is presently believed to be the result of slow, controlled release of the taxol drug arising as a consequence of in vivo 2'-ester or carbonate hydrolysis [Nicolaou K. C., Dai W.-M., Guy R. K.: Angew. Chem. Int. Ed. Engl. 33,15 (1994)].

Ester-linked Texaphyrin-Taxol Coniugate (Scheme O)

An activated texaphyrin carboxylic acid would be subject to either direct activation (DCC, HOBT, etc.) or pre-conversion to an active ester in order to set up the critical conjugation step.

Scheme O
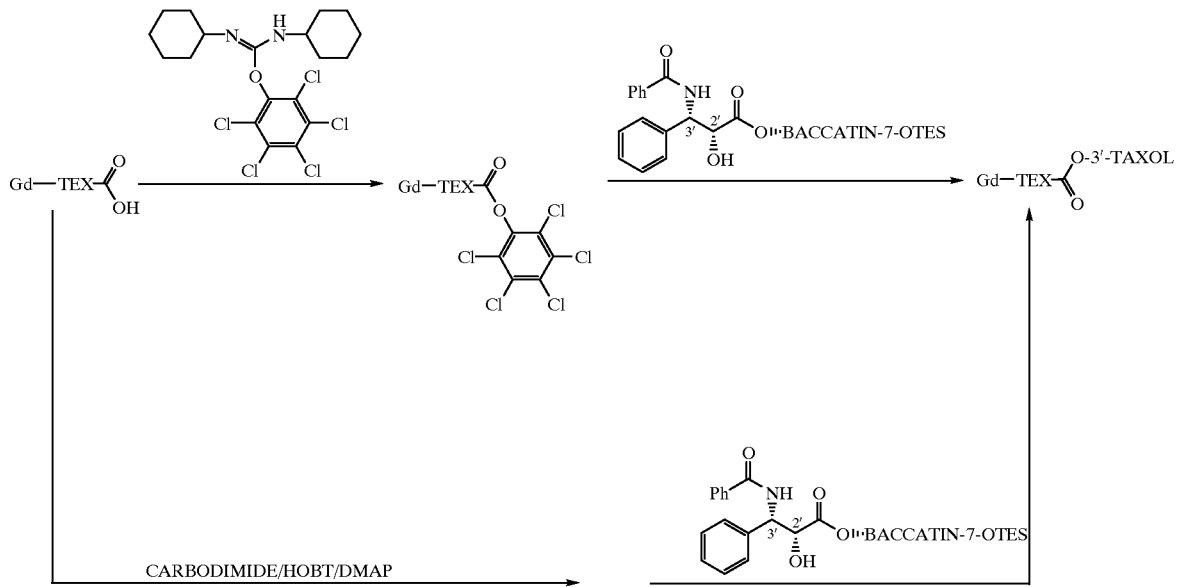
The Carbonate Approach (Scheme P)
This requires the preparation of a protected texaphyrin-chloroformate. In the case of texaphyrins with —OH groups, such a species can be obtained via TES propyl-OH protection followed by reaction with phosgene.
Scheme P
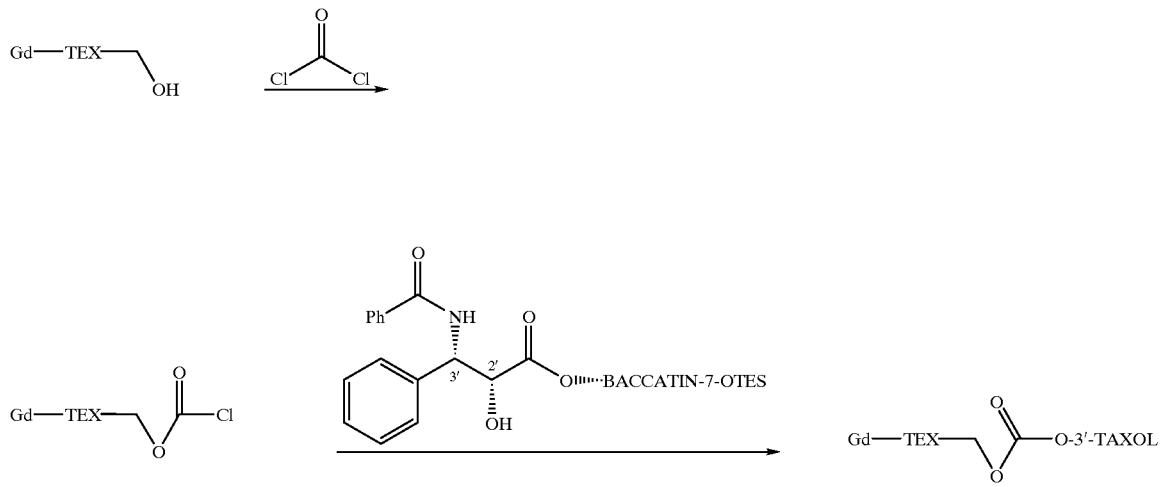

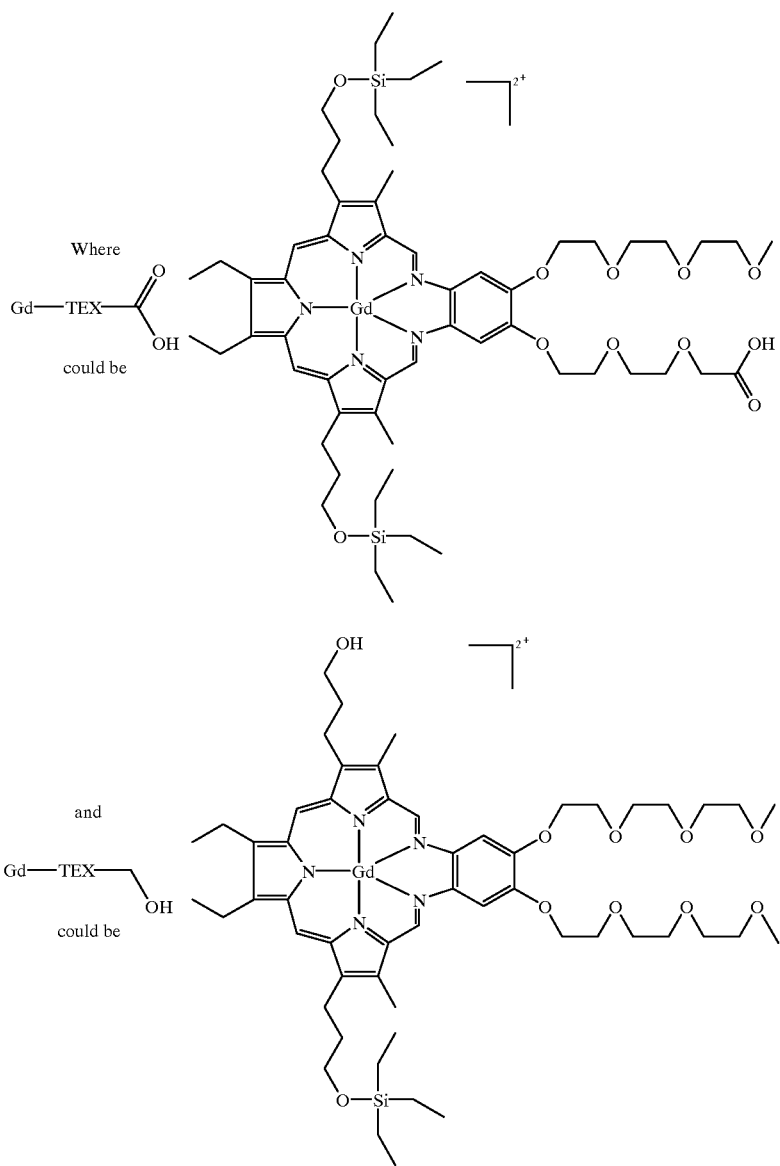

Pro-drugs (Schemes Q and R)

Taxol (or other) prodrugs can undergo controlled taxol (drug) release in vivo [Nicolaou K. C. et al.: Angew. Chem. Int.Ed. Engl. 33, 1583 (1994)]. This methodology, summarized in Scheme Q, is based on the reaction of a taxol hydroxy derivative with N-methyl-2-fluoropyridine. This yields an N-methyl-2-(2'-taxoleoxy)pyridine species that is both soluble in, and hydrolyzed by, water.

Scheme Q

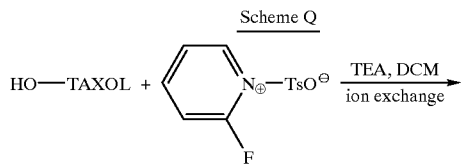

-continued

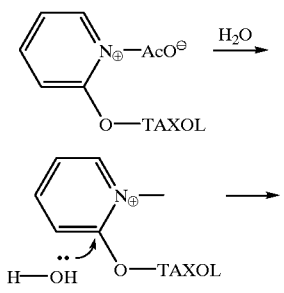

-continued

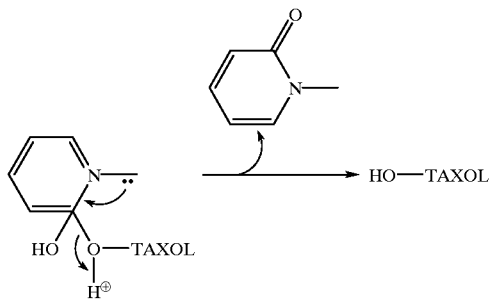

A modification of this approach, more suitable for use with texaphyrins, is shown in Scheme R.

A di-acid gadolinium conjugate such as 20 is contacted with a solution of (1,2-diaminopropane)Pt(II)(NO$_3$)$_2$ to yield the corresponding diamine platinum complex of Formula 22

A metallated texaphyrin complex such as Formula 39 is contacted with aqueous methylamine to give the corresponding complex of Formula 40 (having a Pt metal chelating site according to Formula III).

A metallated texaphyrin complex conjugated with a Pt metal chelating site such as Formula 40 is contacted with K$_2$PtCl$_4$ to provide the corresponding texaphyrin-cisplatinum complex of Formula 41.

A hydroxy-substituted, metallated texaphyrin (such as PCI-0120) and an optionally-substituted nucleotide phosphoramidite are contacted under suitable conditions to yield the corresponding bis-nucleotide texaphyrin conjugate.

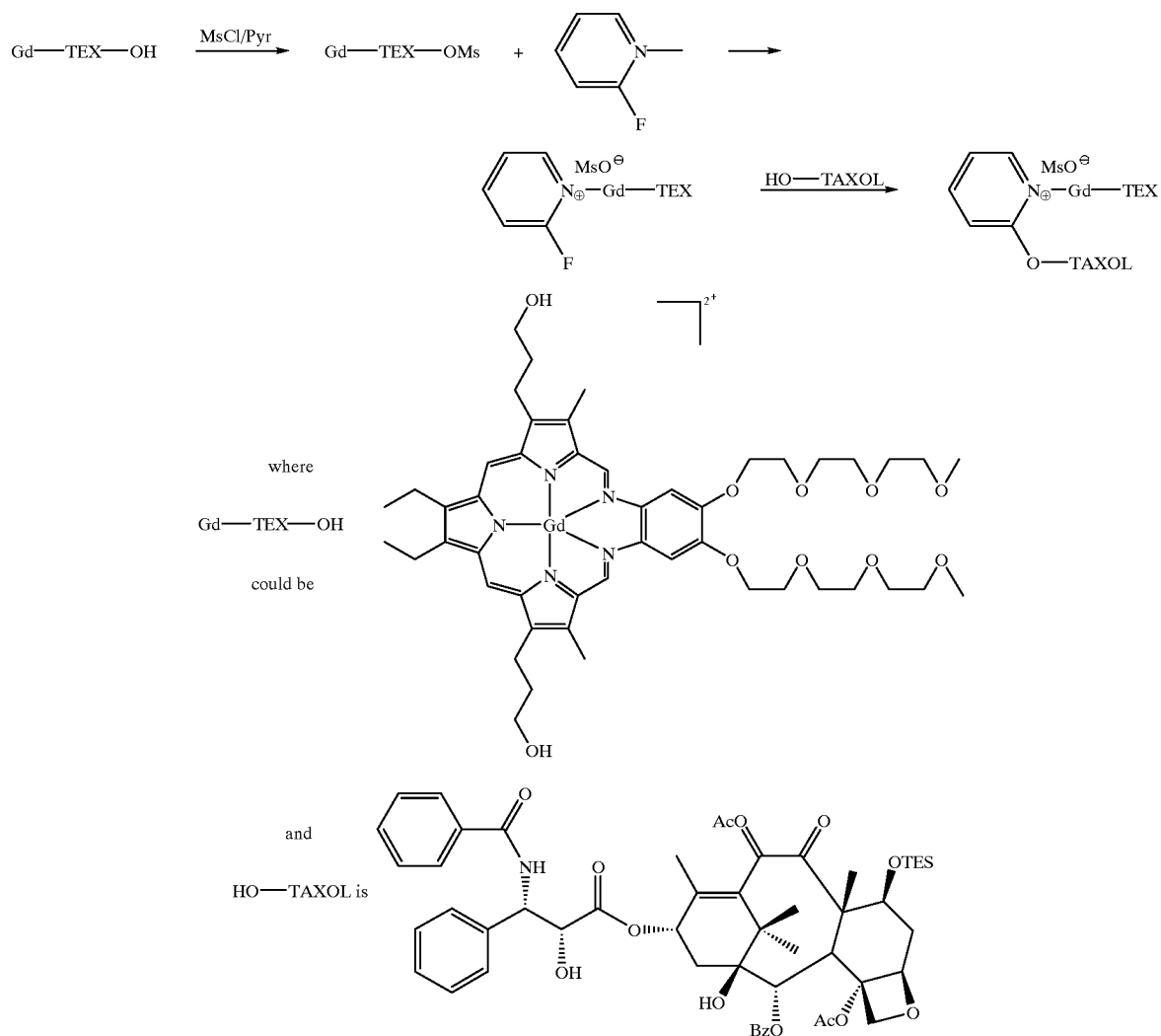

Preferred Process and Last Steps

A di-acid gadolinium conjugate such as 20 is platinated by contact with Pt(NH$_3$)$_2$Cl$_2$ to yield the corresponding cisplatin conjugate complex of Formula 21.

A compound of Formulae A or B is contacted with a pharmaceutically acceptable acid to form the corresponding acid addition salt or apical ligand.

A pharmaceutically acceptable acid addition salt or apical ligand of Formulae A or B is contacted with a base to form the corresponding free base.

Preferred Compounds

The compounds of Formula A are preferred.

Also preferred are the compounds of Formula A where $R_1$, $R_7$ and/or $R_8$ is a chemotherapeutic agent, a couple to a chemotherapeutic agent, a platinum(II) metal chelating site, a couple to a platinum(II) metal chelating site, a platinum (IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV).

Of the compounds of Formula A having a platinum metal chelating site, preferred are the compounds where the chelating site is Formula I, III or IV, particularly Formula III or Formula IV where $Q_1$ and $Q_2$ are carboxylic acid anions, and especially preferred are those compounds where the preferred chelating site is complexed with platinum(II) or platinium(IV).

Further preferred are the compounds of Formula A where $R_7$ and/or $R_8$ are an alkoxypolyether. Still further preferred are those compounds where $R_1$ is a lower alkanol and $R_2$ to $R_4$ are lower alkyl. Especially preferred are those compounds where $R_1$ is —$CH_2$—$CH_2$—$CH_2$—OH, each of $R_2$ and $R_3$ is —$CH_2$—$CH_3$, $R_4$ is —$CH_3$, and each of $R_5$, $R_6$ and $R_9$–$R_{12}$ is hydrogen.

Preferably, the chemotherapeutic agent employed in the conjugates of the invention is selected from a taxoid, a nucleotide, an antibiotic, or a platinum coordination complex, most preferably from bleomycin, doxorubicin, taxol, taxotere, etoposide, 4-OH cyclophosphamide, 5-fluorouracil, cisplatin, or platinum coordination complexes analogous to cisplatin.

Utility, Testing and Administration

General Utility

The texaphyrin-chemotherapeutic conjugates of the present invention, formulations and methods are useful for treating atheroma, tumors and other neoplastic tissue, neovascular-related diseases, as well as other conditions that are typically responsive to chemotherapy, radiation sensitization and photodynamic therapy.

Testing

In vitro activity for texaphyrin-chemotherapeutic conjugates of the present invention is determined by, e.g., tumor cell proliferation assays, as will be well known to those skilled in the art.

In vivo activity for texaphyrin-chemotherapeutic conjugates of the present invention is determined by, e.g., tumor implant models, as will be well known to those skilled in the art.

The texaphyrin-chemotherapeutic conjugates of the present invention are tested for safety and efficacy employing pharmaceutical industry- and regulatory agency-accepted toxicologic, stability and human clinical trial protocols.

Administration

The compounds of the invention are administered at a therapeutically effective dosage, e.g., a dosage sufficient to provide treatment for the disease states previously described, optionally with a co-therapeutic agent as is known in the art. The co-therapeutic agent to be used can consist of photodynamic therapy, radiation sensitization, chemotherapy, or sonodynamic therapy. The compounds disclosed herein can be used both diagnostically (e.g. imaging or fluorescence) and therapeutically. One of skill in the art in light of the present disclosure would also realize flexibility in the below regimens and would be able to test, without undue experimentation, for optimal timing and dosage for administration of a texaphyrin for a particular circumstance.

Dosages: The specific dose will vary depending on the particular texaphyrin-chemotherapeutic conjugate chosen, the dosing regimen to be followed, and the particular co-therapeutic agent with which it is administered, employing dosages within the range of about 0.01 mg/kg/treatment up to about 50 mg/kg/treatment (depending on the molecular weight of the conjugate). Dosage is also determined by the normal dosages for the chemotherapeutic agent, adapted for the selective localization provided by the texaphyrin. It will be appreciated by one skilled in the art, however, that there are specific differences in the most effective dosimetry depending on the apical ligands chosen.

Administration in conjunction with Photodynamic Therapy: By way of example, lutetium texaphyrin is administered in solution containing 2 mg/ml optionally in 5% mannitol, USP. Dosages of about 1.0 or 2.0 mg/kg to about 4.0 or 5.0 mg/kg, preferably 3.0 mg/kg may be employed, up to a maximum tolerated dose that was determined in one study to be 5.2 mg/kg. The texaphyrin is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

The co-administration of a sedative (e.g., benzodiazapenes) and narcotic analgesic are sometimes recommended prior to light treatment along with topical administration of Emla cream (lidocaine, 2.5% and prilocaine, 2.5%) under an occlusive dressing. Other intradermal, subcutaneous and topical anesthetics may also be employed as necessary to reduce discomfort. Subsequent treatments can be provided after approximately 21 days. The treating physician may choose to be particularly cautious in certain circumstances and advise that certain patients avoid bright light for about one week following treatment.

When employing photodynamic therapy, a target area is treated with light at about 732±16.5 nm (full width half max) delivered by LED device or an equivalent light source (e.g., a Quantum Device Qbeam™ Q BMEDXM-728 Solid State Lighting System, which operates at 728 nm) at an intensity of 75 mW/cm$^2$ for a total light dose of 150 J/cm$^2$. The light treatment takes approximately 33 minutes.

The optimum length of time following texaphyrin administration until light treatment can vary depending on the mode of administration, the form of administration, and the type of target tissue. Typically, the texaphyrin persists for a period of minutes to hours, depending on the texaphyrin, the formulation, the dose, the infusion rate, as well as the type of tissue and tissue size.

After the photosensitizing texaphyrin has been administered, the tissue being treated is photoirradiated at a wavelength similar to the absorbance of the texaphyrin, usually either about 400–500 nm or about 700–800 nm, more preferably about 450–500 nm or about 710–760 nm, or most preferably about 450–500 nm or about 725–740 nm. The light source may be a laser, a light-emitting diode, or filtered light from, for example, a xenon lamp; and the light may be administered topically, endoscopically, or interstitially (via, e.g., a fiber optic probe). Preferably, the light is administered using a slit-lamp delivery system. The fluence and irradiance during the photoirradiating treatment can vary depending on type of tissue, depth of target tissue, and the amount of overlying fluid or blood. For example, a total light energy of about 100 $J/cm^2$ can be delivered at a power of 200 mW to 250 mW depending upon the target tissue.

Administration for Chemosensitization: The texaphyrin-chemotherapeutic conjugate may be administered as a single dose, or it may be administered as two or more doses separated by an interval of time. The dosing protocol may be repeated, from one to three times, for example. Administration may be intra-arterial injection, intravenous, intraperitoneal, parenteral, intramuscular, subcutaneous, oral, topical, or via a device such as a stent, for example, with parenteral and intra-arterial administration being preferred, and intra-arterial being more preferred.

Administering a texaphyrin-chemotherapeutic conjugate to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of texaphyrin and chemotherapeutic drug will be within 6–12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

Administration in conjunction with Radiation Sensitization: Gadolinium texaphyrin is administered in a solution containing 2 mM optionally in 5% mannitol USP/water (sterile and non-pyrogenic solution). Dosages of 0.1 mg/kg up to as high as about 23.0 mg/kg have been delivered, preferably about 3.0 to about 15.0 mg/kg (for volume of about 90 to 450 mL) may be employed, optionally with pre-medication using anti-emetics above about 6.0 mg/kg. The texaphyrin-chemotherapuetic conjugate is administered via intravenous injection over about a 5 to 15 minute period, followed by a waiting period of about 2 to 5 hours to facilitate intracellular uptake and clearance from the plasma and extracellular matrix prior to the administration of radiation.

When employing radiation therapy, a palliative course of 30 Gy in ten (10) fractions of radiation are administered over consecutive days excluding weekends and holidays. In the treatment of brain metastases, whole brain megavolt radiation therapy is delivered with $^{60}$Co therapy or a $\geq 4$ MV linear accelerator with isocenter distances of at least 80 cm, using isocentric techniques, opposed lateral fields and exclusion of the eyes. A minimum dose rate at the midplane in the brain on the central axis is about 0.5 Gy/minute.

Texaphyrins used as radiation sensitizers may be administered before, or at the same time as, or after administration of the ionizing radiation. The texaphyrin may be administered as a single dose, as an infusion, or it may be administered as two or more doses separated by an interval of time. Where the texaphyrin is administered as two or more doses, the time interval between the texaphyrin administrations may be from about one minute to a number of days, preferably from about 5 min to about 1 day, more preferably about 4 to 5 hr. The dosing protocol may be repeated, from one to ten or more times, for example. Dose levels for radiation sensitization may range from about 0.05 $\mu$mol/kg to about 20 $\mu$mol/kg administered in single or multiple doses (e.g. before each fraction of radiation). The lower dosage range would be preferred for intra-arterial injection or for impregnated stents.

Administration may be intra-arterial injection, intravenous, intraperitoneal, parenteral, intramuscular, subcutaneous, oral, topical, or via an impregnated or coated device such as a stent, for example, or an artery-inserted cylindrical polymer, with parenteral and intra-arterial administration being preferred, and intra-arterial being more preferred. In one aspect of the invention, a patient having restenosis or at risk for restenosis is administered a dose of texaphyrin at intervals with each dose of radiation.

Administering a texaphyrin to the subject may be prior to, concurrent with, or following vascular intervention, and the intervention is followed by radiation. The method may begin prior to, such as about 24–48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of texaphyrin and radiation will be within 1–24 hours of the vascular intervention, preferably within about 5–24 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Sonodynamic Therapy: The use of texaphyrins in sonodynamic therapy is described in U.S. patent application Ser. No. 60/088,214 previously incorporated herein by reference. A texaphyrin-chemotherapeutic conjugate is administered before administration of the sonodynamic agent. The conjugate may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of the invention. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave.

Preferred sonodynamic agents employed in the present invention is ultrasound, particularly is low intensity, non-thermal ultrasound, i.e., ultrasound generated within the wavelengths of about 0.1 MHz and 5.0 MHz and at intensities between about 3.0 and 5.0 $W/cm^2$.

Further Administration Protocols: Texaphyrin-chemotherapeutic conjugate, optionally including a suitable co-therapeutic agent can also be administered in the context of other medical procedures. For example, in allograft transplantation, administration may be accomplished by perfusion of the graft prior to implantation. Following a brief period for uptake, e.g., by macrophages, the remaining texaphyrin is rinsed from the graft followed by application of the co-therapeutic agent. Administration to selectively treat diseases characterized by circulating macrophages may be accomplished by extracorporeal contact, filtration of non-absorbed texaphyrin employing a lipophilic filter, followed by application of the co-therapeutic agent.

Formulations

In employing the compounds of this invention for treatment of the above conditions, any pharmaceutically acceptable mode of administration can be used. Certain compounds of Formula A or B can be administered alone, but are preferably formulated in combination with pharmaceutically acceptable excipients, including solid, semi-solid, liquid or aerosol dosage forms, such as, for example, tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula A or a pharmaceutically acceptable salt, ester or apical ligand thereof. In addition, these formulations may include other medicinal agents, pharmaceutical agents, carriers, adjuvants, etc.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, manitol, DMF, DMSO and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. DMF and/or DMSO are preferred ingredients in the platinum complex formulations of the invention. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, manitol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. Preferably the composition will comprise 0.2–2% of the active agent in solution.

EXAMPLES

The following preparations and examples are given to enable those skilled in the art to more clearly understand and to practice the present invention. They should not be considered as limiting the scope of the invention, but merely as being illustrative and representative thereof.

Example 1

The synthesis of a texaphyrin-cisplatin conjugate (9), utilizing a platinum(II) metal chelating site and follows Reaction Scheme A.

1-[2-[2-(2-Methoxyethoxy)-ethoxy]-ethyl]-4-tert-butyloxycarbonyl-piperazine, 2.

Potassium carbonate (1.382 g, 10 mmol), 2-[2-(2-chloroethoxy)ethoxy]-ethanol (0.843 g, 5.0 mmol), and N-tert-butyloxycarbonyl-piperazine 1 (0.90† g, 4.83 mmol) (Krapcho, A. P., Kuell, C. S. *Synth. Commun.* 1990, 20, 2559) were suspended in acetonitrile (30 mL), and the resulting mixture was heated at reflux for 12 hours under an argon atmosphere. The reaction mixture was allowed to cool to ambient temperature and was filtered over Celite™. Removal of solvents under reduced pressure yielded crude product as an oil (2.05 g). Flash column chromatography on silica using 10% of methanol in dichloromethane yielded purified 2 (1.24 g, 77%). $^1$H NMR (CD$_2$Cl$_2$): δ 1.41 (s, 9H, CH$_3$); 2.40 (t, 8H, J=5.2 Hz, CH$_2$N); 2.53 (t, 4H, J=5.6 Hz, piperazine CH$_2$N); 3.30 (s, 3H, OCH$_3$); 3.42 (m, 4H, OCH$_2$); 3.2 (m, 4H, OCH$_2$); 3.68 (m, 4H, OCH$_2$). $^{13}$C NMR (CD$_2$Cl$_2$): δ 28.8, 49.5, 53.7, 58.1, 59.4, 69.1, 70.7, 70.9, 71.0, 72.3, 80.5, 157.0. Cl MS, (M)$^+$: m/e 332.

1-[2-[2-[2-(4-Toluene-4-sulfonyl)ethoxy]ethoxy]ethoxy]-2-[2-[2-(2-metethoxy)-ethoxy]ethoxy]-4,5-dinitrobenzene, 4.

1-[2-[2-(2-Methoxyethoxy)ethoxy]ethoxy]-2-[2-[2-(2-hydroxyethoxy)ethoxy]-ethoxy]-4,5-dinitrobenzene 3 (0.960 g, 2.0 mmol) and 4-toluenesulfonyl chloride (0.275 g, 2.1 mmol) were dissolved in pyridine at 0° C. The resultant solution was stirred for 18 hours, whereupon solvent was evaporated at reduced pressure. The residue was partitioned between chloroform (50 mL) and cold 10% aqueous citric acid (100 mL). After separation, the organic layer was washed with citric acid solution (2×70 mL), water (50 mL) and aqueous sodium hydrogen carbonate solution (50 mL), and dried over anhydrous sodium sulfate. Removal of solvent under reduced pressure produced a yellow oil (1.264 g). Flash column chromatography on silica using 3% methanol in dichloromethane yielded purified 4 (1.038 g, 82%). $^1$H NMR (CD$_2$Cl$_2$): δ 2.52 (s, 3H, tolyl); 3.42 (s, 3H, OCH$_3$); 3.52 (m, 2H, OCH$_2$); 3.63 (m, 12H, OCH$_2$); 3.87 (m, 4H, OCH$_2$); 4.14 (m, 2H, OCH$_2$); 4.28 (m, 4H, OCH$_2$); 7.32 (m, 2H, tolyl); 3.45 (s, 1H, dinitrophenyl); 3.47 (s, 1H, dinitrophenyl); 7.8 (m, 2H, tolyl). $^{13}$C NMR (CD$_2$Cl$_2$): δ 21.6, 59.1, 68.7, 69.2, 69.5, 69.9, 70.5, 70.7, 70.8, 70.9, 71.0, 71.5, 71.9, 109.3, 109.4, 127.9, 129.8, 132.9, 134.2, 136.6. 144.8, 151.6, 152.2. Cl MS (M)$^+$: m/e 633.

1-[2-[2-[2-[2-[2-(2-Methoxyethoxy)ethoxy]ethyl]-[1,4-diazacyclohex-1,4-yl]ethoxy]-ethoxy]ethoxy]-2-[2-[2-(2-methoxyethoxy)ethoxy]ethoxy]-4,5-dinitrobenzene, 5.

1-[2-[2-(2-Methoxyethoxy)-ethoxy]-ethyl]-4-tert-butyloxycarbonyl-piperazine 2 (0.665 g, 2.00 mmol) was dissolved in dichloromethane (7 mL) and trifluoroacetic acid (3 mL). The resulting solution was stirred at room temperature for 6 hours, whereupon solvents were evaporated under reduced pressure and the residue dried in vacuo (1.0 Torr) for 1.5 hours. The presumed 1-[2-[2-(2-methoxyethoxy)ethoxy]-ethyl]piperazine bis-trifluoroacetate intermediate was dissolved in acetonitrile (30 mL) and potassium carbonate (1.00 g, 7.24 mmol) was added. The resulting suspension was stirred under an inert atmosphere until the evolution of gas ceased, whereupon a solution of 1-[2-[2-[2-(4toluene-4-sulfonyl)ethoxy]ethoxy]ethoxy]-2-[2-[2-(2-methoxyethoxy)ethoxy]ethoxy]-4,5-dinitro-benzene 4 (1.000 g, 1.58 mmol) in acetonitrile (30 ml) was added dropwise over 0.5 hr. The reaction mixture was gently heated for 14 hours, then allowed to cool to ambient temperature, and filtered over Celite™. Solvent was removed under reduced pressure, yielding crude product as an oil (1.52 g). Flash column chromatography on silica using 6% methanol in dichloromethane yielded purified 5 (0.214 g, 20%). $^1$H NMR (CD$_2$Cl$_2$): δ 2.21 (t, 8H, J=5.4 Hz, piperazine CH$_2$N); 3.33 (s, 3H, OCH$_3$); 3.38 (s, 3H, OCH$_3$); 3.56 (m, 4H, CH$_2$); 3.62 (m, 20H, OCH$_2$); 3.71 (m, 4H, OCH$_2$); 3.82 (m, 4H, OCH$_2$); 4.65 (m, 4H, OCH$_2$); 7.48 (s, H, dinitrophenyl); 7.50 (s, 1H, dinitrophenyl). $^{13}$C NMR (CD$_2$Cl$_2$): δ 54.9, 58.3, 58.6, 59.7, 69.6–72.6 (18×C), 110.4, 137.4, 152.9. Cl MS (M)$^+$: 693.

Hydrochloride salt of 4,5-diethyl-10,23-dimethyl-9,24-bis(3-hydroxypropyl)-16-[2-[2-[2-[2-[2-(2-methoxyethoxy)ethoxy]ethyl]-[1,4-diazacyclohex-1,4-yl]ethoxy]ethoxy)ethoxy]-17-[2-[2-(2-methoxyethoxy)ethoxy]ethoxy]-13,20,25,26,27-pentaazapentacyclo[20.2.1.1$^{3,6}$.1$^{8,11}$.0$^{14,19}$]-heptacosa-3,5,8,10,12,14,16,18,20,22,24-undecaene, 7.

In a 250 mL Parr flask 1-[2-[2-[2-[2-[2-(2-methoxyethoxy)ethoxy]ethyl]-[1,4-diaza-cyclohex-1,4-yl]ethoxy]ethoxy]ethoxy]-2-(2-[2-(2-methoxyethoxy)ethoxy]-ethoxy)-4,5-dinitro-benzene 5 (147 mg, 0.212 mmol) was dissolved in methanol (15 mL). Under a strict nitrogen atmosphere 10% palladium on carbon (40 mg) was added followed by concentrated hydrochloric acid (35 :L). The flask was placed on a Parr hydrogenation apparatus at a maintained hydrogen pressure of 40 psi. After 2.5 h an additional amount of palladium on carbon (20 mg), and concentrated hydrochloric acid (40 :L) was added to drive the reaction to completion. After a further 1.5 h, when consumption of hydrogen had ceased, the catalyst was removed by filtration over a pad of Celite™ filter agent, and the solution of presumed 1-[2-[2-[2-[2-[2-(2-methoxyethoxy)ethoxy]ethyl]-[1,4-diazacyclohex-1,4-yl]ethoxy]ethoxy)-ethoxy]-2-(2-[2-(2-methoxyethoxy)ethoxy]ethoxy)-4,5-diamino-benzene was transferred to a 50 mL single-neck flask containing a stir-bar and 2,5-bis[[(5-formyl-3-(3-hydroxypropyl)-4-methylpyrrol-2-yl)methyl]-3,4-diethylpyrrole 6 (97 mg, 0.201 mmol). The reaction was diluted by the addition of methanol to a total volume of 30 mL and then stirred at ambient temperature under a nitrogen atmosphere. After 18 h the solvent was removed by rotary evaporation under reduced pressure and the residue was dried under high vacuum for 15 h to afford the title compound as a crimson-red glassy solid (201 mg, 87%). $^1$H NMR (CD$_3$OD): δ 1.13 (t, 6H, CH$_2$CH$_3$), 1.76 (p, 4H, pyrr-CH$_2$CH$_2$CH$_2$OH), 2.37 (s, 6H, pyrr-CH$_3$), 2.48 (q, 4H, CH$_2$CH$_3$), 2.65 (t, 4H, pyrr-CH$_2$CH$_2$CH$_2$OH), 3.30 (s, 6H, [CH$_2$CH$_2$O]$_3$CH$_3$), 3.33 (t, 4H, pyrr-CH$_2$CH$_2$CH$_2$OH), 3.38–4.00 (m, 40H, CH$_2$CH$_2$OCH$_2$CH$_2$OCH$_2$CH$_2$-piperazine-CH$_2$CH$_2$OCH$_2$CH$_2$OCH$_2$CH$_2$O, CH$_2$CH$_2$OCH$_2$CH$_2$OCH$_2$CH$_2$O), 4.11 (s, 4H, [pyrr]$_2$—CH$_2$), 4.33 (t, 4H, PhOCH$_2$CH$_2$O, 7.53 (d, 2H, PhH), 8.34 (d, 2H, HC=N); $^{13}$C NMR (DMSO-d$_6$): δ 9.91, 10.04, 17.02, 18.63, 20.92, 33.49, 59.06, 59.09, 61.99, 65.56, 65.81, 70.74, 70.85, 70.95, 71.09, 71.21, 71.34, 71.48, 71.61, 71.77, 72.94, 73.00, 108.78, 108.96, 120.78, 123.89, 125.21, 126.49, 129.01, 145.01, 150.87; FAB MS, (M+H)$^+$: m/e 1079; HR MS, (M+H)$^+$: m/e 1078.6790 (calc.d for C$_{58}$H$_{92}$N$_7$O$_{12}$, 1078.6804).

Gadolinium(III) complex of 4,5-diethyl-10,23-dimethyl-9,24-bis(3-hydroxypropyl)-16-[2-[2-[2-[2-[2-(2-methoxyethoxy)ethoxy]ethyl]-[1,4-diazacyclohex-1,4-yl]ethoxy]ethoxy]ethoxy]-17-[2-[2-(2-methoxyethoxy)ethoxy]ethoxy]-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene, 8.

In a 100 mL single-neck flask, fitted with a short condenser, the hydrochloride salt of 4,5-diethyl-10,23-dimethyl-9,24-bis(3-hydroxypropyl)-16-[2-[2-[2-[2-[2-(2-methoxyethoxy)ethoxy]ethyl]-[1,4-diazacyclohex-1,4-yl]ethoxy]ethoxy)ethoxy]-17-[2-[2-(2-methoxyethoxy)ethoxy]ethoxy]-13,20,25,26,27-pentaazapentacyclo-[20.2.1.1$^{3,6}$.1$^{8,11}$.0$^{14,19}$]heptacosa-3,5,8,10,12,14,16,18,20,22,24-undecaene 7 (175 mg, 0.152 mmol), gadolinium acetate hydrate (93 mg, 0.2281 mmol), triethylamine (212 :L, 1.520 mmol) and methanol (38 mL) were combined and heated under reflux open to the atmosphere. After 6 h air was dispersed through the reaction for 30 minutes. After a further 2 h the reaction was cooled to ambient temperature, filtered over a pad of Celite™ filter agent, and solvents were removed by rotary evaporation under reduced pressure. After drying for 2 h under high vacuum the residue was suspended in acetone (10 mL) and stirred for 10 minutes at room temperature. Insoluble material was filtered, washed with acetone (10 mL), and dried under high vacuum. After 15 h the residue was dissolved in methanol (22.5 mL) and deionized water (2.5 mL) and acetic acid washed SAY-54 zeolite (1.2 g) was added. The flask was gently agitated for 2.5 h at which point the zeolite was removed by filtration. The treatment with zeolite was repeated and the resulting solution was treated with n-butanol (5 mL) to prevent bumping during rotary evaporation. Solvents were removed by rotary evaporation under reduced pressure and the residue was further dried under high vacuum. After 15 h the residue was suspended in acetone (10 mL) and stirred for 10 minutes at ambient temperature. Insoluble material was filtered, washed with acetone (10 mL), and dried under high vacuum to afford the title compound as a dark green solid (80 mg, 27%). UV/vis [$δ_{max}$, nm (CH$_3$OH)]: 412.0, 472.0, 738.0; FAB MS, M$^+$: m/e 1231; HR MS, M$^+$: m/e 1228.5556 (calcd for C$_{58}$H$_{86}$N$_7$O$_{12}$$^{156}$Gd, 1228.5502).

cis-Dichloroplatinum(II) complex of gadolinium(III) complex of 4,5-diethyl-10,23-aimethyl-9,24-bis(3-hydroxypropyl)-16-[2-[2-[2-[2-[2-(2-methoxyethoxy)ethoxy]ethoxy]-[1,4-diazacyclohex-1,4-yl]ethoxy]ethoxy]ethoxy]-17-[2-[2-(2-methoxyethoxy)ethoxy]-ethoxy]-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene, 9.

Potassium tetrachloroplatinate(II) (4.2 mg, 0.01 mmol) was dissolved in water (1.0 mL) in a septum-sealed microvial, heated under argon atmosphere to 45° C., and gadolinium(III) complex of 4,5-diethyl-10,23-dimethyl-9,24-bis(3-hydroxypropyl)-16-[2-[2-[2-[2-(2-methoxyethoxy)ethoxy]ethyl]-[1,4-diazacyclohex-1,4-yl]ethoxy]ethoxy]ethoxy]-17-[2-[2-(2-methoxyethoxy)ethoxy]-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene 8 (7.3 mg, 0.005 mmol) in water (0.5 ml) was added. The reaction mixture was stirred until a dark precipitate formed (ca. 20 minutes). The suspension was filtered using a 0.2 micron nylon filter and the green filtrate evaporated to afford 9 (2.0 mg). The filter cake was washed with water (5×10 mL) and with cold N,N-dimethylformamide (2.0 mL). Solvent was removed from the combined filtrates under reduced pressure and the residue dried in vacuo to provide additional compound 9 (3.5 mg, 70% combined yield). The remaining filter cake comprised mainly platinum black and only traces of product. FAB MS (glycerol), (M)$^+$: m/e 1530.

Example 2

The synthesis of a texaphyrin-cisplatin conjugate (16) follows Reaction Scheme B.

N$_3$-Benzyloxycarbonyl-N$_1$,N$_2$-bis-(9H-fluorene-9-ylmethoxycarbonyl)-but-1-ene-1,2,4-triamine, 11.

Benzyloxycarbonyl-[2-(1H-imidazol-4-yl)ethyl]amine 10, prepared according to Altman et al. (Z. Naturforsch. B. 46:1473–1488 (1991)), is dissolved in dioxane (50 mL) and a saturated solution of sodium carbonate (50 mL) is added. The resulting mixture is heated to 80° C. with vigorous stirring for 24 hours, then diluted by mixture of dioxane and water (1:1, 100 mL) and cooled to 0° C. 9H-fluorene-9-yl-methyl chloroformate ("Fmoc-Cl") (6.209 g, 24 mmol) in tetrahydrofuran 50 mL) is added dropwise during a 30 min period. The mixture is stirred at 0° C. for 18 h, after which chloroform (300 mL) and brine (100 mL) are added and the resulting mixture is well shaken. The organic phase is separated, washed with 10% aqueous solution of citric acid (200 mL) and then with aqueous sodium bicarbonate (200 mL) and brine (200 mL), dried over anhydrous sodium sulfate and evaporated to dryness. Flash column on silica gives the product.

N$_1$,N$_2$-Bis-(9H-fluoren-9-ylmethoxycarbonyl)butane-1,2,4-triamine, 12.

Compound 11 (3.400 g, 5.0 mmol) and 10% Pd on carbon (0.1 g) are suspended in methanol-tetrahydrofuran (1:1, 100 mL) and aqueous 1M hydrochloric acid (5.5 mL). The mixture is heated in an autoclave, cooled by water-ice bath, and then hydrogenated at pressure of 40 psi until the reaction is over (followed by thin layer chromatography: silica/20% acetone in hexanes), circa 6 hours. Catalyst is filtered off, washed with mixture methanol-tetrahydrofuran, combined filtrates are evaporated to 25% of original volume and let crystallize in refrigerator. Product is filtered off as an hydrochloride. Free amine is obtained upon dissolution in chloroform, washing with aqueous sodium hydrogen carbonate, drying of organic phase over sodium sulfate and evaporation to dryness.

2-[2-[2-(2-methoxyethoxy)ethoxy)ethoxy]-4,5-dinitrophenol, sodium salt.

In a dry 250 mL RBF, 4,5-dinitrocatechol (10 g, 0.050 mol) and K$_2$CO$_3$ (10.37 g, 0.075 mol) were combined in absolute methanol (120 mL) under nitrogen atmosphere. To the orange mixture, triethylene glycol monomethyl ether tosylate (23.85 g, 0.075 mol) was added and the resulting suspension was heated to reflux. The reaction was deemed complete by TLC analysis by the disappearance of the starting catechol and appearance of the bright yellow monoalkylated intermediate. Therefore, after 16 h the red suspension was cooled to 0° C. The resulting suspension was filtered, washed thoroughly with cold isopropyl alcohol (50 mL) and hexanes (50 mL). The monoalkylated potassium salt was then suspended in 10% aqueous NaOH (100 mL), vigorously stirred for 15–20 min at rt, filtered, and then rinsed thoroughly with cold isopropyl alcohol (70 mL) and hexanes (50 mL). (This step aids in the removal of excess K$_2$CO$_3$ and potassium tosylate). The bright orange salt was dried in vacuo and afforded 15 g (~81%). $^1$H NMR (MeOD): δ 3.24 (m, 2H, CH$_2$CH$_2$O); 3.30 (s, 3H, OCH$_3$); 3.47 (m, 2H, CH$_2$CH$_2$O); 3.55 (m, 4H, CH$_2$CH$_2$O); 3.80 (m, 2H, CH$_2$CH$_2$O); 4.08 (m, 2H, CH$_2$CH$_2$O); 6.40 (s, 1H, ArH), 7.43 (s, 1H, ArH). $^{13}$C NMR (MeOD): •59.1, 69.1, 70.4, 71.0, 71.1, 71.3, 72.7, 109.2, 113.2, 124, 147, 152, 172. EI MS (M+Na$^+$) 369; EI HRMS (M+Na$^+$) 369.0910 (calcd. for C$_{13}$H$_{18}$N$_2$O$_9$Na 369.0910).

1-[1-(Ethyloxy)acetyl-2-oxy]-2-[2-[2-(2-methoxyethoxy)ethoxy)ethoxy]-4,5-dinitrobenzene.

2-[2-[2-(2-Methoxyethoxy)ethoxy)ethoxy]-4,5-dinitrophenol, sodium salt (3.00 g, 8.13 mmol), ethyl-2-iodoacetate (1.20 mL, 10.1 mmol), potassium carbonate (1.400 g, 10.1 mmol) and acetonitrile (50 mL) were combined in a flask and the reaction mixture was heated at reflux for 6.5 hours. The reaction mixture was transferred to a separatory funnel and partitioned between CHCl$_3$ (ca. 150 mL) and water (50 mL). The organic phase was washed with water (3×50 mL), solvent volume was reduced to 50 mL on a rotary evaporator, and washed again with water (2×100 mL). Remaining solvent was removed and the residue dried overnight in vacuo. The crude product was purified by silica gel chromatography using 2% MeOH in CHCl$_3$ as eluent. The title compound was isolated as a faint yellow solid (3.035 g, 86.4%). $^1$H NMR (CDCl$_3$): δ 1.33 (t, 3H, CH$_2$CH$_3$); 3.37 (s, 3H, OCH$_3$); 3.55 (m, 2H, CH$_2$CH$_2$O); 3.55 (m, 2H, CH$_2$CH$_2$O); 3.66 (m, 4H, CH$_2$CH$_2$O); 3.74 (m, 2H, CH$_2$CH$_2$O); 3.95 (m, 2H, CH$_2$CH$_2$O); 4.30 (q, 2H, CH$_2$CH$_3$); 4.38 (m, 2H, CH$_2$CH$_2$O); 4.83 (s, 2H, CH$_2$CO$_2$Et); 7.33 (s, 1H, ArH), 7.51 (s, 1H, ArH). $^{13}$C NMR (CDCl$_3$): δ 14.1, 58.9, 61.8, 66.6, 69.4, 70.2, 70.5, 70.6, 71.0, 71.9, 109.9, 110.5, 136.0, 138.0, 150.1, 152.2, 167.2. HR FAB MS, (M+H)$^+$: m/e: 433.1462 (calc. for C$_{17}$H$_{25}$N$_2$O$_{11}$, 433.1458).

1-[1-(Hydroxy)acetyl-2-oxy]-2-[2-[2-(2-methoxyethoxy)ethoxy)ethoxy]-4,5-dinitrobenzene, 13.

An aqueous solution of sodium hydroxide (1N, 10 mL) was added to a solution of 1-[1-(ethyloxy)acetyl-2-oxy]-2-[2-[2-(2-methoxyethoxy)ethoxy)ethoxy]-4,5-dinitrobenzene (2.915 g, 6.75 mmol) in tetrahydrofuran (50 mL). The solution was stirred for 2 hours at ambient temperature, whereupon tetrahydrofuran was evaporated under reduced pressure. The resulting aqueous solution was washed with CHCl$_3$ (2×40 mL), then neutralized with aqueous hydrochloric acid (1N, 10 mL). Water was decanted from the resulting oil, which was washed with water (20 mL), decanted again, and freeze-dried. The resulting orange solid was dissolved in CHCl$_3$ (100 mL) and washed with water (ca. 50 mL). The aqueous wash was back-extracted with CHCl$_3$ (ca. 100 mL) and solvent was removed from the combined CHCl$_3$ extracts under reduced pressure to yield 2.271 g compound 13 (83.3%). $^1$H NMR (CDCl$_3$): δ 3.39 (s, 3H, OCH$_3$); 3.60 (m, 2H, CH$_2$CH$_2$O); 3.70 (m, 6H, CH$_2$CH$_2$O); 3.90 (m, 2H, CH$_2$CH$_2$O); 4.30 (m, 2H, CH$_2$CH$_2$O); 4.84 (s, 2H, CH$_2$CO$_2$H); 7.41 (s, 1H, ArH), 7.42 (s, 1H, ArH); 10.10 (br s, 1H, CO$_2$H). $^{13}$C NMR (CDCl$_3$): δ 58.7, 67.3, 68.9, 70.0, 70.1, 70.5, 70.6, 71.6, 109.6, 112.7, 136.4, 137.6, 150.1, 151.8, 169.5. HR FAB MS, (M+H)$^+$: m/e: 405.1135 (calc. for $C_{15}H_{21}N_2O_{11}$, 405.1145).

n-{3,4-Bis-[(9H-fluoren-9-ylmethoxycarbonyl)amino]butyl}-2-(2-{2-[2-(2-methoxyethoxy)ethoxy]ethoxy}-4,5-dinitrophenoxy)acetamide, 14.

Compound 13 (0.100 g, 0.247 mmol) is suspended in dichloromethane (15 mL) together with N,N-dimethylformamide (0.1 mL), and oxalyl chloride (0.876 g, 0.60 mL, 6.90 mmol) in dichloromethane (5.0 mL) is added dropwise during 30 min, with stirring under a slow stream of argon. When the evolution of gasses ceases, the reaction vessel is covered by septum and stirred at room temperature for 6 h. The reaction mixture is then evaporated in vacuo and dried in high vacuum (1.0 Torr) for 1 h. The reaction vessel is then covered by septum and a mixture of benzene and dichloromethane (5:1, 20 mL) is added through septum, with slow stirring. After 0.5 h, the stirring is discontinued and the crude acid chloride is taken up via syringe and added through a septum to an ice/water cooled solution of $N^1,N^2$-bis-(9H-fluoren-9-ylmethoxycarbonyl)butane-1,2,4-triamine 12 (0.272 mmol) in a mixture of dichloromethane-pyridine (10:0.1, 20 mL). The reaction mixture is stirred for 30 min, quenched with 0.1 M aqueous hydrochloric acid (50 mL), diluted by chloroform (100 mL) and washed by ice-cold aqueous 0.5 M hydrochloric acid (150 mL). The organic layer is washed twice with water (50 mL), aqueous sodium hydrogen carbonate solution (50 mL), dried over sodium sulfate and evaporated in vacuum to give yellow oil. Flash column chromatography on silica using 1% of methanol in dichloromethane yields pure product 14.

Following the procedures of Example 1, the resulting dinitrobenzene cpd. 14 is converted to the corresponding diaminobenzene, which is reacted with tripyrrane to give the sp$^3$ nonaromatic macrocycle. This macrocycle is then oxidized and metallated with gadolinium acetate hydrate to give the gadolinium(III) complex 15, which is then treated with dimethylamine in a tetrahydrofuran-methanol mixture with stirring overnight at 0° C. to remove the Fmoc protecting groups. The resulting Gd(III)-texaphyrin is reacted with potassium tetrachloroplatinate(II) to give the cis-dichloroplatinum(II) complex 16.

Example 3

The synthesis of texaphyrin-cisplatin conjugates (cpds 21 and 22), utilizing a dicarboxylate platinum(II) metal chelating site following Reaction Scheme C.

2-[2-(2-{2-[2-(2-Methoxyethoxy)ethoxy]ethoxy}-4,5-dinitrophenoxy)acetylcarbamoyl]-2-succinic acid dimethyl ester, 17.

While under a constant pressure of argon, 2-[2-(2-{2-[2-(2-methoxyethoxy)ethoxy]ethoxy}-4,5-dinitrophenoxy) acetic acid 13 (0.100 g, 0.247 mmol) was suspended in dichloromethane (15 mL). N,N-dimethylformamide (0.1 ml) was added, followed by dropwise addition of a dichloromethane solution (5.0 mL) of oxalyl chloride (0.876 g, 0.60 mL, 6.90 mmol) over a period of 30 min. When the evolution of gasses ceases, the reaction vessel was covered by septum and stirred at room temperature for 6 hours. The volatiles were then evaporated and the remaining solids dried in high vacuum (1.0 Torr) for 1 hour. The reaction vessel was then covered by septum and a mixture of benzene and dichloromethane (5:1, 20 mL) was added by syringe upon slow stirring. After 0.5 hour, the crude acid chloride was taken up via syringe and added to a solution of dimethyl aspartate (0.161 g, 1.0 mmol) in dichloromethane-pyridine (10:1, 20 mL) that had been prepared under argon and cooled in ice-water bath. The reaction mixture was stirred overnight and partitioned between chloroform (20 ml) and ice-cold 10% aqueous citric acid (150 mL). The organic layer was washed twice more with citric acid solution (2×30 mL), once with water (50 mL) and once with aqueous sodium hydrogen carbonate solution (50 mL). After drying over sodium sulfate, the organic solvents were evaporated under vacuum to give a yellow oil (0.265 g). Flash column chromatography on silica using 3% methanol in dichloromethane yielded 0.078 g of pure product (58% of theoretical yield).

$^1$H-NMR (CHCl$_3$): δ 2.84 (1H, dd, J=4.5, 17.2 Hz, betaH), 3.01 (1H, dd, J=4.5, 17.2 Hz, betaH), 3.34 (s, 3H, OCH$_3$), 3.49 (m, 2H, OCH$_2$), 3.55 (m, 4H, OCH$_2$), 3.61 (m, 2H, OCH$_2$), 3.68 (s, 3H, CO$_2$CH$_3$), 3.75 (s, 3H, CO$_2$CH$_3$), 3.94 (m, 2H, OCH$_2$), 4.38 (m, 2H, OCH$_2$), 4.85 (m, 2H, OCH$_2$CO$_2$), 7.37 (s, 1H, dinitrophenylCH), 7.51 (s, 1H, dinitrophenylCH). $^{13}$C-NMR (CHCl$_3$): δ 36.3, 48.5, 51.8, 52.9, 59.3, 67.1, 69.7, 70.6, 70.9, 71.0, 71.5, 72.4, 109.9, 110.4, 136.5, 138.1, 150.7, 152.7, 169.7, 171.1, 171.5. MS-Cl (547.47, $C_{21}H_{29}N_3O_{14}$): 548.

2-[2-(2-{2-[2-(2-Methoxyethoxy)ethoxy]ethoxy}-4,5-dinitrophenoxy)acetylcarbamoyl]-2-succinic acid, 18.

2-[2-(2-{2-[2-(2-methoxyethoxy)ethoxy]ethoxy}-4,5-dinitrophenoxy)-acetylcarbamoyl]-2-succinic acid dimethyl ester, 17, (0.055 g, 0.10 mmol) was dissolved in ethanol-tetrahydrofuran mixture (1:1, 5 mL) and aqueous sodium hydroxide (0.30 mmol in 1 mL) was added. The reaction mixture was stirred at room temperature for 3 days, after which no starting material was present according to MS. The solution is then acidified by adding 1M HCl solution. The product is extracted from the aqueous mixture with dichloromethane, and the organic solution is washed twice with 30 mL of saturated sodium chloride and dried over sodium sulfate. The organic solvent is removed under vacuum.

Following the procedures of Example 1, the resulting dinitrobenzene compound 18 is converted to the corresponding diaminobenzene, which is reacted with tripyrrane 6 in isopropyl alcohol to give the sp$^3$ nonaromatic macrocycle, 19. This macrocycle is then oxidized and metallated with gadolinium acetate hydrate to give the gadolinium(III) complex, 20. The diacid gadolinium complex is platinated by reaction of Pt(NH$_3$)$_2$Cl$_2$ in dimethyl sulfoxide (DMSO) to yield the cis-platin conjugate complex, 21.

Alternatively, a diamine platinum complex, 22, is synthesized by adding an aqueous (or DMSO) solution of the gadolinium complex 20 to an aqueous solution of (1,2-diaminopropane)Pt(II)(NO$_3$)$_2$ (prepared from (1,2-diaminopropane)PtI$_2$ which was synthesized from K$_2$PtCl$_4$, with both preparations according to Rochon, F. D.; Kong, P. C. *Can. J. Chem.* 1986, 64,1894).

Example 4

The synthesis of texaphyrin-doxorubicin conjugates (24) follows Reaction Scheme D.
4A. Amide-linked doxorubicin conjugate of gadolinium(III) complex of 4,5-diethyl-10,23-dimethyl-9,24-bis(3-hydroxypropyl)-16-carboxyethoxy-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene 24.

The gadolinium(III) complex of 4,5-diethyl-10,23-dimethyl-9,24-bis(3-hydroxypropyl)-16-carboxyethoxy-13,20,25,26,27-pentaazapentacyclo-[20.2.1.1$^{3,6}$.1$^{8,11}$.0$^{14,19}$] heptacosa-1,3,5,7,9,11(27),12,14,16,18,20,22(25),23-tridecaene 23 (21 mg, 0.02298 mmol), N-hydroxysuccinimide (8 mg, 0.0699 mmol) and 1,3-dicyclohexylcarbodiimide (48 mg, 0.2298 mmol) were dried under high vacuum for 18 h in a 10 mL round-bottom flask with a stir-bar. Crystalline doxorubicin hydrochloride (20 mg, 0.03448) was rinsed into the flask using anhydrous dimethylformamide (1.5 mL). A 28 μL aliquot of the reaction mixture was immediately removed and used for HPLC analysis. The temperature of the reaction was increased to 30° C. Aliquots of the reaction were removed for HPLC analysis at 1.5 h and 2.25 h. After 3.5 h, when the target peak had reached a maximum of 64% by HPLC analysis, the reaction was allowed to cool to room temperature and was quenched by the dropwise addition in to ether (40 mL). The resulting fine. light-brown precipitate was filtered over a medium-fritted glass funnel, rinsed with ether (5 mL), and dried under high vacuum for 1 h. The crude doxorubicin conjugate was dissolved in methanol (2 mL) and diluted with 33 mM ammonium acetate buffer (pH 4.2, 5 mL). The dark solution was passed through a 20 cc, ′C18 reversed-phase (Sep-Pak™) column. Conjugated material, retained in a ¼–½ inch band at the at of the column, was then eluted from the column using 30% acetonitrile/70% 33 mM ammonium acetate buffer (200 mL). Acetonitrile (35 mL) was removed by rotary evaporation under reduced pressure, whereupon the resulting solution of purified conjugate in approximately 10% acetonitrile/buffer was loaded on a fresh 20 cc, ′C18 reversed-phase column. The doxorubicin conjugate was retained at the top of the column as salts were washed out using distilled water (120 mL). The purified, desalted conjugate was eluted from the Sep-Pak using methanol (40 mL). Solvent was removed by rotary evaporation under reduced pressure and the residue was dried under high vacuum for 1 h. The dried residue was suspended in acetone (40 mL), stirred for 20 minutes, filtered and dried under high vacuum for 17 h to yield the title compound (7 mg, 21%).

4B. Amide-linked doxorubicin conjugate of dysprosium(III) complex of 4,5-diethyl-10,23-dimethyl-9,24-bis(3-hydroxypropyl)-16-carboxyethoxy-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene (24, where Gd is replaced by Dy).

The dysprosium(III) complex of 4,5-diethyl-10,23-dimethyl-9,24-bis(3-hydroxypropyl)-16-carboxyethoxy-13,20,25,26,27-pentaazapentacyclo-[20.2.1.1$^{3,6}$.1$^{8,11}$.0$^{14,19}$] heptacosa-1,3,5,7,9,11(27),12,14,16,18,20,22(25),23-tridecaene 23 (where Gd is replaced by Dy) (20 mg, 0.0220 mmol) and N-hydroxysuccinimide (8 mg, 0.0699 mmol) were dried under high vacuum for 18 h in a 10 mL round-bottom flask with a stir-bar. 1,3-Dicyclohexylcarbodiimide (45 mg, 0.2298 mmol) and anhydrous dimethylformamide (1.5 mL) were added to the flask and the resulting solution was stirred for 17 h. Doxorubicin hydrochloride (20 mg, 0.03448) was added to the flask and the reaction was stirred for a further 17 h. Methanol (1 mL) and 33 mM ammonium acetate buffer (4 mL) were added to the flask and the resulting mixture was passed through a 20 cc, ′C18 reverse-phase (Sep-Pak™) column. Conjugated material, which was retained in a ¼–½ inch band at the top of the column, was then eluted from using 40% acetonitrile/60% 33 mM ammonium acetate buffer (150 mL). Acetonitrile was removed by rotary evaporation under reduced pressure, whereupon the resulting solution of purified conjugate in approximately 10% acetonitrile/buffer was loaded on a fresh 20 cc, ′C18 reversed-phase column. The doxorubicin conjugate was retained at the top of the column as salts were eluted using distilled water (80 mL). The purified, desalted conjugate was eluted from the column using methanol (40 mL). Solvent was removed by rotary evaporation under reduced pressure and the residue was dried under high vacuum for 17 h to yield the title compound (4 mg, 12%). FAB MS, (M+H)$^+$: m/e 1310.3 (calcd for DyC$_{63}$H$_{65}$N$_6$O$_{15}$, 1308.75).

Example 5

The synthesis of a texaphyrin-distamycin conjugate (30) follows Reaction Scheme E.

Distamycin-PegDinitrobenzene Conjugate 27.

Aminodistamycin 25 was obtained by a reduction of 50 mg (0.1 mmol) of nitrodistamycin according to a procedure previously described (Taylor, J. S.; Schultz, P. G.; Dervan, P. B. *Tetrahedron* 1984, 40, 457–465). After reduction with Pd/C, the crude solution of 25 in 7 mL of anhydrous DMF was filtered through a thin layer of Celite. DinitroPeg functionalized monocarboxylate 26 (40 mg, 0.08 mmol), was added, followed by 0.1 mL of dry pyridine. A solution of EDC (29 mg, 0.15 mmol) in 1 mL of anhydrous DMF was then added, followed by HOBt (4.5 mg, 0.03 mmol). The resulting reaction mixture was stirred at room temperature under argon in the absence of light for ca. 12 hours. The solvents were then evaporated and the resulting product purified via column chromatography using silica gel as the solid support and an 8% ammonia-saturated methanol in dichloromethane as the eluent. The yield of compound 27 was 57 mg (75%). $^1$H NMR (300 MHz, CD$_2$Cl$_2$): d 1.68 (2H, pentet, CH$_2$CH$_2$CH$_2$), 2.24 (6H, s, N(CH$_3$)2), 2.40 (2H, t, CH$_2$CH$_2$CH$_2$N), 3.26 (3H, s, OCH$_3$), 3.39 (2H, m, CH$_2$CH$_2$CH$_2$N), 3.47 (2H, m, OCH$_2$), 3.59 (6H, m, OCH$_2$), 3.75 (3H, s, NCH$_3$), 3.79 (5H, s, NCH$_3$+OCH$_2$), 3.85 (7H, m, NCH$_3$+OCH$_2$), 3.91 (2H, m, OCH$_2$), 4.05 (2H, s, OCH$_2$CO), 4.17 (2H, t, OCH$_2$), 4.26 (2H, m, OCH$_2$), 6.54 (1H, d, pyrrolic CCHC), 6.65 (1H, d, pyrrolic CCHC), 6.67 (1H, d, pyrrolic CCHC), 6.97 (1H, d, pyrrolic CHN), 7.14 (1H, d, pyrrolic CHN), 7.19 (1H, d, pyrrolic CHN), 7.31 (1H, s, benzene CH), 7.36 (1H, s, benzene CH), 7.72 (1H, t, NH), 8.07 (1H, s, NH), 8.20 (1H, s, NH), 8.59 (1H, s, NH). $^{13}$C NMR (75 MHz, CD$_2$Cl$_2$): d 26.43, 36.55, 36.61, 36.64, 39.42, 45.41, 58.76, 58.91, 69.36, 69.54, 73.02, 70.62, 70.67, 70.82, 71.12, 71.29, 72.06, 103.21, 103.89, 104.53, 108.96, 109.09, 118.56, 119.18, 119.41, 120.90, 122.08, 122.25, 123.47, 123.62, 124.05, 136.57, 136.69, 151.64, 151.83, 158.95, 159.11, 161.96, 167.81. HRMS FAB calcd for C$_{42}$H$_{59}$N$_{10}$O$_{15}$ ([M+H]$^+$) 943.4161, obsd 943.4142.

Synthesis of Lutetium(II) Texaphyrin-Distamycin Conjugate 30.

In a 250 hydrogenation vessel, 10% palladium on carbon (20 mg) was mixed with 5 mL of methanol. To this suspension, the dinitroPeg distamycin conjugate 27 (220 mg, 0.23 mmole) was added with 10 mL of methanol and HCl (0.020 mL, 0.25 mmole). The mixture was hydrogenated at 50 psi until the reaction solution in the vessel was deemed colorless. The resulting diamine was confirmed by thin-layer chromatography (tlc) in 10% MeOH saturated with NH$_3$/90% CH$_2$Cl$_2$ after 5 h. The diamine product was filtered through Celite into a 250 mL round bottom flask and used without purification. To this flask, 2,5-bis[(5-formyl-3-(3-hydroxypropyl)-4-methylpyrrol-2-yl)methyl]-3,4-diethylpyrrole 28 (110 mg, 0.23 mmol) and 50 mL methanol were added and the suspension heated to 45–50° C. for 1.5 h. The reaction was deemed complete by tlc (i.e., appearance of nonaromatic macrocycle 29) and UV/vis absorption (372 nm). The red solution was concentrated to dryness, and the resulting solid was dried for 12 h. The nonaromatic macrocycle 29 was used without further purification.

The macrocyclic ligand 29 (300 mg, 0.216 mmol) was then oxidatively metallated using lutetium(III) acetate hydrate (137 mg, 0.324 mmol) and triethylamine (0.3 mL) in air-saturated methanol (150 mL) at reflux (~7 h). After completion of the reaction (as judged by the optical spectrum of the reaction mixture and tlc), the deep green solution was cooled to room temperature, filtered through a pad of Celite, and the solvent was removed under reduced pressure and dried in vacuo for 12 h. The dark green/brown solid was suspended in acetone (20 mL), stirred for 20 min at room temperature, and then filtered to wash away the red/brown impurities (incomplete oxidation products and excess triethylamine). In a 100 mL round bottom flask, the crude complex (315 mg) was dissolved into MeOH (10 mL); to the resulting deep green solution were added 1 mL of water and acetic acid-washed SAY-54 zeolite (1 g). The resulting mixture was agitated or shaken for 2 h, then filtered to remove the zeolite. The zeolite cake was rinsed with MeOH (10 mL) and the rinse solution added to the filtrate. The filtrate was concentrated to dryness. The resulting bis-acetate lutetium(III) texaphyrin-distamycin conjugate 30 was recrystallized from anhydrous methanol/diethylether to afford 200 mg (54%, yield based on starting dinitroPeg distamycin conjugate) of a dark green solid. For complex 7: Electrospray MS [M–OAc$^-$]$^+$: m/e 1556.6 (found for $C_{72}H_{95}LuN_{13}O_{15}$); FAB MS, [M–2OAc$^-$]$^+$: m/e 1497; HRMS, [M–2OAc$^-$]$^+$: m/e 1497.6298 (calcd. for $[C_{70}H_{92}LuN_{13}O_{13})]^+$, 1497.6345). This compound was further characterized by HPLC.

Example 6

The synthesis of a gadolinium(III) texaphyrin cis-diaminodichloroplatinum(II) conjugate (41) follows Reaction Scheme F.

2-[2-(2-Benzylaminoethoxy)ethoxy]ethanol 2

2-[2-(2-Chloroethoxy)ethoxy]ethanol 31 (9.273 g, 55 mmol) and benzylamine (26.3 mL, 240 mmol) were dissolved in absolute acetonitrile (150 mL) whereupon potassium carbonate (25.0 g, 180 mmol) was added. The suspension was heated at reflux with vigorous stirring under an argon atmosphere for 18 hours. The suspension was allowed to cool to room temperature, diluted with acetonitrile (100 mL) and filtered through a Celite™ pad. The acetonitrile was removed under reduced pressure and the unreacted benzylamine distilled from the concentrated pale greenish oil under high vacuum (90° C., 5 torr). The resulting viscous oil (14.2 g) was purified by flash chromatography using 13% methanol in dichloromethane as the eluent. Fractions contained the desired product ($R_f$=0.45) were combined, solvent removed under reduced pressure, and the residue dried in vacuo to yield the title compound as a viscous oil (10.1 g, 77%). CIMS (MH$^+$): m/e 240. $^1$H-NMR (CDCl$_3$): δ 7.31 (m, 5H, phenyl), 3.79 (s, 2H, CH$_2$-Ph), 3.70–3.61 (m, 12 H, OCH$_2$CH$_2$O). $^{13}$C-NMR (CDCl$_3$): δ 140.3, 129.0, 128.8, 127.6, 73.3, 70.9, 70.8, 70.7, 62.0, 54.4, 49.0.

2-[2-(Benzyl-{2-[2-(2-hydroxy-ethoxy)ethoxy] ethyl}amino)ethyl]-phthalimide 33

2-[2-(2-Benzylaminoethoxy)ethoxy]ethanol 32 (4.786 g, 20 mmol) and 2-bromoethylphthalimide (5.59 mL, 22 mmol) were dissolved in absolute acetonitrile (100 mL). Potassium carbonate (6.91 g, 50 mmol) was added, and the suspension was heated at reflux with vigorous stirring under an argon atmosphere for 18 hours. The suspension was allowed to cool to room temperature, diluted with acetonitrile (100 mL) and filtered through a Celite™ pad. The acetonitrile was removed under reduced pressure and the residue was purified by flash chromatography using a 1:1 mixture of 40% acetone in hexanes and chloroform as the eluent. Fractions contained the desired product ($R_f$=0.35) were combined, solvent removed under reduced pressure, and the residue dried in vacuo to provide the title compound 33 (4.2 g, 51%). CIMS (MH$^+$): 413. $^1$H-NMR (CDCl$_3$): δ 7.82 (m, 2H, phthalimide), 7.70 (m, 2H, phthalimide), 7.21 (m, 5H, phenyl), 4.39 (s, 2H, CH$_2$-Ph), 3.70–3.21 (m, 12 H, OCH$_2$CH$_2$O), 2.85 (q, 2H, J=6.1 Hz, phthalimido-ethylene), 2.79 (q, 2H, J=6.4 Hz, phthalimido-ethylene). $^{13}$C-NMR (CDCl$_3$): δ 168.8, 139.8, 134.3, 132.8, 129.4, 128.7, 128.0, 127.6, 73.1, 71.0, 70.8, 62.3, 59.9, 53.7, 52.4, 48.2, 45.1.

2-[2-(Benzyl-{2-[2-(2-methanesulfonyloxy-ethoxy)ethoxy] ethyl}-amino)ethyl]phthalimide 34

2-[2-(Benzyl-{2-[2-(2-hydroxy-ethoxy)ethoxy] ethyl}amino)ethyl]phthalimide 33 (2.774 g, 6.7 mmol) was dissolved in mixture of pyridine (20 mL) and dichloromethane (100 mL) and cooled in an ice bath. Methanesulfonyl chloride (0.63 mL, 8 mmol) was added and the resulting solution was stirred at 0° C. for 16 h. (The progress of the reaction was followed by TLC using a 1:1 mixture of 40% acetone in hexanes and chloroform as the eluent. The starting material has $R_f$=0.35, while the product has $R_f$=0.50.) Saturated aqueous sodium bicarbonate was added, and after 30 min of stirring, the organic phase was washed with 0.5 M hydrochloric acid and again with saturated aqueous sodium bicarbonate. The solution was dried over sodium sulfate and solvent was removed under reduced pressure. The resulting crude oily product 34 (3.152 g, 96%) was used in the next step without further purification. CIMS (M+): 491.

2-{2-[Benzyl-(2-{2-[2-(2-{2-[2-(2-methoxy-ethoxy) ethoxy]ethoxy}-4,5-dinitro-phenoxy)ethoxy]ethoxy}ethyl) amino]ethyl}phthalimide 36

2-(2-(2-Methoxy)ethoxy)ethoxy)ethoxy-4,5-dinitrophenol 35 (1.732 g, 5 mmol) and mesylate 34 (3.152 g, 6.43 mmol) were dissolved in acetonitrile (70 mL). Potassium carbonate (2.764 g, 20 mmol) was added and the resulting suspension heated at reflux with vigorous stirring under an argon atmosphere for 48 hours. The suspension was allowed to cool to room temperature, diluted with acetonitrile (50 mL) and filtered through a Celite™ pad. Acetonitrile was removed under reduced pressure and the crude oily product purified by flash chromatography using a 1:1 mixture of 30% acetone in hexanes and chloroform as an eluent. Fractions containing product ($R_f$=0.55) were combined, solvent removed under reduced pressure, and the residue dried in vacuo to provide the title compound 36 as a yellow oil (2.2 g, 59%). CIMS (MH$^+$): 741. $^1$H-NMR (CD$_2$Cl$_2$): δ 7.88–7.70 (m, 4H, phthalimide), 7.48 (s, 1H, dinitrocatechol), 7.39 (s, 1H, dinitrocatechol), 7.21 (m, 5H, phenyl), 4.25 (m, 4H, aryl-OC$\underline{H}_2$), 3.85 (m, 4H, aryl-OCH$_2$ C$\underline{H}_2$), 3.72–3.45 (m+s, 18H, s: CH$_2$-Ph, m: C$\underline{H}_2$OC$\underline{H}_2$ C$\underline{H}_2$O), 3.28 (s, 3H, OCH$_3$), 2.79 (q, 2H, J=6.2 Hz, phthalimido-ethylene), 2.75 (q, 2H, J=6.4 Hz, phthalimido-ethylene). $^{13}$C-NMR (CD$_2$Cl$_2$): δ 168.6, 152.2, 140.2, 137.1, 134.3, 132.8, 129.2, 128.7, 128.4, 128.3, 127.2, 123.4, 109.6, 109.5, 72.4, 72.3, 71.5, 71.4, 71.1, 71.0, 70.9, 70.8, 70.5, 70.4, 69.8, 69.7, 59.7, 59.2, 52.3, 36.7.

4,5-Diethyl-17-(2-[2-(2-methoxyethoxy)ethoxy]ethoxy)-16-(2-[2-(2-(2-phthalimidoethylamino)ethoxy)ethoxy] ethoxy)-9,24-bis(3-hydroxypropyl)-10,23-dimethyl-13,20, 25,26,27-pentaazapentacyclo[20.2.1.1$^{3,6}$.1$^{8,11}$.0$^{14,19}$]-heptacosa-3,5,8,10,12,14(19),15,17,20,22,24-undecaene 38

2-{2-[Benzyl-(2-{2-[2-(2-{2-[2-(2-methoxy-ethoxy) ethoxy]ethoxy}-4,5-dinitro-phenoxy)ethoxy]ethoxy}ethyl) amino]ethyl}phthalimide 36 (1.0 g; 1.35 mmol) was dissolved in methanol (250 mL) in a Schlenk flask. Concentrated hydrochloric acid (2 mL) was added, and the resulting solution transferred via cannula to a Parr flask containing Pearlman's catalyst (100 mg) under a strict nitrogen atmosphere. The flask was placed on a Parr hydrogenation apparatus and hydrogen pressure was maintained at ca. 50 psi for 14 h. Catalyst was removed by filtration through a pad of Celite™ filter agent under an inert atmosphere. The solution of intermediate 2-{2-{2-[2-(2-{2-[2-(2-methoxy-ethoxy)ethoxy]ethoxy}-4,5-diamino-phenoxy)ethoxy]ethoxy}-ethyl)amino]ethyl}phthalimide in methanol was transferred to a flask containing a suspension of 2,5-bis[(5-formyl-3-(3-hydroxypropyl)-4-methylpyrrol-2-yl)methyl]-3,4-diethylpyrrole 37 (650 mg, 1.35 mmol) in methanol (250 mL) and stirred overnight. Solvent was removed under reduced pressure and the residue was dried in vacuo to provide the crude title compound as a crimson-red powdery solid (1.40 g, quantitative yield). ESMS ($MH^+$): m/e 1036.7. HRMS ($MH^+$): m/e 1035.5663; calc. for $C_{57}H_{77}N_7O_{11}$, 1035.5681).

Gadolinium(III) complex of 4,5-diethyl-17-(2-[2-(2-methoxyethoxy)ethoxy]ethoxy)-16-(2-[2-(2-(2-phthalimidoethylamino)ethoxy)ethoxy]ethoxy)-9,24-bis(3-hydroxypropyl)-10,23-dimethyl-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene 39

In a 500 mL single-neck flask, fitted with a short condenser, the hydrochloride salt of 4,5-diethyl-17-(2-[2-(2-methoxyethoxy)ethoxy]ethoxy)-16-(2-[2-(2-(2-phthalimidoethylamino)ethoxy)ethoxy]ethoxy)-9,24-bis(3-hydroxypropyl)-10,23-dimethyl-13,20,25,26,27-pentaazapentacyclo[20.2.1.1$^{3,6}$.1$^{8,11}$.0$^{14,19}$]heptacosa-3,5,8,10,12,14(19),15,17,20,22,24-undecaene 38 (1.40 9, 1.3 mmol), gadolinium acetate hydrate (1.06 g, 2.6 mmol), triethylamine (1.8 mL, 13 mmol) and methanol (500 mL) were combined and heated at reflux open to the atmosphere. After a total of 4 h the reaction was cooled to room temperature, solvents were removed under reduced pressure. The residue was dried in vacuo to afford the title compound as a fine green solid (2.28 g, xx%). ES MS, ($MH^+$): m/e 1247.4; (calcd for $C_{59}H_{75}GdN_7O_{13}$, 1247.5). UV-visible $\lambda_{max}$ (nm): 740, 472, 412, 352.

Gadolinium(III) complex of 4,5-diethyl-17-(2-[2-(2-methoxyethoxy)ethoxy]ethoxy)-16-(2-[2-(2-(2-aminoethylamino)ethoxy)ethoxy]ethoxy)-9,24-bis(3-hydroxypropyl)-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene 40

The gadolinium(III) complex of 4,5-diethyl-17-(2-[2-(2-methoxyethoxy)-ethoxy]ethoxy)-16-(2-[2-(2-(2-phthalimidoethylamino)ethoxy)-ethoxy]ethoxy)-9,24-bis(3-hydroxypropyl)-10,23-dimethyl-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene 39 (1.14 g, 859 umol) was dissolved in methanol (140 mL) and 40% aqueous methylamine (100 mL) and stirred at ambient temperature for 1 h. Solvents were removed under reduced pressure and the residue dried in vacuo overnight. The residue was dissolved in 33 mM ammonium acetate buffer, pH 4.3 (125 mL) and the buffered solution of crude complex was loaded onto a Sep-pak™ reverse-phase column (tC18, 10 g, Waters, Milford, Mass.) prepared with a thin layer of Celite™ filter aid. Complex was washed on the columns with 33 mM ammonium acetate buffer, pH 4.3 (250 mL) and then eluted with 30–50% methanolic buffer (400 mL). Fractions containing product were combined and methanol removed under reduced pressure. The resulting aqueous solution was applied to a single Sep-pak column, washed with water, then eluted with methanol (25 mL). Volatile solvent was removed under reduced pressure, and the product dried in vacuo to provide the title compound as a green powder (202 mg, 20%). ES MS, ($MH^+$): m/e 1158.6; (calcd for $C_{49}H_{70}GdN_7O_9$, 1158.1). UV-visible $\lambda_{max}$ (nm): 740, 472, 414, 338.

cis-Dichloroplatinum(II) complex of gadolinium(III) complex of 4,5-diethyl-17-(2-[2-(2-methoxyethoxy)ethoxy]ethoxy)-16-(2-[2-(2-(2-aminoethylamino)ethoxy)ethoxy]-ethoxy)-9,24-bis(3-hydroxypropyl)-10,23-dimethyl-13,20,25,26,27-pentaazapentacyclo[20.2.1.1$^{3,6}$.1$^{8,11}$.0$^{14,19}$] heptacosa-1,3,5,7,9,11(27),12,14,16,18,20,22(25),23-tridecaene 41

To a solution of the gadolinium(III) complex of 4,5-diethyl-17-(2-[2-(2-methoxyethoxy)ethoxy]ethoxy)-16-(2-[2-(2-(2-aminoethylamino)ethoxy)ethoxy]-ethoxy)-9,24-bis(3-hydroxypropyl)-10,23-dimethyl-13,20,25,26,27-pentaazapentacylclo[20.2.1.1$^{3,6}$.1$^{8,11}$.0$^{14,19}$]heptacosa-1,3,5,7,9,11(27),12,14,16,18,20,22(25),23-tridecaene 40 (0.202 g, 163 umol) in methanol (15 mL) was added dropwise a solution of $K_2PtCl_4$(0.068 g, 164 umol) in $H_2O$ (5 mL). The reaction mixture was allowed to stand at room temperature overnight with protection from light. The resulting precipitate was filtered, washed with of cold water (5 mL) and methanol (10 mL) and dried in vacuo. The filtrate was concentrated under reduced pressure to obtain additional crops of precipitate upon standing, which were washed and dried as above. All crops were combined to provide the title compound as an amorphous dark green-brown solid (105 mg, 43%). The platinum complex displayed poor solubility in water and several organic solvents (methanol, ethanol, acetone, ether), but was dissolved readily in DMF and DMSO. UV-visible $\lambda_{max}$ (nm): 740, 472, 414. FABMS (M+): m/e 1383.6 (calculated for $C_{51}H_{73}GdN_7O_{11}Cl_2Pt$, 1383.4).

Example 7

The synthesis of a bis-2-nitroimidazole derivative of GdTex follows Reaction Scheme G.

Gadolinium(III) complex of 4,5-diethyl-16,17-bis(2-[2-(2-methoxyethoxy)ethoxy]-ethoxy)-9,24-bis[3-(2-nitroimidazoyl)propyl]-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene Gadolinium(III) complex of 4,5-diethyl-16,17-bis(2-[2-(2-methoxyethoxy)ethoxy]ethoxy)-9,24-bis(3-hydroxypropyl)-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene (1.000 g, 0.871 mmol), triphenylphosphine (1.142 g, 4.35 mmol), and 2-nitroimidazole (493 mg, 4.36 mmol) were dried together in vacuo. Dry dichloromethane (200 mL) was added under nitrogen atmosphere with stirring to form a solution, which was then cooled using an ice bath. Diethylazodicarboxylate (686 uL, 4.36 mmol) was added dropwise, and the solution stirred at 0° C. for 5 h. Methanol (ca. 5 mL) was added, then solvent was removed under reduced pressure. CHCl3 (75 mL) was added to form a solution, which was washed with 1M ammonium acetate buffer, pH 4.3 (50 mL) and water (100 mL). Solvent was removed under reduced pressure, whereupon CHCl3 (50 mL) was added to form a solution, which was dropped into stirred Et2O (350 mL). The resulting precipitate was collected by filtration, and dissolved in methanol (50 mL) and 33 mM ammonium acetate buffer, pH 4.3 (150 mL). The solution of crude complex was loaded onto two Sep-pak™ reverse-phase columns (tC18, 10 g, Waters, Milford, Mass.) prepared with a thin layer of Celite™ filter aid. Complex was washed on the columns with buffer, pH 4.3 (200 mL), 30–35% MeOH/buffer (500 mL) and then eluted with 40–50% methanolic buffer (400 mL). Fractions containing product were combined and methanol partially removed under reduced pressure.

The resulting aqueous solution was extracted with CHCl3 (2×100 mL), methanol (50 mL) added, and extracted again with CHCl3 (2×50 mL). Solvent was removed under reduced pressure, and the product dried in vacuo overnight. The residue was dissolved in CHCl3 and washed with water (100 mL). The aquous wash was extracted with CHCl3 (3×50 mL). The combined CHCl3 extracts were dried briefly with MgSO4, and solvent removed under reduced pressure. The residue was dissolved in CHCl3 (25 mL) and dropped in stirred Et2O (200 mL). The resulting precipitate was collected by filtration and dried in vacuo to provide the title compound as a green powder (504 mg, 43%). ES MS (DTT/DTE matrix), M+: m/e 1279.5. (calc. for C48H68N7O8Gd, 1279.4).

Example 8

The synthesis of a bis(5-fluoro-2'-deoxyuridine-3'-phosphate) derivative of GdTex follows Reaction Scheme H.
Gadolinium(III) complex of 4,5-diethyl-16,17-bis(2-[2-(2-methoxyethoxy)ethoxy]-ethoxy)-9,24-bis[3-(5-fluoro-2'-deoxyuridine-3'-phosphoryl)propyl]-10,23-dimethyl-13,20, 25,26,27-pentaazapentacyclo[20.2.1.13,6.18,11.014,19] heptacosa-1,3,5,7,9,11(27),12,14,16,18,20,22(25),23-tridecaene The gadolinium(III) complex of 4,5-diethyl-16,17-bis(2-[2-(2-methoxyethoxy)ethoxy]ethoxy)-9,24-bis(3-hydroxypropyl)-10,23-dimethyl-13,20,25,26,27-pentaazapentacyclo[20.2.1.13,6.18,11.014,19]heptacosa-1, 3,5,7,9,11(27),12,14,16,18,20,22(25),23-tridecaene and 5-fluoro-2'-deoxyuridine-3'-[bis-(diisopropylamino)-2-cyanoethyl]phosphoramidite (Glen Research, Sterling, Va.) are dissolved in dichloromethane. 1H-Tetrazole (0.45M solution in acetonitrile) is added, and the solution allowed to stir. The resulting solution is washed with 0.05 M iodine solution in THF/H2O/pyridine (7:2:1) and with water. Trichloroacetic acid (3% solution in dichloromethane) is added, and the resulting solution washed with water. Solvent is removed under reduced pressure, and the residue is dissolved in methanol/40% aqueous methylamine (1:1). Methylamine is removed with a stream of dry nitrogen whereupon methanol and remaining traces of methylamine are removed under reduced pressure. Methanol and 1M ammonium acetate buffer, pH 4.3 is added to the resulting suspension to form a solution. The buffered methanolic solution of crude complex is loaded onto a Sep-pak™ reverse-phase column (tC18, 10 g, Waters, Milford, Mass.) prepared with a thin layer of Celite™ filter aid. Complex is washed on the column with 33 mM ammonium acetate buffer, pH 4.3 and eluted with methanolic buffer. Fractions containing product are combined and methanol removed under reduced pressure. The resulting aqueous solution is applied to a Sep-pak column, washed with water, then the complex is eluted with methanol. Volatile solvent is removed under reduced pressure, and the product lyophilized to provide the title compound.

Example 9

This example illustrates the preparation of a representative pharmaceutical formulation containing an active compound of Formula A, e.g., cis-Dichloroplatinum(II) complex of gadolinium(III) complex of 4,5-diethyl-17-(2-[2-(2-methoxyethoxy)ethoxy]ethoxy)-16-(2-[2-(2-(2-aminoethylamino)ethoxy)ethoxy]-ethoxy)-9,24-bis(3-hydroxypropyl)-10,23-dimethyl-13,20,25,26,27-pentaazapentacyclo[20.2.1.13,6.18,11.014,19]heptacosa-1,3,5, 7,9,11(27),12,14,16,18,20,22(25),23-tridecaene.

An injectable preparation buffered to a pH of 7.4 is prepared having the following composition:

| Ingredients | Amount |
| --- | --- |
| Active compound | 0.2 g |
| Sodium Phosphate Buffer Solution (0.8 M) | 10.0 ml |
| DMSO | 1.0 ml |
| WFI | q.s. to 100 ml |

Other compounds of Formulae A and C, such as those prepared in accordance with Examples 1–8, can be used as the active compound in the preparation of the injectable formulations of this example.

Example 10

Determination of Activity

This procedure is a modification of a procedure initially described by Mosmann, T. "Rapid Colorimetric Assay for Cellular Growth and Survival: Application to Proliferation and Cytotoxicity Assays." Immunological Methods, 65: 55–63, 1983.

A suspension of EMT-6 cells in Waymouth's complete medium (0.2 mL containing 2,000 cells) is pipetted into each well of a 96-well microtiter plate. The cells are allowed to adhere overnight. A conjugate to be tested (0.5 mM in media) is then added to each well of the first row of wells on the plate to give a 1:3 dilution of the drug. Positive and negative controls are also tested. The medium is mixed thoroughly and 100 $\mu$L is transferred to each of the next set of wells for subsequent dilutions. This serial dilution was repeated successively. The last 100 $\mu$L of the conjugate/media preparation is discarded, thus leaving the last row of wells as untreated controls. These serial transfers result in successive dilutions of 1:3, 1:9, 1:27, 1:81, and 1:243 of the original conjugate stock.

The cells are allowed to grow in the presence of the conjugate for 48 hrs. MTT [3-(4, 5-dimethylthiazol-2-yl)-2, 5-diphenyl tetrazolium bromide)] (Sigma, St. Louis, Mo.) (20 $\mu$L of 5 mg/mL) in phosphate buffered saline (PBS) is added to each well, and the plate is held in a tissue-culture incubator at 37° C. and under an atmosphere of 5% $CO_2$. After a 2–3 hr incubation period, the medium is removed and replaced with 0.1 mL isopropyl alcohol (JT Baker Chemical Co., Phillipsburg, N.J.) to dissolve fomazan crystals formed by the cells. The plate is read at a test wavelength of 570 nm and a reference wavelength of 650 nm on a multiwell spectrophotometer (ThermoMax™, Molecular Devices, Sunnyvale, Calif.). Each concentration of drug is tested in quadruplicate. Percent survival is defined as percent of the optical density (OD) of the drug-treated cells to that of the control.

The conjugates of the present invention, e.g., GdTex-doxorubicin, show activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A texaphyrin-chemotherapeutic agent conjugate, with the proviso that the chemotherapeutic agent is not a biomolecule, an antibody, nucleotide, an oligonucleotide, a peptide, a protein, a steroid, a hormone or hormone mimic, a sappphyrin, or a rubyrin.

2. A texaphyrin-chemotherapeutic agent conjugate of claim 1 wherein the chemotherapeutic agent is selected from a taxoid, an antibiotic chosen from the group consisting of dactinomycin, danorubicin, doxorubicin, 4'-deoxydoxorubicin, bleomycin, pilcamycin, mitomycin, neomycin and gentamycin, or a platinum coordination complex.

3. A texaphyrin-chemotherapeutic agent conjugate of claim 1 wherein the chemotherapeutic agent is selected from the group consisting of bleomycin, doxorubicin, taxol, taxotere, etoposide, 4-OH cyclophosphamide, 5-fluorouracil, cisplatin, or platinum coordination complexes analogous to cisplatin.

4. A texaphyrin-chemotherapeutic agent conjugate represented by Formula (A) or (B):

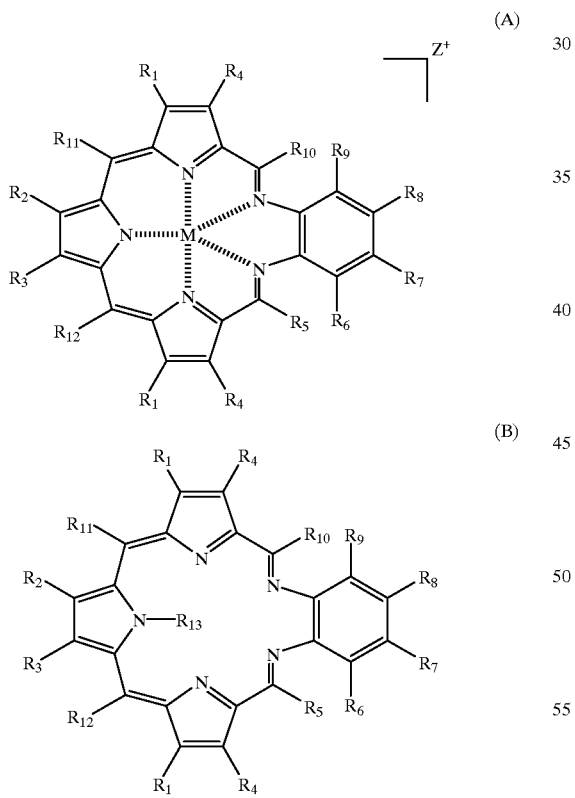

wherein,

Z is zero or an integer less than or equal to 5;

M is hydrogen, a divalent metal cation or a trivalent metal cation;

$R_1-R_4$ and $R_6-R_9$ are independently hydrogen, halide other than iodide, hydroxyl, alkyl, alkenyl, aryl, haloalkyl other than iodoalkyl, nitro, formyl, acyl, hydroxyalkyl, alkoxy, hydroxyalkoxy, saccharide, aminoalkyl, aminoalkoxy, carboxy, carboxyalkyl, carboxyamide, carboxyamidealkyl, a catalytic group, a couple to a catalytic group, a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV);

$R_5$ and $R_{10}-R_{12}$ are independently hydrogen, alkyl, alkenyl, aryl, halide other than iodide, hydroxyalkyl, alkoxy, hydroxyalkoxy, aminoalkyl, aminoalkoxy, carboxyalkyl or carboxyamidealkyl, with the proviso that:

where $R_5$ is sterically larger than hydrogen or methyl, $R_6$ is hydrogen, methyl, methoxy or halide other than iodide, where $R_6$ is sterically larger than hydrogen or methyl, $R_5$ is hydrogen, methyl, methoxy or halide other than iodide, where $R_9$ is sterically larger than hydrogen or methyl, $R_{10}$ is hydrogen, methyl, methoxy or halide other than iodide, and where $R_{10}$ is sterically larger than hydrogen or methyl, $R_9$ is hydrogen, methyl, methoxy or halide other than iodide;

$R_{13}$ is selected from alkyl, alkenyl, alkoxy or hydroxyalkyl having up to about three carbon atoms and having rotational flexibility around a first-bound carbon atom, or a pharmaceutically acceptable salt, ester or apical ligand thereof, with the proviso that at least one of $R_1-R_4$ or $R_6-R_9$ is a chemotherapeutic agent, a couple to a chemotherapeutic agent, a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV), with the proviso that the chemotherapeutic agent is not a biomolecule, an antibody, a nucleotide, an oligonucleotide, a peptide, a protein, a steroid, a hormone or hormone mimic, a sappphyrin, or a rubyrin.

5. A texaphyrin-chemotherapeutic agent conjugate of claim 4 represented by Formula (A).

6. A texaphyrin-chemotherapeutic agent conjugate of claim 5 wherein the chemotherapeutic agent is selected from a taxoid, an antibiotic chosen from the group consisting of dactinomycin, danorubicin, doxorubicin, 4'-deoxydoxorubicin, bleomycin, pilcamycin, mitomycin, neomycin and gentamycin, or a platinum coordination complex.

7. A texaphyrin-chemotherapeutic agent conjugate of claim 5 wherein the chemotherapeutic agent is selected from the group consisting of bleomycin, doxorubicin, taxol, taxotere, etoposide, 4-OH cyclophosphamide, 5-fluorouracil, cisplatin, or platinum coordination complexes analogous to cisplatin.

8. A texaphyrin-chemotherapeutic agent conjugate of claim 5 wherein at least one of $R_1-R_4$ or $R_6-R_9$ is a platinum(II) metal chelating site, a couple to a platinum(II) metal chelating site, a platinum(IV) metal chelating site, a couple to a platinum(IV) metal chelating site, a platinum(II) metal chelating site complexed with platinum(II), a couple to a platinum(II) metal chelating site complexed with platinum(II), a platinum(IV) metal chelating site complexed with platinum(IV), or a couple to a platinum(IV) metal chelating site complexed with platinum(IV).

9. A texaphyrin-chemotherapeutic agent conjugate of claim 8 wherein the platinum(II) or platinum(IV) metal chelating site is selected from the group consisting of amines, diamines, carboxylates, dicarboxylates, and amino acids.

10. A texaphyrin-chemotherapeutic agent conjugate of claim 8 wherein the platinum(II) or platinum(IV) metal chelating site is selected from the group consisting Formulae (I) through (IV):

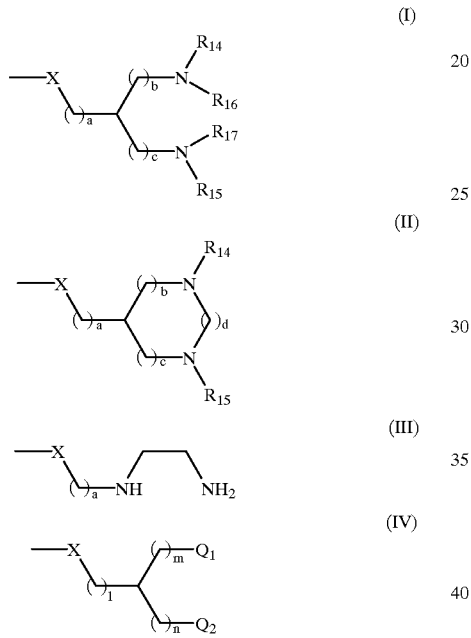

where:
X is a covalent bond or is a couple selected from —$(CH_2)_{nn}$— (where nn=1–15), —O—, —NH—, —N($R_{18}$)—, —C(O)—N($R_{18}$)—, —N($R_{18}$)—C(O)—, —O—C(O)—, —C(O)—O—, —O—C(O)—O—, —O—P(O)(OH)—O—, —O—C(O)—N($R_{18}$)—, —N($R_{18}$)—O—C(O)—, —N($R_{18}$)—C(O)—N($R_{19}$)—, —S—, —S(O)—, and —O—S(O)—O—;

$Q_1$ and $Q_2$ are independently selected from —H, —C(O)—O$^-$, —O—C(O)—O$^-$, —N($R_{20}$)—C(O)—O$^-$, —C(O)—N($R_{21}$)$_2$—, —N($R_{22}$)$_2$—, —P(O)(OH)—O$^-$, —C(S)—S—, and —N—C(S)—N($R_{23}$)$_2$—;

$R_{14}$–$R_{17}$ are independently hydrogen, alkyl, aryl, alkylaryl, alkoxyalkyl, substituted or unsubstituted residues, or are a protective masking group;

$R_{18}$–$R_{23}$ are independently hydrogen, alkyl, aryl, alkylaryl, alkoxyalkyl, substituted or unsubstituted residues;

a, b, and c are independently zero or an integer from 1 to 8;

d is an integer from 1 to 8; and l, m, and n are independently zero or an integer from 1 to 8.

11. A texaphyrin-chemotherapeutic agent conjugate of claim 10 wherein the platinum(II) or platinum(IV) metal chelating site is selected from the group consisting Formula (III) where a is zero and Formula (IV) where $Q_1$ and $Q_2$ are each —O—C(O)—O$^-$.

12. A texaphyrin -chemotherapeutic agent conjugate of claim 11 further comprising platinum(II) or platinum(IV) complexed to said metal chelating site.

13. A pharmaceutical formulation comprising a texaphyrin-chemotherapeutic agent conjugate of claim 4 and a pharmaceutically acceptable excipient.

14. A method of treating atheroma, a tumor or other neoplastic tissue, or a neovascular-related disease comprising administering a subject in need thereof an effective amount of a texaphyrin-chemotherapeutic agent conjugate, with the proviso that the chemotherapeutic agent is not a biomolecule, an antibody, a nucleotide, an oligonucleotide, a peptide, a protein, a steroid, a hormone or hormone mimic, a sappphyrin, or a rubyrin.

15. The method of claim 14 wherein the conjugate is represented by Formula (A) or (B):

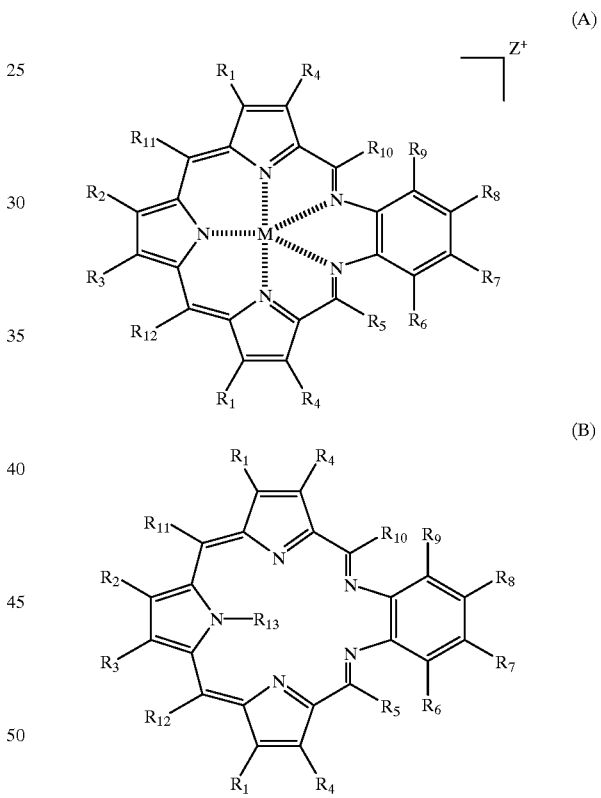

wherein,

Z is zero or an integer less than or equal to 5;

M is hydrogen, a divalent metal cation or a trivalent metal cation;

$R_1$–$R_4$ and $R_6$–$R_9$ are independently hydrogen, halide other than iodide, hydroxyl, alkyl, alkenyl, aryl, haloalkyl other than iodoalkyl, nitro, formyl, acyl, hydroxyalkyl, alkoxy, hydroxyalkoxy, saccharide, aminoalkyl, aminoalkoxy, carboxy, carboxyalkyl, carboxyamide, carboxyamidealkyl, a catalytic group, a couple to a catalytic group, a chemotherapeutic agent, a couple to a chemotherapeutic agent, a platinum(II) metal chelating site, a couple to a platinum(II) metal